US009775899B2

(12) United States Patent
Burkly et al.

(10) Patent No.: US 9,775,899 B2
(45) Date of Patent: Oct. 3, 2017

(54) TREATING NEUROLOGICAL DISORDERS

(71) Applicant: Biogen MA Inc., Cambridge, MA (US)

(72) Inventors: Linda C. Burkly, West Newton, MA (US); Kyungmin Hahm, Lexington, MA (US); Timothy Zheng, Boston, MA (US); Steve Perrin, Newbury, MA (US); John Lincecum, Jamaica Plain, MA (US)

(73) Assignee: Biogen MA Inc., Cambridge, MA (US)

(*) Notice: Subject to any disclaimer, the term of this patent is extended or adjusted under 35 U.S.C. 154(b) by 419 days.

(21) Appl. No.: 13/718,788

(22) Filed: Dec. 18, 2012

(65) Prior Publication Data

US 2013/0095175 A1  Apr. 18, 2013

Related U.S. Application Data

(60) Division of application No. 13/222,097, filed on Aug. 31, 2011, now abandoned, which is a continuation of application No. 11/816,502, filed as application No. PCT/US2006/005597 on Feb. 17, 2006, now abandoned.

(60) Provisional application No. 60/653,813, filed on Feb. 17, 2005.

(51) Int. Cl.
*A61K 39/395* (2006.01)
*G01N 33/68* (2006.01)
*A61K 38/17* (2006.01)

(52) U.S. Cl.
CPC ...... *A61K 39/3955* (2013.01); *A61K 38/1793* (2013.01); *G01N 33/6896* (2013.01); *G01N 2800/2814* (2013.01); *G01N 2800/2835* (2013.01)

(58) Field of Classification Search
None
See application file for complete search history.

(56) References Cited

U.S. PATENT DOCUMENTS

| | | |
|---|---|---|
| 4,777,245 A | 10/1988 | Foung et al. |
| 4,921,698 A | 5/1990 | Shirai et al. |
| 5,073,492 A | 12/1991 | Chen et al. |
| 5,200,313 A | 4/1993 | Carrico |
| 5,223,409 A | 6/1993 | Ladner et al. |
| 5,225,539 A | 7/1993 | Winter |
| 5,624,821 A | 4/1997 | Winter et al. |
| 5,648,260 A | 7/1997 | Winter et al. |
| 5,693,762 A | 12/1997 | Queen et al. |
| 5,858,991 A | 1/1999 | Hellerqvist et al. |
| 5,859,205 A | 1/1999 | Adair et al. |
| 5,877,015 A | 3/1999 | Hardy et al. |
| 5,885,793 A | 3/1999 | Griffiths et al. |
| 6,037,521 A | 3/2000 | Sato et al. |
| 6,046,381 A | 4/2000 | Mucke et al. |
| 6,207,642 B1 | 3/2001 | Wiley |
| 6,258,562 B1 | 7/2001 | Salfeld et al. |
| 6,300,064 B1 | 10/2001 | Knappik et al. |
| 6,407,213 B1 | 6/2002 | Carter et al. |
| 6,448,042 B1 | 9/2002 | Greene et al. |
| 6,492,123 B1 | 12/2002 | Holliger et al. |
| 6,531,447 B1 | 3/2003 | Ruben et al. |
| 6,544,761 B2 | 4/2003 | Greene et al. |
| 6,572,852 B2 | 6/2003 | Smith et al. |
| 6,608,048 B2 | 8/2003 | Tsou et al. |
| 6,630,514 B2 | 10/2003 | Youdim et al. |
| 6,727,225 B2 | 4/2004 | Wiley |
| 6,824,773 B2 | 11/2004 | Wiley |
| 6,943,146 B2 | 9/2005 | Jakubowski et al. |
| 7,001,992 B2 | 2/2006 | Ruben et al. |
| 7,064,244 B2 | 6/2006 | Jakobovits et al. |
| 7,067,475 B2 | 6/2006 | Cerretti et al. |
| 7,074,408 B2 | 7/2006 | Fanslow, III et al. |
| 7,087,225 B2 | 8/2006 | Yu et al. |
| 7,087,725 B2 | 8/2006 | Browning et al. |
| 7,109,298 B2 | 9/2006 | Browning et al. |
| 7,129,061 B1 | 10/2006 | Browning et al. |
| 7,169,387 B2 | 1/2007 | Rennert |
| 7,175,849 B2 | 2/2007 | Baum et al. |
| 7,208,151 B2 | 4/2007 | Browning et al. |
| 7,355,008 B2 | 4/2008 | Stavenhagen et al. |
| 7,368,531 B2 | 5/2008 | Rosen et al. |
| 7,482,430 B2 | 1/2009 | Wiley |
| 7,482,442 B2 | 1/2009 | Ruben et al. |
| 7,495,086 B2 | 2/2009 | Kim et al. |
| 7,498,304 B2 | 3/2009 | Kotkow et al. |
| 7,507,807 B2 | 3/2009 | Wiley |
| 7,517,962 B2 | 4/2009 | Wiley |
| 7,566,769 B2 | 7/2009 | Browning et al. |
| 7,579,001 B2 | 8/2009 | Rennert |

(Continued)

FOREIGN PATENT DOCUMENTS

| | | |
|---|---|---|
| CA | 2064710 A1 | 11/1991 |
| EP | 1 354 950 A1 | 10/2003 |

(Continued)

OTHER PUBLICATIONS

Ronnmark et al (J Immunol Meth 261: 199-211, 2002).*
Klockgether (Cell Tiss Res 318: 115-120, 2004).*
Mustafa et al, Neuroscience 319:116-122, 2016.*
Houlden et al, Acta Neuropath 124: 325-338, 2012.*
Fagan. T, Pink mutations Link Parkinson's disease to mitochondria—ALZFORUM: 1-2, 2004.*
Abbas, A.K. et al. (eds.), "General Properties of Immune Responses", in *Introduction to Immunology, Cellular and Molecular Immunology*. Philadelphia: WB Saunders Co., 1991; Chapter One, pp. 4-12.

(Continued)

*Primary Examiner* — Daniel E Kolker
*Assistant Examiner* — Aditi Dutt
(74) *Attorney, Agent, or Firm* — Fish & Richardson P.C.

(57) ABSTRACT

Methods of treating neuronal disorders, such as mechanical neuronal traumas and neurodegenerative disorders, with TWEAK or a TWEAK receptor blocking agents are presented.

24 Claims, 3 Drawing Sheets

(56) References Cited

U.S. PATENT DOCUMENTS

| | | |
|---|---|---|
| 7,695,934 B2 | 4/2010 | Browning et al. |
| 7,731,963 B2 | 6/2010 | Browning et al. |
| 7,732,588 B2 | 6/2010 | Wiley |
| 7,754,884 B2 | 7/2010 | Bornhop et al. |
| 7,829,675 B2 | 11/2010 | Kim et al. |
| 8,048,422 B2 | 11/2011 | Burkly et al. |
| 8,048,635 B2 | 11/2011 | Burkly et al. |
| 8,440,189 B2 | 5/2013 | Rennert |
| 8,506,958 B2 | 8/2013 | Burkly et al. |
| 8,728,475 B2 | 5/2014 | Burkly et al. |
| 9,011,859 B2 | 4/2015 | Burkly et al. |
| 2002/0004041 A1 | 1/2002 | Albert et al. |
| 2002/0010180 A1 | 1/2002 | Feldmann et al. |
| 2002/0015703 A1 | 2/2002 | Rennert |
| 2002/0041876 A1 | 4/2002 | Wiley |
| 2002/0042368 A1 | 4/2002 | Fanslow, III et al. |
| 2002/0110853 A1 | 8/2002 | Wiley |
| 2003/0044893 A1 | 3/2003 | Baum et al. |
| 2003/0070185 A1 | 4/2003 | Jakobovits et al. |
| 2003/0100074 A1 | 5/2003 | Yu et al. |
| 2003/0148314 A1 | 8/2003 | Berger et al. |
| 2003/0162712 A1 | 8/2003 | Cerretti et al. |
| 2003/0170228 A1 | 9/2003 | Ashkenazi et al. |
| 2003/0198640 A1 | 10/2003 | Yu et al. |
| 2003/0211096 A1 | 11/2003 | Ashkenazi et al. |
| 2003/0211993 A1 | 11/2003 | Jakubowski et al. |
| 2003/0216546 A1 | 11/2003 | Tykocinski et al. |
| 2003/0228305 A1 | 12/2003 | Frantz et al. |
| 2004/0014176 A1 | 1/2004 | Ashkenazi et al. |
| 2004/0018170 A1 | 1/2004 | Shirwan |
| 2004/0028658 A1 | 2/2004 | Faustman |
| 2004/0033225 A1 | 2/2004 | Browning et al. |
| 2004/0033495 A1 | 2/2004 | Murray et al. |
| 2004/0038349 A1 | 2/2004 | Hilbert et al. |
| 2004/0047854 A1 | 3/2004 | Black et al. |
| 2004/0076955 A1 | 4/2004 | Mack et al. |
| 2004/0091473 A1 | 5/2004 | DuBose et al. |
| 2004/0175744 A1 | 9/2004 | Hu et al. |
| 2004/0176296 A1 | 9/2004 | Holtzman et al. |
| 2004/0203083 A1 | 10/2004 | Buechler et al. |
| 2004/0253637 A1 | 12/2004 | Buechler et al. |
| 2005/0008625 A1 | 1/2005 | Balint et al. |
| 2005/0008636 A1 | 1/2005 | Rennert |
| 2005/0037000 A1 | 2/2005 | Stravenhagen et al. |
| 2005/0054047 A1 | 3/2005 | Wiley |
| 2005/0054568 A1 | 3/2005 | Ling et al. |
| 2005/0079574 A1 | 4/2005 | Bond |
| 2005/0112666 A1 | 5/2005 | Browning et al. |
| 2005/0118629 A1 | 6/2005 | Browning et al. |
| 2005/0143297 A1 | 6/2005 | Rosat |
| 2005/0181375 A1 | 8/2005 | Aziz et al. |
| 2005/0208046 A1 | 9/2005 | Kim et al. |
| 2005/0208500 A1 | 9/2005 | Erlander et al. |
| 2005/0266555 A1 | 12/2005 | Lu et al. |
| 2006/0003932 A1 | 1/2006 | Jakubowski et al. |
| 2006/0084143 A1 | 4/2006 | Wiley |
| 2006/0127397 A1 | 6/2006 | Strittmatter et al. |
| 2006/0211090 A1 | 9/2006 | Bejanin et al. |
| 2006/0240004 A1 | 10/2006 | Burkly et al. |
| 2006/0252122 A1 | 11/2006 | Browning et al. |
| 2007/0110745 A1 | 5/2007 | Rennert |
| 2007/0280940 A1 | 12/2007 | Winkles et al. |
| 2008/0004432 A1 | 1/2008 | Ruben et al. |
| 2008/0008714 A1 | 1/2008 | Browning et al. |
| 2008/0187544 A1 | 8/2008 | Burkly et al. |
| 2008/0241163 A1 | 10/2008 | Burkly et al. |
| 2008/0279853 A1 | 11/2008 | Burkly et al. |
| 2008/0286271 A1 | 11/2008 | Ashkenazi et al. |
| 2008/0292622 A1 | 11/2008 | Burkly et al. |
| 2009/0068102 A1 | 3/2009 | Burkly et al. |
| 2009/0124993 A1 | 5/2009 | Burkly et al. |
| 2009/0148900 A1 | 6/2009 | Ruben et al. |
| 2009/0311313 A1 | 12/2009 | Burkly et al. |
| 2009/0324602 A1 | 12/2009 | Garber et al. |
| 2010/0061985 A1 | 3/2010 | Rennert |
| 2010/0183548 A1 | 7/2010 | Wiley |
| 2010/0260761 A1 | 10/2010 | Browning et al. |
| 2010/0272721 A1 | 10/2010 | Burky et al. |
| 2010/0284933 A1 | 11/2010 | Burkly |
| 2011/0002924 A1 | 1/2011 | Browning et al. |
| 2012/0009178 A1 | 1/2012 | Burkly et al. |
| 2012/0014953 A1 | 1/2012 | Burkly et al. |
| 2012/0015024 A1 | 1/2012 | Burkly et al. |
| 2012/0020913 A1 | 1/2012 | Burkly |
| 2012/0020970 A1 | 1/2012 | Burkly et al. |
| 2012/0027751 A1 | 2/2012 | Rennert |
| 2012/0121583 A1 | 5/2012 | Baehner et al. |
| 2012/0183542 A1 | 7/2012 | Burkly et al. |
| 2012/0301444 A1 | 11/2012 | Clarke et al. |
| 2013/0216496 A1 | 8/2013 | Burkly et al. |
| 2014/0093519 A1 | 4/2014 | Burkly |
| 2015/0291688 A1 | 10/2015 | Burkly et al. |

FOREIGN PATENT DOCUMENTS

| | | |
|---|---|---|
| EP | 1 566 636 A1 | 8/2005 |
| EP | 1 764 109 | 3/2007 |
| EP | 1 721 157 B1 | 4/2011 |
| JP | 5-501062 | 3/1993 |
| JP | 5-501062 A | 3/1993 |
| JP | 2002-527096 | 8/2002 |
| WO | WO 92/22653 | 12/1992 |
| WO | WO 95/14772 A1 | 6/1995 |
| WO | WO 96/18725 A1 | 6/1996 |
| WO | WO 98/05783 A1 | 2/1998 |
| WO | WO 98/35061 A2 | 8/1998 |
| WO | WO 98/52976 A1 | 11/1998 |
| WO | WO 98/55508 A2 | 12/1998 |
| WO | WO 99/11791 A2 | 3/1999 |
| WO | WO 99/19490 A1 | 4/1999 |
| WO | WO 99/59614 A1 | 11/1999 |
| WO | WO 99/61471 A2 | 12/1999 |
| WO | WO 00/23459 A1 | 4/2000 |
| WO | WO 00/34317 A2 | 6/2000 |
| WO | WO 00/37638 A2 | 6/2000 |
| WO | WO 00/42073 A1 | 7/2000 |
| WO | WO 00/44777 | 8/2000 |
| WO | WO 01/45730 | 6/2001 |
| WO | WO 01/45730 A2 | 6/2001 |
| WO | WO 01/53486 A1 | 7/2001 |
| WO | WO 01/55112 | 8/2001 |
| WO | WO 01/85193 A2 | 11/2001 |
| WO | WO 02/22166 A2 | 3/2002 |
| WO | WO 02/053737 | 7/2002 |
| WO | WO 02/102994 A2 | 12/2002 |
| WO | WO 03/040307 A2 | 5/2003 |
| WO | WO 03/086311 A2 | 10/2003 |
| WO | WO 2004/003164 | 1/2004 |
| WO | WO 2004/074433 * | 9/2004 |
| WO | WO 2004/074433 A2 | 9/2004 |
| WO | WO 2005/010045 A1 | 2/2005 |
| WO | WO 2005/053728 | 6/2005 |
| WO | WO 2005/080972 A1 | 9/2005 |
| WO | WO 2005/120437 | 12/2005 |
| WO | WO 2006/047172 A1 | 5/2006 |
| WO | WO 2006/052926 A2 | 5/2006 |
| WO | WO 2006/088890 A2 | 8/2006 |
| WO | WO 2006/089095 A2 | 8/2006 |
| WO | WO 2006/096487 A2 | 9/2006 |
| WO | WO 2006/122187 A2 | 11/2006 |
| WO | WO 2006/125632 | 11/2006 |
| WO | WO 2006/130374 A2 | 12/2006 |
| WO | WO 2006/130429 A2 | 12/2006 |
| WO | WO 2006/138219 A2 | 12/2006 |
| WO | WO 2008/048924 A2 | 4/2008 |
| WO | WO 2009/020933 | 2/2009 |
| WO | WO 2009/140177 A2 | 11/2009 |
| WO | WO 2010/085648 A2 | 7/2010 |
| WO | WO 2010/088534 A1 | 8/2010 |
| WO | WO 2011/084714 | 7/2011 |
| WO | WO 01/97500 | 8/2011 |
| WO | WO 2011/097500 | 8/2011 |

(56) References Cited

FOREIGN PATENT DOCUMENTS

| WO | WO 2012/045671 | 4/2012 |
| WO | WO 2015/051234 | 4/2015 |

OTHER PUBLICATIONS

Abbas, A.K. et al. (eds.), "Immunity to Microbes", in *Introduction to Immunology. Cellular and Molecular Immunology*. Philadelphia: WB Saunders Co., 1991; Chapter Fifteen, pp. 302-314.
Abreu-Martin et al., "Divergent Induction of Apoptosis and IL-8 Secretion in HT-29 Cells in Response to TNF-α and Ligation of Fas Antigen", *J. Immunol.* 155:4147-4154 (1995).
Agrawal, "Antisense Oligonucleotides: Towards Clinical Trials", *TIBTECH* 14:376-387 (1996).
Akahori et al., "Immunoglobulin kappa light chain VLJ region [*Homo sapiens*]", NCBI database accession No. GI:21669075, GenBank Accession No. BAC01562 (Jun. 25, 2001).
Amakawa et al., "Impaired Negative Selection of T Cells in Hodgkin's Disease Antigen CD30-Deficient Mice", *Cell* 84:551-562 (1996).
Amendola et al., "Altered sensorimotor development in a transgenic mouse model of amyotrophic lateral sclerosis", *Eur. J. Neurosci.* 20:2822-2826 (2004).
Anderson, "Human Gene Therapy", *Nature* 392:25-30 (1998).
Andrews et al., "Spontaneous murine Lupus-like Syndromes", *J. Exp. Med.* 148:1198-1215 (1978).
Angal et al., "A single amino acid substitution abolishes the heterogeneity of chimeric mouse/human (IgG4) antibody", *Mol. Immunol.* 30:105-108 (1993).
Ashkenazi et al., "Death Receptors: Signaling and Modulation", *Science, New Series* 281(5381):1305-1308 (1998).
Bach-Elias et al., "Presence of autoantibodies against small nuclear ribonucleoprotein epitopes in Chagas' patients' sera", *Parasitol. Res.* 84:796-799 (1998).
Badley et al., "Upregulation of Fas Ligand Expression by Human Immunodeficiency Virus in Human Macrophages Mediates Apoptosis of Uninfected T Lymphocytes", *J. Virology* 70:199-206 (1996).
Barrios et al., "Length of the antibody heavy chain complementarity determining region 3 as a specificity-determining factor", *J. Mol. Recog.* 17:332-338 (2004).
Bateller et al., "Liver fibrosis", *J. Clin. Invest.*, 115(2):209-218 (2005).
Bendele et al., "Combination Benefit of Treatment with the Cytokine Inhibitors Interleukin-1 Receptor Antagonist and PEGylated Soluble Tumor Necrosis Factor Receptor Type 1 in Animal Models of Rheumatoid Arthritis", *Arthritis Rheum.* 43(12):2648-2659 (2000).
Bodmer et al., "TRAMP, a Novel Apoptosis-Mediating Receptor with Sequence Homology to Tumor Necrosis Factor Receptor 1 and Fas(Apo-1/CD95)", *Immunity* 6:79-88 (1997).
Boor et al., "Treatment targets in renal fibrosis", *Nephrol. Dial. Transplant.* 22:3391-3407 (2007).
Bose et al., "Problems in using statistical analysis of replacement and silent mutations in antibody genes for determining antigen-driven affinity selection", *Immunology* 116:172-183 (2005).
Boucraut et al., "Anti-TWEAK Monoclonal Antibodies Reduce CNS Immune Cell Infiltration and Severity of Experimental Autoimmune Encephalomyelitis" *Aegean Conference Series, vol. 12: Autoimmunity: Mechanisms and Novel Treatments.* Myconos, Greece, Oct. 8-13, 2003; Abstract No. 64, p. 89.
Bowie et al., "Deciphering the Message in Protein Sequences: Tolerance to Amino Acid Substitutions", *Science* 247:1306-1310 (1990).
Branch, "A good antisense molecule is hard to find", *TIBS* 23:45-50 (1998).
Brojatsch et al., "CAR1, a TNFR-Related Protein, is a Cellular Receptor for Cytopathic Avian Leukosis-Sarcoma Viruses and Mediates Apoptosis", *Cell* 87:845-855 (1996).

Brown et al., "The Fn14 cytoplasmic tail binds tumour-necrosis-factor-receptor-associated factors 1, 2, 3 and 5 and mediates nuclear factor-kappaB activation", *Biochem. J.* 371:395-403 (2003).
Browning et al., "Characterization of Surface Lymphotoxin Forms", *J. Immunol.* 154:33-46 (1995).
Browning et al., "Preparation and Characterization of Soluble Recombinant Heterotrimeric Complexes of Human Lymphotoxins Alpha and Beta", *J. Biol. Chem.* 271:8618-8626 (1996).
Browning et al., "Signaling through the Lymphotoxin Beta Receptor Induces the Death of Some Adenocarcinoma Tumor Lines", *J. Exp. Med.* 183:867-878 (1996).
Browning et al., "Studies on the Differing Effects of Tumor Necrosis Factor and Lymphotoxin on the Growth of Several Human Tumor Lines", *J. Immunol.* 143:1859-1867 (1989).
Browning, J., Second Declaration under 37 CFR 1.132 of Jeffrey Browning, Ph.D. from U.S. Appl. No. 09/245,198, Declaration filed on Jun. 27, 2005.
Bucher et al., "A Generalized Profile Syntax for Biomolecular Sequence Motifs and Its Function in Automatic Sequence Interpretation", Proc. Second International Conference on Intelligent Systems for Molecular Biology. Altman, Brutlag, Karp, Lathrop, Searls (Eds.), pp. 53-61 (1994).
Burgess et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue", *J. Cell. Biol.* 111:2129-2138 (1990).
Campbell et al., "Proinflammatory Effects of TWEAK/Fn14 Interactions in Glomerular Mesangial Cells", *J. Immunol.* 176:1889-1898 (2006).
Campbell et al., "The Role of TWEAK/Fn14 in the Pathogenesis of Inflammation and Systemic Autoimmunity", *Frontiers Biosci.* 9:2273-2284 (2004).
Campbell, "The Role of TWEAK/Fn14 Interactions in Antibody Induced Glomerulonephritis", Dissertation, Albert Einstein College of Medicine, Yeshiva University, Nov. 2007. ProQuest, LLC, Ann Arbor, MI, 2009; UMI Microform No. 3340631.
Cassiano et al., "Molecular cloning of a novel receptor for TWEAK", *Scand. J. Immunol.* 51 (Suppl. 1):1-III (Abstract 2.2) (2000).
Castro et al., "Fas Modulation of Apoptosis during Negative Selection of Thymocytes" *Immunity* 6:617-627 (1996).
Chaplin et al., "Cytokine regulation of secondary lymphoid organ development", *Curr. Opin. Immunol.* 10:289-297 (1998).
Chicheportiche et al., "Down-Regulated Expression of TWEAK mRNA in Acute and Chronic Inflammatory Pathologies", *Biochem. Biophys. Res. Commun.* 279(1):162-165 (2000).
Chicheportiche et al., "Proinflammatory Activity of TWEAK on Human Dermal Fibroblasts and Synoviocytes: Blocking and Enhancing Effects of Anti-TWEAK Monoclonal Antibodies", *Arthritis Res.* 4(2):126-133 (2002). Epub Nov. 9, 2001.
Chicheportiche et al., "TWEAK, a new secreted ligand in the tumor necrosis factor family that weakly induces apoptosis", *J. Biol. Chem.* 272(51):32401-32410 (Dec. 19, 1997).
Chothia et al., "Structural repertoire of the human $V_H$ segments", *J. Mol. Biol.* 227:799-817 (1992).
Clackson et al., "Making antibody fragments using phage display libraries" *Nature* 352:624-628 (1991).
Clark et al., "Trends in antibody sequence changes during the somatic hypermutation process", *J. Immunol.* 177:333-340 (2006).
Consilvio et al. "Neuroinflammation, COX-2, and ALS—a dual role?", *Exper. Neurol.* 187:1-10 (2004).
Courtenay et al., "Immunisation against heterologous type II collagen induces arthritis in mice", *Nature* 283:666-668 (1980).
Culp et al. "Anti-TweakR antibodies inhibit tumor growth in vivo through dual mechanisms", *Proc. Annu. Mtg. Amer. Assoc. Cancer Res.* 49:354, Abstract 1511 (Apr. 16, 2008).
Cwirla et al., "Peptides on Phage: A Vast Library of Peptides for Identifying Ligands", *Proc. Natl. Acad. Sci. USA* 87:6378-6382 (1990).
Dallman, "Cytokines and transplantation: Th1/Th2 regulation of the immune response to solid organ transplants in the adult", *Curr. Opin. Immunol.* 7:632-638 (1995).

(56) References Cited

OTHER PUBLICATIONS

Darnay et al., "Signal Transduction by Tumor Necrosis Factor and Tumor Necrosis Related Ligands and Their Receptors", *Ann. Rheum. Dis.* 58(Suppl. 1):I2-113 (1999).
David et al., "A study of the structural correlates of affinity maturation: Antibody affinity as a funcetion of chemical interactions, structural plasticity and stability", *Molecular Immunology* 44:1342-1351 (2007).
Davies et al., "Single antibody domains as small recognition units: design and in vitro antigen selection of camelized, human VH domains with improved protein stability", *Protein Eng.* 9(6):531-537 (1996).
De Benedette et al., "Role of 4-1BB Ligand in Costimulation of T Lymphocyte Growth and its Upregulation on M12 B Lymphomas by cAMP", *J. Exp. Med.* 181:985-992 (1995).
De Pascalis et al., "Grafting of 'Abbreviated' Complementarity-Determining Regions Containing Specificity-Determining Residues Essential for Ligand Contact to Engineer a Less Immunogenic Humanized Monoclonal Antibody" *J. Immunol.* 169:3076-3084 (2002).
De Wit et al., "Preferential Activation of Th2 Cells in Chronic Graft-versus-Host Reaction", *J. Immunol.* 150(2):361-366 (1993).
Degli-Esposti, "To die or not to die—the quest of the TRAIL receptors", *J. Leukocyte Biol.* 65:535-542 (1999).
Dermer, "Another Anniversary for the War on Cancer", *BioTechnology* 12:320 (1994).
Desplat-Jego et al., "Anti-TWEAK monoclonal antibodies reduce immune cell infiltration in the central nervous system and severity of experimental autoimmune encephalomyelitis", *Clin. Immunol.* 117(1):15-23 (2005).
Desplat-Jégo et al., "TWEAK is Expressed by Glial Cells, Induces Astrocyte Proliferation and Increases EAE Severity", *J. Neuroimmunol.* 133:116-123 (2002).
Dias et al., "The Role of CXC Chemokines in the Regulation of Tumor Angiogenesis", *Cancer Invest.* 19:732-738 (2001).
Donahue et al., "TWEAK is an Endothelial Cell Growth and Chemotactic Factor That Also Potentiates FGF-2 and VEGF-A Mitogenic Activity", *Arterioscler. Thromb. Vasc. Biol.* 23:594-600 (2003).
Droz, D., "Clinico-anatomical forms of primary glomerulonephritis", *Rev. Med. Interne* 15(6):390-398 (1994) (Abstract only; article in French).
Durie et al., "Antibody to the Ligand of CD40, gp39, Blocks the Occurrence of the Acute and Chronic Forms of Graft-vs-Host Disease", *J. Clin. Invest.* 94:1333-1338 (1994).
Eck et al., "The Structure of Human Lymphotoxin (Tumor Necrosis Factor-Beta) at 1.9-Å Resolution", *J. Biol. Chem.* 267:2119-2122 (1992).
European Patent Application No. 03721647: Supplementary Partial Search Report, dated Aug. 9, 2005.
European Patent Application No. 06760258: Extended Search Report, including Search Opinion and Supplementary Search Report, dated Jun. 19, 2009.
European Patent Application No. 08104327: Extended Search Report, including Search Opinion, dated Feb. 6, 2009.
European Patent Application No. 10181803: Extended Search Report, including Search Opinion, dated Jul. 6, 2012.
European Patent Application No. 10181810: Extended Search Report, including Search Opinion, dated Jul. 6, 2012.
Falk et al., "Expression of the APO-1 Antigen in Burkitt Lymphoma Cell Lines Correlates with a Shift Towards a Lymphoblastoid Phenotype", *Blood* 79:3300-3306 (1992).
Feng et al., "The Fn14 Immediate-Early Response Gene is Induced During Liver Regeneration and Highly Expressed in Both Human and Murine Hepatocellular Carcinomas", *Am. J. Pathol.* 156(4):1253-1261 (2000).
Flynn et al., "CD4 T Cell Cytokine Differentiation: The B Cell Activation Molecule, OX40 Ligand, Instructs CD4 T Cells to Express Interleukin 4 and Upregulates Expression of the Chemokine Receptor, Blr-1", *J. Exp. Med.* 188:297-304 (1998).

Fox, D., "Biological Therapies: A Novel Approach to the Treatment of Autoimmune Disease", *Am. J. Med.* 99:82-88 (1995).
Fujimoto et al., "Interleukin-6 Blockade Suppresses Autoimmune Arthritis in Mice by the Inhibition of Inflammatory Th17 Responses", *Arthritis & Rheumatism* 58:3710-3719 (2008).
Funakoshi et al., "Inhibition of Human B-Cell Lymphoma Growth by CD40 Stimulation", *Blood* 83:2787-2794 (1994).
Galle et al., "Involvement of the CD95 (APO-1/Fas) Receptor and Ligand in Liver Damage", *J. Exp. Med.* 182:1223-1230 (1995).
Games et al., "Alzheimer-type neuropathology in transgenic mice overexpressing V717F beta-amyloid precursor protein", *Nature* 373:523-527 (1995).
Gauchat et al., "Human CD40-Ligand: Molecular Cloning, Cellular Distribution and Regulation of Expression by Factors Controlling IgE Production", *FEBS Lett.* 315:259-266 (1993).
Genbank Acc. No. AAB49141, "Anti-DNA immunoglobulin heavy chain IgG [Mus musculus]" (1996).
Genentech, Inc., Full Prescribing Information for Actrema (Jan. 2010) (24 pages).
Gleichmann et al., "A systemic lupus erythematosus (SLE)-like disease in mice induced by abnormal T-B cell cooperation. Preferential formation of autoantibodies characteristic of SLE", *Eur. J. Immunol.* 12:152-159 (1982).
Grewal et al., "The CD40 Ligand. At the Center of the Immune Universe?", *Immunol. Res.* 16:59-70 (1997).
Grewal et al., "The Role of CD40 Ligand in Costimulation and T-Cell Activation", *Immunol. Rev.* 153:85-106 (1996).
Gruss et al., "Pleiotrophic Effects of the CD30 Ligand on CD30-Expressing Cells and Lymphoma Cell Lines", *Blood* 83:2045-2056 (1994).
Gruss et al., "Tumor Necrosis Factor Ligand Superfamily: Involvement in the Pathology of Malignant Lymphomas" *Blood* 85:3378-3404 (1995).
Hahm et al., "TWEAK overexpression induces hyperplasia in liver and kidney", *FASEB J.* 17(4-5):Abstract No. 471.5 (2003).
Han et al., "Identification of Differentially Expressed Genes in Pancreatic Cancer Cells Using cDNA Microarray", *Cancer Research* 62:2890-2896 (May 15, 2002).
Han et al., "Overexpression of FN14/TEAK receptor in pancreatic cancer", *Proc. Am. Assoc. Cancer Res. Annual Meeting* 46(Suppl. S):Abstract No. 2363 (Apr. 18, 2005).
Hess et al., "A Novel Function of CD40: Induction of Cell Death in Transformed Cells", *J. Exp. Med.* 183:159-167 (1996).
Hillier, L. et al., "The Wash U-Merck EST project yy19a08.s1 Homo sapiens cDNA clone 271670 3", EMBL Database Entry HS070272, Accesion No. N35070 (Jan. 19, 1996).
Hillier, L. et al., "The WashU-Merck EST project yy19a08.s1 Homo sapiens cDNA clone 154742 5", EMBL Database Entry HS379117, Accession No. R55379 (May 28, 1995).
Ho et al., "Soluble Tumor Necrosis Factor-Like Weak Inducer of Apoptosis Overexpression in HEK293 Cells Promotes Tumor Growth and Angiogenesis in Athymic Nude Mice", *Cancer Research* 64:8968-8972 (Dec. 15, 2004).
Ike et al., "Solid Phase Synthesis of Polynucleotides. VIII. Synthesis of Mixed Oligodeoxyribonucleotides by the Phosphotriester Solid Phase Method", *Nucl. Acids Res.* 11:477-488 (1983).
International Preliminary Examination Report issued in International Patent Application No. PCT/US03/11350; Date of Mailing: Nov. 23, 2004.
International Search Report issued in International Patent Application No. PCT/US03/11350; Date of Mailing: Mar. 10, 2004.
International Search Report and Written Opinion issued in International Patent Application No. PCT/US06/05217; Date of Mailing: Aug. 4, 2006.
International Search Report and Written Opinion issued in International Patent Application No. PCT/US06/05597; Date of Mailing: May 21, 2008.
International Search Report and Written Opinion issued in International Patent Application No. PCT/US06/022830; Date of Mailing: Jan. 26, 2007.
International Search Report and Written Opinion issued in International Patent Application No. PCT/US06/19706; Date of Mailing: Oct. 9, 2007.

(56) References Cited

OTHER PUBLICATIONS

Iwasaki et al., "Cotreatment of amyotrophic lateral sclerosis patients", *Rinsho Shinkeigaku* 39:1253-1255 (1999) (Abstract).
Jain et al., "A Novel Role for Tumor Necrosis Factor Like Weak Inducer of Apoptosis (TWEAK) in the Development of Cardiac Dysfunction and Failure", *Circulation* 119:2058-2068, with supplemental material (2009).
Jakubowski et al., "Dual role for TWEAK in angiogenic regulation", *J. Cell Sci.* 115(Pt. 2):267-274 (Jan. 15, 2002).
Jakubowski et al., "TWEAK induces liver progenitor cell proliferation", *J. Clin. Invest.* 115(9):2330-2340 (Sep. 2005).
Jakubowski, A. et al., "TWEAK Synergizes with Basis Fibroblast Growth Factor to Induce Endothelial Cell Proliferation, Migration and Lumen Morphogenesis", *Scand. J. Immunol.* 51(Suppl. 1):62, Abstract 1.30 (2000).
Juengst, "What next for human gene therapy", *BMJ* 326:1410-1411 (2003).
Kaduka et al., "TWEAK Mediates Anti-Tumor Effect of Tumor-Infiltrating Macrophage", *Biochem. Biophys. Res. Commun.* 331:384-390 (2005).
Kalled et al., "Anti-CD40 Ligand Antibody Treatment of SNF1 Mice with Established Nephritis: Preservation of Kidney Function", *J. Immunol.* 160:2158-2165 (1998).
Kamata et al., "Involvement of TNF-Like Weak Inducer of Apoptosis in the Pathogenesis of Collagaen-Induced Arthritis" *J. Immunol.* 177:6433-6439 (2006).
Kaplan et al., "Th2 Lymphocytes Kill Antigen Presenting Macrophages Through a TWEAK Dependant Pathway", *J. Invest. Med.* 46(7):287A (1998).
Kaplan et al., "The Apoptotic Ligands TRAIL, TWEAK, and Fas Ligand Mediate Monocyte Death Induced by Autologous Lupus T Cells", *J. Immunol.* 169:6020-6029 (2002).
Kaplan et al., "TRAIL (Apo2 Ligand) and TWEAK (Apo3 Ligand) Mediate CD4$^+$ T Cell Killing of Antigen-Presenting Macrophages", *J. Immunol.* 164:2897-2904 (2000).
Katsikis et al., "Fas Antigen Stimulation Induces Marked Apoptosis of T Lymphocytes in Human Immunodeficiency Virus-infected Individuals", *J. Exp. Med.* 181:2029-2036 (1995).
Kawakita et al., "Functional expression of TWEAK in human hepatocellular carcinoma: possible implication in cell proliferation and tumor angiogenesis", *Biochem. Biophys. Res. Commun.* 318:726-733 (2004).
Kirk et al., "CTLA4-Ig and anti-CD40 ligand prevent renal allograft rejection in primates", *Proc. Natl. Acad. Sci. USA* 94:8789-8794 (1997).
Kobrin et al., "A V region mutation in a phosphocholine-binding monoclonal antibody results in loss of antigen binding", *J. Immunol.* 146:2017-2020 (1991).
Kornek et al., "Multiple Sclerosis and Chronic Autoimmune Encephalomyelitis. A Comparative Quantitative Study of Axonal Injury in Active, Inactive, and Remyelinated Lesions", *Am. J. Pathol.* 157(1):267-276 (2000).
Krenger et al., "Graft-versus-Host Disease and the Th1/Th2 Paradigm", *Immunol. Res.* 15:50-73 (1996).
Kuhn et al., "A mouse model of graded contusive spinal cord injury", *J. Neurotrauma* 15:125-140 (1998).
Lee et al., "T Cell Receptor-dependent Cell Death of T Cell Hybridomas Mediated by the CD30 Cytoplasmic Domain in Association with Tumor Necrosis Factor Receptor-Associated Factors", *J. Exp. Med.* 183:669-674 (1996).
Lennon et al., "The I.M.A.G.E. Consortium: An Integrated Molecular Analysis of Genomes and Their Expression", *Genomics* 33:151-152 (Apr. 1996) with Medline Abstract page.
Lenschow et al., "Differential Effects of Anti-B7-1 and Anti-B7-2 Monoclonal Antibody Treatment on the Development of Diabetes in the Nonobese Diabetic Mouse", *J. Exp. Med.* 181:1145-1155 (1995).
Lin et al., "Very late antigen 4 (VLA4) antagonists as anti-inflammatory agents", *Curr. Opin. Chem. Biol.* 2:453-457 (1998).

Lund et al., "Human FcγRI and FcγRII interact with distinct but overlapping sites on human IgG", *J. Immunol.* 147:2657-2662 (1991).
Lynch et al., "TWEAK Induces Angiogenesis and Proliferation of Endothelial Cells", *J. Biol. Chem.* 274(13):8455-8459 (1999).
Lynch et al., "TWEAK Induces Proliferation in Endothelial Cells and Substitutes for EGF and Hydrocortisone in Culture", *J. Interferon Cytokine Res.* 18:A-46, Abstract 2.16 (1998).
Mackay et al., "Turning off follicular dendritic cells", *Nature* 395:26-27 (1998).
Markan et al., "Up regulation of the GRP-78 and GADD-153 and down regulation of Bcl-2 proteins in primary glomerular diseases: a possible involvement of the ER stress pathway in glomerulonephritis", *Mol. Cell Biochem.* 324:131-138 (2009).
Marra et al., "The WashU-HHMI Mouse EST project. my18d09.r1 Barstead mouse heart MPLRB3 Mus musculus cDNA clone 696209 5." GenBank Database Accession No. AA221610 (Feb. 15, 1997).
Marsters et al., "Identification of a ligand for the death-domain-containing receptor Apo3", *Current Biology* 8:525-528 (1998).
Martin-Villalba et al., "Therapeutic Neutralization of CD-95-Ligand and TNF Attenuates Brain Damage in Stroke", *Cell Death Diff.* 8:679-686 (2001).
Masliah et al., "Dopaminergic Loss and Inclusion Body Formation in α-Synuclein Mice: Implications for Neurodegenerative Disorders", *Science* 287:1265-1269 (2000).
Mattson et al., "NF-κB in neuronal plasticity and neurodegenerative disorders", *J. Clin. Invest.* 107:247-254 (2001).
Meighan-Mantha et al., "The Mitogen-inducible Fn14 Gene Encodes a Type I Transmembrane Protein that Modulates Fibroblast Adhesion and Migration", *J. Biol. Chem.* 274(46):33166-33176 (Nov. 12, 1999).
Michaelson et al., "Tweak induces mammary epithelial branching morphogenesis", *Oncogene* 24:2613-2624 (2005).
Miller et al., "Genetic Studies of the lac Repressor. IX. Generation of Altered Proteins by the Suppression of Nonsense Mutations", *J. Mol. Biol.* 131:191-222 (1979).
Miller et al., "Riluzole for amyotrophic lateral Sclerosis (AS)/motor neuron disease (MND)", *Cochrane Database Syst. Rev.*, Issue 2. Art. No. CD001447, pp. 1-25 (2002).
Mohan et al., "Interaction Between CD40 and Its Ligand gp39 in the Development of Murine Lupus Nephritis", *J. Immunol.* 154:1470-1480 (1995).
Montgomery et al., "Herpes Simplex Virus-1 Entry into Cells Mediated by a Novel Member of the TNF/NGF Receptor Family", *Cell* 87:427-436 (1996).
Morgan et al., "The N-terminal end of the CH2 domain of chimeric human IgG1 anti-HLA-DR is necessary for C1q, FcγRI and FcγRIII binding", *Immunology* 86:319-324 (1995).
Morris et al., "Experimental Induction of Systemic Lupus Erythematosus by Recognition of Foreign Ia", *Clin. Immunol. Immunopathol.* 57:263-273 (1990).
Mueller et al., "Targeting fibroblast growth-factor-inducible-14 signaling protects from chronic relapsing experimental autoimmune encephalomyelitis", *J. Neuroimmunol.* 159(1-2):55-65 (2005).
Murphy, "Revisiting graft-versus-host disease models of autoimmunity: new insights in immune regulatory processes", *J. Clin. Invest.* 106(6):745-747 (2000).
Nagata, S., "Apoptosis by Death Factor" *Cell* 88:355-365 (1997).
Nakaya et al., "Regulation of Asialoglycoprotein Receptor Synthesis by Inflammation-Related Cytokines in HepG2 Cells", *J. Gastroenterol.* 29:24-30 (1994).
Nakayama et al., "Characterization of murine TWEAK and its receptor (Fn14) by monoclonal antibodies", *Biochem. Biophys. Res. Commun.* 306(4):819-825 (Jul. 11, 2003).
Nakayama et al., "Fibroblast Growth Factor-Inducible 14 Mediates Multiple Pathways of TWEAK-Induced Cell Death", *J. Immunol.* 170:341-348 (2003).
Nakayama et al., "Involvement of TWEAK in Interferon γ-Stimulated Monocyte Cytotoxicicity", *J. Exp. Med.* 192(9):1373-1379 (2000).
Nakayama et al., "Multiple Pathways of TWEAK-Induced Cell Death", *J. Immunol.* 168:734-743 (2002).

(56) References Cited

OTHER PUBLICATIONS

Neutra et al., "Intestinal Epithelium: A Model System for Study of Cell Differentiation and Polarized Cell Functions", in *Functional Epithelia Cells in Culture*. Liss (ed.), 1989; pp. 363-398.
Ngo et al., "Computational Complexity, Protein Structure Prediction, and the Levinthal Paradox", in *The Protein Folding Problem*. K. Merz, Jr. and S. Le Grand (eds.) Boston, MA: Birkhauser, 1994; Chapter 14, pp. 433-435, 492-494.
Orkin et al., Report and Recommendations of the Panel to Assess the NIH Investment in Research on Gene Therapy (Dec. 7, 1995).
Patent Interference No. 105,513, Paper 106, Memorandum Opinion and Order, Decision on Motions.
Patent Interference No. 105,513, Paper 107, Decision—Bd. R. 125, Decision on Browning Misc. Motion 4 for Sanctions.
Patent Interference No. 105,513, Paper 108, Judgement, Preliminary Motions—Bd. R. 127.
Pepper et al., "Biphasic effect of transforming growth factor-β1 on in vitro angiogenesis", *Exp. Cell Res.* 204(2):356-363 (Feb. 1993).
Perper et al., "TWEAK is a novel arthritogenic mediator", *J. Immunol.* 177(4):2610-2620 (Aug. 15, 2006).
Pitti et al., "Induction of Apoptosis by Apo-2 Ligand, a New Member of the Tumor Necrosis Factor Cytokine Family", *J. Biol. Chem.* 271:12687-12690 (1996).
Plowman et al., "Human Tumor Xenograft Models in NCI Drug Development", in *Anticancer Drug Development Guide: Preclinical Screening, Clinical Trials and Approval*. B. Teicher (ed.), Humana Press Inc., Totown, 1997; pp. 101-125.
Portanova et al., "Lupus-like autoimmunity in murine graft-versus-host disease", *Concepts Immunopathol.* 6:119-140 (1988).
Portolano et al., "Lack of promiscuity in autoantigen-specific H and L chain combinations as revealed by human H and L chain 'Roulette'" *J. Immunol.* 150(3):880-887 (1993).
Potrovita et al., "Tumor Necrosis Factor-Like Weak Inducer of Apoptosis-Induced Neurodegeneration", *J. Neurosci.* 24(38):8237-8244 (Sep. 22, 2004).
Potrovita et al., "TWEAK—A Regulator of Neuronal Cell Death", *Naunyn-Schmiedeberg's Archives of Pharmacology* 369(Suppl. 1):R12, Abstr. 48 (Mar. 9, 2004).
Putterman et al., "Tweak Blockade Improves Kidney Disease in Lupus-Prone Mice: A Novel Approach to the Treatment of Lupus Nephritis?", Annual Meeting of Professional Research Scientists, Washington, D.C., Apr. 17-21, 2004. *FASEB J.*, 18(5), Experimental Biology 2004, Abstracts Part II:A839, Abstract No. 562.27 (2004).
Roberts et al., "Directed Evolution of a Protein: Selection of a Potent Neutrophil Elastase Inhibitors Displayed on M13 Fusion Phage", *Proc. Natl. Acad. Sci. USA* 89:2429-2433 (1992).
Romano et al., "Latest developments in gene transfer technology: achievements, perspectives, and controversies over therapeutic applications", *Stem Cells* 18:19-39 (2000).
Rosenberg et al., "Gene therapist, heal thyself", *Science* 287:1751 (2000).
Rovin et al., "Urine chemokines as biomarkers of human systemic lupus erythematosus activity", *J. Am. Soc. Nephrol.* 16:467-473 (2005).
Rubinsztein, "Lessons from animal models of Huntington's disease", *Trends Genet.* 18:202-209 (2002).
Rudikoff et al., "Single amino acid substitution altering antigen-binding specificity", *Proc. Natl. Acad. Sci. USA*, 79(6):1979-1983 (1982).
Rudinger, "Characteristics of the amino acids as components of a peptide hormone sequence", in *Peptide Hormones*. J.A. Parsons (Ed.), University Park Press, Baltimore, MD, 1976; pp. 1 and 6.
Rus et al., "Kinetics of Th1 and Th2 Cytokine Production During the Early Course of Acute and Chronic Murine Graft-Versus-Host Disease", *J. Immunol.* 155:2396-2406 (1995).
Ruuls et al., "The Length of Treatment Determines Whether IFN-Beta Prevents or Aggravates Experimental Autoimmune Encephalomyelitis in Lewis Rats", *J. Immunol.* 157:5721-5731 (1996).
Saas et al., "TWEAK Stimulation of Astrocytes and the Proinflammatory Consequences", *GLIA* 32(1):102-107 (2000).

Saemann et al., "Urinary tract infection in renal transplant recipients" *Eur. J. Clin. Invest.* 38(Suppl. 2):58-65 (2008).
Scamurra et al., "Ig heavy chain variable region VH3 family [*Homo sapiens*]", NCBI database Accession No. GI:33318898, GenBank Accession No. AAQ05352 (2002).
Schneider et al., "TWEAK Can Induce Cell Death via Endogenous TNF and TNF Receptor 1", *Eur. J. Immunol.* 29(6):1785-1792 (1999).
Semov et al., "Alterations in TNF- and IL-related Gene Expression in Space-flown WI38 Human Fibroblasts", *FASEB J.* 16(8):899-901 (2002).
Sharp et al., "The effect of peripheral nerve injury on disease progression in the $SOD^{1(G93A)}$ mouse model of amyotrophic lateral sclerosis", *Neuroscience* 130:897-910 (2005).
Shepard et al., "Monoclonal Antibody Therapy of Human Cancer: Taking the HER2 Protooncogene to the Clinic", *J. Clin. Immunol.* 11:117-127 (1991).
Smith et al., "CD30 Antigen, a Marker for Hodgkin's Lymphoma, is a Receptor Whose Ligand Defines an Emerging Family of Cytokines with Homology to TNF", *Cell* 73:1349-1360 (1993).
Somia et al., "Gene therapy: trials and tribulations", *Nature Reviews Genetics* 1:91-99 (2000).
Song et al., "A single amino acid change (Asp53→Ala53) converts Survivin from anti-apoptotic to pro-apoptotic", *Mol. Biol. Cell* 15:1287-1296 (Mar. 2004).
Steinman et al., "Virtues and Pitfalls of EAE for the Development of Therapies for Multiple Sclerosis", *Trends Immunol.* 26(11):565-571 (2005).
Steinman, L., "Optic Neuritis, a New Variant of Experimental Encephalomyelitis, a Durable Model for All Seasons, Now in Its Seventieth Year", *J. Exp. Med.* 197(9):1065-1071 (2003).
Storkebaum et al., "Treatment of motoneuron degeneration by intracerebroventricular delivery of VEGF in a rat model of ALS", *Nat. Neurosci.* 8:85-92 (2005).
Stryer et al., in *Biochemistry*, 3rd Ed., W.H. Freeman and Co.: New York, 1988; pp. 31-33.
Stuber et al., "The T Cell-B Cell Interaction via OX40-OX40L is Necessary for the T Cell-dependent Humoral Immune Response", *J. Exp. Med.* 183:979-989 (1996).
Sytwu et al., "The Roles of Fas/APO-1 (CD95) and Tnf in Antigen-Induced Programmed Cell Death in T Cell Receptor Transgenic Mice", *Immunity* 5:17-30 (1996).
Takagi et al, "Blockage of Interleukin-6 Receptor Ameliorates Joint Disease in Murine Collagen-Induced Arthritis", *Arthritis & Rheumatism* 41:2117-2121 (1998).
Tanabe et al., "Fibroblast growth factor-inducible-14 is induced in axotomized neurons and promotes neurite outgrowth", *J. Neurosci.* 23:9675-9686 (2003).
Tannenbaum et al., "The CXC Chemokines IP-10 and Mig are Necessary for IL-12-Mediated Regression of the Mouse RENCA Tumor", *J. Immunol.* 161:927-932 (1998).
Tartaglia et al., "The Two Different Receptors for Tumor Necrosis Factor Mediate Distinct Cellular Responses", *Proc. Natl. Acad. Sci. USA* 88:9292-9296 (1991).
Techman, A., "Biogen Idec and University of Adelaide Find TWEAK is a Novel Arthritogenic Mediator; Potential New Pathway in Rheumatoid Arthritis and Osteoarthritis Disease Process" *Muscukuloskeletal Report*, Aug. 16, 2006, pp. 1-2 [online]. Retrieved from the Internet, www.mskreport.com, Aug. 2, 2010.
Teng et al., "Functional recovery following traumatic spinal cord injury mediated by a unique polymer scaffold seeded with neural stem cells", *PNAS* 99:3024-3029 (2002).
Theien et al., "Discordant effects of anti-VLA-4 treatment before and after onset of relapsing experimental autoimmune encephalomyelitis", *J. Clin. Invest.* 107:995-1006 (2001).
Tibbetts et al., "Cardiac Antigen-Specific Autoantibody Production is Associated with Cardiomyopathy in *Trypanosoma cruzi*-Infected Mice", *J. Immunol.* 152:1493-1499 (1994).
Tomlinson et al., "The repertoire of human germline $V_H$ sequences reveals about fifty groups of $V_H$ segments with different hypervariable loops", *J. Mol. Biol.* 227:776-798 (1992).
Tomlinson et al., "The structural repertoire of the human Vκ domain" *EMBO J.* 14:4628-4638 (1995).

(56) References Cited

OTHER PUBLICATIONS

Toogood et al., "The Immune Response Following Small Bowel Transplantation", *Transplantation* 62(6):851-855 (1996).
Tran et al., "The Human Fn14 Receptor Gene is Up-Regulated in Migrating Glioma Cells in Vitro and Overexpressed in Advanced Glial Tumors", *Am. J. Pathol.* 162(4):1313-1321 (Apr. 2003).
Tran et al., "The Tumor Necrosis Factor-like Weak Inducer of Apoptosis (TWEAK)-Fibroblast Growth Factor-inducible 14 (Fn14) Signaling System Regulates Glioma Cell Survival via NFκB Pathway Activation and $BCL-X_{L\ /BCL-W\ Expression}$", *J. Biol. Chem.* 280(5):3483-3492 (Feb. 4, 2005).
Trauth et al., "Monoclonal Anitbody-Mediated Tumor Regression by Induction of Apoptosis", *Science* 245:301-305 (1989).
Trentham et al., "Autoimmunity to Type II Collagen: An Experimental Model of Arthritis", *J. Exp. Med.* 146:857-868 (1977).
U.S. Appl. No. 09/169,104 by Ashkenazi et al., filed Oct. 9, 1998.
U.S. Appl. No. 09/905,810 by Rennert, filed Jul. 13, 2001: Non-Final Office Action, mailed Aug. 27, 2002.
U.S. Appl. No. 09/905,810 by Rennert, filed Jul. 13, 2001: Non-Final Office Action, mailed May 21, 2003.
U.S. Appl. No. 09/905,810 by Rennert, filed Jul. 13, 2001: Final Office Action, mailed Feb. 11, 2004.
U.S. Appl. No. 10/510,804 by Burkly et al.: Final Office Action, Jan. 5, 2009.
U.S. Appl. No. 10/510,804 by Burkly et al.: Non-Final Office Action, Sep. 10, 2007.
U.S. Appl. No. 10/510,804 by Burkly et al.: Non-Final Office Action, Jul. 10, 2008.
U.S. Appl. No. 10/916,141 by Rennert: Final Office Action, Feb. 9, 2006.
U.S. Appl. No. 10/916,141 by Rennert: Notice of Allowance, Sep. 21, 2006.
U.S. Appl. No. 12/506,006 by Rennert: Final Office Action, mailed Feb. 3, 2011.
U.S. Appl. No. 12/506,006 by Rennert: Non-Final Office Action, mailed Aug. 9, 2010.
Uchiyama et al., "Tocilizumab, a Humanized Anti-interleukin-6 Receptor Antibody, Ameliorates Joint Swelling in Established Monkey Collagen-Induced Arthritis", *Biol. Pharm. Bull.* 31(6):1159-1163 (2008).
Verma et al., "Gene therapy—promises, problems and prospect", *Nature* 18:239-242 (1997).
Via "Advances in lupus stemming from the parent-into-F1 model", *Trends Immunol.* 31:236-245 (2010).
Via et al., "Role of cytotoxic T lymphocytes in the prevention of lupus-like disease occurring in a murine model of graft-vs-host disease", *J. Immunol.* 139:1840-1849 (1987).
Wada et al., "Detection of urinary interleukin-8 in glomerular diseases" *Kidney International* 46:455-460 (1994).
Wamil et al., "CM101-mediated recovery of walking ability in adult mice paralyzed by spinal cord injury", *Proc. Natl. Acad. Sci. USA* 95:13188-13193 (1998).
Ward et al., "Blocking of adhesion molecules in vivo as anti-inflammatory therapy", *Ther. Immunol.* 1(3):165-171 (1994).
*Webster's II New Riverside University Dictionary*, "Preventing", Boston, Mass.: Houghton Mifflin Co., 1994; p. 933.
Wiley et al., "A Novel TNF Receptor Family Member Binds TWEAK and is Implicated in Angiogenesis", *Immunity* 15:837-846 (2001).
Wiley et al., "Identification and Characterization of a New Member of the TNF Family that Induces Apoptosis", *Immunity* 3:673-682 (1995).
Wiley et al., "TWEAK, a member of the TNF superfamily, is a multifunctional cytokine that binds the TweakR/Fn14 receptor", *Cytokine & Growth Factor Reviews* 14:241-249 (2003).
Williamson et al., "IL-12 is a Central Mediator of Acute Graft-Versus-Host Disease in Mice", *J. Immunol.* 157(2):689-699 (1996).
Winkles et al., "Role of TWEAK and Fn14 in tumor biology", *Frontiers in Bioscience* 12:2761-2771 (Jan. 1, 2007).
Winkles et al., "TWEAK and Fn14: New molecular targets for cancer therapy?", *Cancer Letters* 235:11-17 (2006).
Wuthrich et al., "Autoimmune tubulointerstitial nephritis: insight from experimental models", *Exp. Nephrol.* 6(4):288-293 (1998).
Yepes et al., "A Soluble Fn14-Fc Decoy Receptor Reduces Infarct Volume in a Murine Model of Cerebral Ischemia", *Am. J. Pathol.* 166:511-520 (2005).
Yonehara et al., "A Cell-Killing Monoclonal Antibody (ANTI-Fas) to a Cell Surface Antigen Co-Downregulated with the Receptor of Tumor Necrosis Factor", *J. Exp. Med.* 169:1747-1756 (1989).
Zhang et al., "TWEAK-Fn14 pathway inhibition protects the integrity of the neurovascular unit during cerebral ischemia", *J. Cerebral Blood Flow & Metab.* 27:534-544 (2007).
Zhao et al., "Different Gene Expression Patterns in Invasive Lobular and Ductal Carcinomas of the Breast", *Mol. Biol. Cell* 15:2523-2536 (Jun. 2004).
Zhao et al., "TWEAK/Fn14 Interactions Are Instrumental in the Pathogenesis of Nephritis in the Chronic Graft-versus-Host Model of Systemic Lupus Erythematosis", *J. Immunol.* 179:7949-7958 (2007).
Zheng et al., "Post-ischemic inflammation: molecular mechanisms and therapeutic implications", *Neurol. Res.*, 26:884-892 (2004), Abstract only.
Zhu et al., "Inhibition of tumor growth and metastasis by targeting tumor-associated angiogenesis with antagonists to the receptors of vascular endothelial growth factor", *Investigational New Drugs* 17:195-212 (1999).
Zohar et al., "Closed-head minimal traumatic brain injury produces long-term cognitive deficits in mice", *Neuroscience* 118:949-955 (2003).
European Search Report issued in European Patent Application No. 08104327, dated Jan. 30, 2009 (13 pages).
U.S. Appl. No. 10/916,141 by Rennert: Non-Final Office Action, Jun. 15, 2005 (17 pages).
European Patent Application No. 06759489: Extended Search Report, including Search Opinion and Supplementary Search Report, dated Jul. 31, 2009.
European Patent Application No. 10181810: Partial Search Report, dated Mar. 19, 2012.
European Patent Application No. 11191771: Extended Search Report, including Search Opinion, dated Oct. 1, 2012.
European Patent Application No. 12171177: Extended Search Report, including Search Opinion, dated Mar. 1, 2013.
European Patent Application No. 12171177: Partial Search Report, dated Oct. 10, 2012.
European Patent Application No. 1 0181 061.2: Extended Search Report, including Search Opinion, dated Oct. 25, 2010.
European Patent Application No. 1 0181803: Partial Search Report, dated Mar. 19, 2012.
European Patent Application No. 1 0736488: Extended Search Report, including Search Opinion, dated Mar. 15, 2013.
International Search Report and Written Opinion in International Application No. PCT/US2014/059007, mailed Apr. 28, 2015, 26 pages.
International Search Report and Written Opinion issued in International Patent Application No. PCT/US06/005217; Date of Mailing: Aug. 4, 2006.
International Search Report and Written Opinion issued in International Patent Application No. PCT/US06/108077; Date of Mailing: Jul. 16, 2008.
International Search Report and Written Opinion issued in International Patent Application No. PCT/US07/81374; Date of Mailing: Mar. 17, 2008.
International Search Report issued in International Patent Application No. PCT/US01/28451; Date of Mailing: Mar. 11, 2002.
International Search Report issued in International Patent Application No. PCT/US97/13945; Date of Mailing: Jan. 7,1998.
International Search Report issued in International Patent Application No. PCT/US00/01044; Date of Mailing: Jun. 6, 2000.
International Search Report issued in International Patent Application No. PCT/US10/22610; Date of Mailing: Apr. 7, 2010.
Written Opinion issued in International Patent Application No. PCT/US00/01044; Date of Mailing: Oct. 30, 2000.

(56) References Cited

OTHER PUBLICATIONS

Written Opinion issued in International Patent Application No. PCT/US97/13945; Date of Mailing: Jul. 27, 1998.
Japanese Office Action issued in Japanese Patent Application No. 2008-511317, mailed Nov. 28, 2011.
[No Authors Listed], "Abetimus: Abetimus sodium, LJP 394" BioDrugs 17(3):212-215 (2003) (Abstract only).
Achiron et al., "Intravenus immunoglobulin treatment following the first demylinating event suggestive of multiple sclerosis", Arch. Neural. 61:1515-1520 (2004).
Agnello et al., "Increased peripheral benzodiazepine binding sites and pentraxin 3 expression in the spinal cord during EAE: relation to inflammatory cytokines and modulation by dexamethasone and rolipram" J. Neuroimmunol. 109:105-111 (2000).
Akahori et al., "Significance of TWEAK/Fn14 pathway in human pancreatic cancer," Proceedings of the Annual Meeting of the American Assoc. for Cancer Research 47: 1346, Abstract 5724.
Alarcon-Segovia et aI., "LJP 394 for the Prevention of Renal Flare in Patients With Systemic Lupus Erythematosus" Arthritis & Rheumatism 48(2):442-454 (2003).
Almagro et al., "Humanization of Antibodies," Frontiers in BioScience, 13:1619-1633 (Jan. 2008).
Anonymous: "NCT01499355 on Sep. 13, 2013: ClinicalTrials.gov Archive," Sep. 13, 2013, Retrieved from the Internet: URL:https://clinicaltrials.gov/archive/nct/01499355/2013_09_13 [retrieved on Jan. 19, 2015], 6 pages.
Anonymous: "NCT01930890 on Sep. 13, 2013: ClinicalTrials.gov Archive," Sep. 13, 2013, Retrieved from the Internet: URL:https://clinicaltrials.gov/archive/nct/01930890/2013_09_13 [retrieved on Jan. 19, 2015], 5 pages.
Anonymous: "NCT01943513 on Sep. 16, 2013: ClinicalTrials.gov Archive," Sep. 16, 2013, Retrieved from the Internet: URL:https://clinicaltrials.gov/archive/nct/01943513/2013_09_16 [retrieved on Jan. 19, 2015], 5 pages.
Banati et al., "The peripheral benzodiazepine binding site in the brain in multiple sclerosis: quantitative in vivo imaging of microglia as a measure of disease activity," Brain 123:2321-2337 (2000).
Bonaldo et al., "Cellular and molecular mechanisms of muscle atrophy," Disease Models & Mechanisms 6(1):25-39 (Dec. 24, 2012).
Buatois et al., "Pan-CC Chemokine Neutralization Restricts Splenocyte Egress and Reduces Inflammation in a Model of Arthritis," J. Immunol 185:2544-2554 (2010).
Burkly et al, "TWEAKing tissue remodeling by a multifunctional cytokine: role of TWEAK/Fn•14 pathway in health and disease", Cytokine 40:1-16 (2007).
Byrne et al., "An Antibody to IP-1 0 Is a Potent Antagonist of Cell Migration In Vitro and In Vivo and Does Not Affect Disease in Several Animal Models of Inflammation," Autoimmunity 42(3):171-182 (2009).
Cardiel et al., "Abetimus Sodium for Renal Flare in Systemic Lupus Erythematosus" Arthritis & Rheumatism 58(8):2470-2480 (2008).
Colman, P.M., "Effects of amino acid sequence changes on antibody-antigen interactions," Res. Immunol 145(1):33-36 (1994).
Comi et al. "European/Canadian multicenter, double-blind, randomized, placebo-controlled study of the effects of glatiramer acetate on magnetic resonance imaging-measured disease activity and burden in patients with relapsing multiple sclerosis," Ann. Neurol. 49: 290-297 (2001).
Debruyne et al., "PET visualization of microglia in multiple sclerosis patients using [11C]PK11195" Eur. J. Neurol. 10:257-264 (2003).
Dogra et al., "TNF-related weak inducer of apoptosis (TWEAK) is a potent skeletal muscle wasting cytokine", FASEB J. 21: 1857-i 869 (2007).
Dohi et al., "TWEAK/Fn14 Pathway: A Nonredundant Role in Intestinal Damage in Mice Through a TWEAK/Intestinal Epithelial Cell Axis" *Gastroenterology* 136(3):912-923 (2009). EPub. Nov. 8, 2008.

Eley et al., "Effect of branched-chain amino acids on muscle atrophy in cancer cachexia," Biochem J., 407(1):113-120 (Oct. 1, 2007).
Ferrara et al., "The Biology of Vascular Endothelial Growth Factor," Endocr. Rev. 18(1):4-25 (1997).
Gavish et al., "Enigma of the Peripheral Benzodiazepine Receptor", Pharmacological Reviews 51(4):629-650 (1999).
Gilgun-Sherki et al., "Analysis of Gene Expression in MOG-Induced Experimental AutoimmuneEncephalomyelitis After Treatment with a Novel Brain-Penetrating Antioxidant" J. Mo/. Neurosci. 27(1):125-136 (2005).
Girgenrath et al., TWEAK, via its receptor Fn14, is a novel regulator of mesenchymal progenitor cells and skeletal muscle regeneration, EMEJO J 25:5826--5839 (2006).
Hao et al., "Beta-cell differentiation from nonendocrine epithelial cells of the adult human pancreas," Nature Medicine, 2006, 12(3):310-316.
Harrison's Principles of Internal Medicine, 2005; pp. 1960-1963.
Hill et al., "Outcome of relapse in lupus nephritis: Roles od reversal of renal fibrosis and response of inflammation to therapy," Kidney Int'l., 2002, 61:2176-2186.
Houssiau et al., "Immunosuppressive therapy in lupus nephritis: The Euro-Lupus Nephritis Trial, a randomized trial of low-dose versus high-dose intravenous cyclophosphamide," Arthritis & Rheumatism, 46(8):2121-2131 (Aug. 1, 2002).
Ibrahim, S. et al., "Gene Expression Profiling of the Nervous System in Murine Experimental Autoimmune Encephalomyelitis" Brain 124(10): 1927-1938 (2001).
Jones et al., "Immunospecific reduction of antioligonucleotide antibody-forming cells with a tetrakis-oligonucleotide conjugate (LJP 394), a therapeutic candidate for the treatment of lupus nephritis" J. Med. Chem. 38(12):2138-2144 (1995) (Abstract only).
Kang et al., "The Influence of a Polymorphism at Position −857 of the Tumour Necrosis Factor Alpha Gene on Clinical Response to Etanercept Therapy in Rheumatoid Arthritis", Rheumatology 44(4):547-552 (2005).
Kawabata et al., "Kansetsu ryumachi no aratana yakubutsu ryouhou heno tenbou", Yakuji 47(3):49-53 (2005) (Japanese).
Khalaileh et al., "Determinants of pancreatic beta-cell regeneration," Diabetes Obes Metab., 2008, 10(54):128-135.
Knappik et al., "Fully Synthetic Human Combinatorial Antibody Libraries (HuCAL) Based on Modular Consensus Frameworks and CDRs Randomized with Trinucleotides", J. Mol. Biol. 296(1):57-86 (2000).
Kogan et al., "A Single Amino Acid Residue Can Determine the Ligand Specificity of E-selectin," J Biol. Chem. 270:14047-14055 (1995).
Kurtzke, J.F., "Clinical Definition for Multiple Sclerosis Treatment Trials", Ann. Neural. 36:S73-S79 (1994).
Kurtzke, J.F., "Rating neurologic impairment in multiple sclerosis: An expanded disability status scale (EDSS)", Neurology 33:1444-1452 (1983).
Lantto et al., "Functional Consequences of Insertions and Deletions in the Complementarity-determining Regions of Human Antibodies", J. Biol. Chem. 277(47):45108-45.114 (2002).
Lee et al., "Regeneration of Pancreatic Islets After Partial Pancreatectomy in Mice Does Not Involve the Reactivation of Neurogenin-3" Diabetes 55:269-272 (2006).
Lipsky et al., "Infliximab and Methotrexate in the Treatment of Rheumatoid Arthritis", N. Engl. J. Med. 343(22): 1594-1602 (2000).
Ljung et al., "Infliximab in inflammatory bowel disease: clinical outcome in a population based cohort from Stockholm County", Gut 53:849-853 (2004).
Mattner et al. "Evaluation of radiolabelled peripheral benzodiazepine receptor ligand in the central nervous system inflammation of experimental autoimmune encephalomyelitis: a possible role for imaging multiple sclerosis," Eur. J Nucl. Med. Mol. Imaging 32:557-563 (2005).
Michaelson et al., "Role of TWEAK in lupus nephritis: A bench-to-bedside review," J Autoimmunity, 39(3):130-142 (Sep. 1, 2012).

(56) References Cited

OTHER PUBLICATIONS

Mittal et al., "The TWEAK-Fn14 system is a critical regulator of denervation-induced skeletal muscle atrophy in mice", J. Cell Biol., 188(6):833-849 (2009).
Mohler et al., "Nonsteroidal tissue selective androgen receptor modulators: a promising class of clinical candidates," Expert Opin Therapeutic Patents 15(11):1565-1585 (Nov. 1, 2005).
Morosetti et al., "TWEAK in Inclusion-Body Myositis Muscle—Possible Pathogenic Role of a Cytokine Inhibiting Myogenesis", Am. J. Pathol. 180(4): 1603-1613 (2012).
Nakaya et al., "Regulation of Asialoglycoprotein Receptor Synthesis by Inflammation-Related Cytokines in HepG2 Cells," J. Gastroenterol. 29:24-30 (1994).
Nir et al., "Recovery from diabetes in mice by beta cell regeneration," J Clin Invest., 2007, 117(9):2553-2561.
Paul et al., "The E3 Ubiquitin Ligase TRAF6 Intercedes in Starvation-Induced Skeletal Muscle Atrophy through Multiple Mechanisms", Mol. Cell. Bioi. 32(7):1248-1259 (2012).
Paul, "Fv Structure and Diversity in Three Dimensions", in Fundamental Immunology, 3rd. edition. New York: Raven Press, 1993; pp. 292-295.
Pavco et al., "Antitumor and Antimetastatic Activity of Ribozymes Targeting the Messenger RNA of Vascular Endothelial Growth Factor Receptors," Clin. Cancer Res. 6:2094-2103 (2000).
Poser et al., "New Diagnostic Criteria for Multiple Sclerosis: Guidelines for Research Protocols", Ann. Neural. 13:227-231 (1983).
Rivas-Carrillo et al., "Pancreas development and β-cell differentiation of embryonic stem cells," Curr Med Chem., 2007, 14(14):1573-1578.
Rizvi et al. "Current approved options for treating patients with multiple sclerosis", Neural. 63 (Suppl .6): S8-S14 (2004).
Salloum et al., "NM-3, an isocoumarin, increases the antitumor effects of radiotherapy without toxicity," Cancer Res. 60(24)6958-6963 (2000).
Schakman et al., "Glucocorticoid-induced skeletal muscle atrophy," Int'l J Biochem Cell Biol., 45(10):2163-2172 (Jun. 24, 2013).
Schonohoff et al., "Neurogenin 3-expressing progenitor cells in the gastrointestinal tract differentiate into both endocrine and nonendocrine cell types," Dev Biol., 2004, 270(2):443-454.
Shaw et al., "Preferential transformation of human neuronal cells by human adenoviruses and the origin of HEK 293 cells," FASEB J. 16(8):869-871 (Jun. 2002); electronically published Apr. 10, 2002.
Smith, M.D., "Etanercept Treatment of Rheumatoid Arthritis in the 'Real World'", Ann. Rheum. Dis. 62(1):95-96 (2003).
Sobel et al., "The Immunopathology of Experimental Allergic Encephalomyelitis", J. Immunol. 132:2393-2401 (1984).
Sundaram et al. Chapter 102 Monoclonal Antibodies and Their Engineered Fragments. The Biomedical Engineering Handbook; Second Edition vol. 112000; CRC PRESS LLC, pp. 102-1-102-20 (2000).
Tozawa et al., "Atarashii TNF Sogaizai (New TNF inhibitor)" G./. Research 13(1):25-33 (2005) (Japanese).
Traugott, "Detailed Analysis of Early Immunopathologic Events during Lesion Formation in Acute Experimental Autoimmune Encephalomyelitis", Cell Immunol. 119:114-129 (1989).
Tschetter et al., "Progression from acute to chronic disease in a murine parent-into-F1 model of graft-versus-host disease," J Immunol., Nov. 2000, 165(10):5987-94.
Tuohy et al., "A Synthetic Peptide from Myelin Proteolipd Protein Induces Experimental Allergic Encephalomyelitis," J. Immunol. ,1988, 141:1126-1130.
U.S. Appl. No. 11/422,191 by Browning, et al., filed Jun. 5, 2006.
U.S. Patent Interference No. 105,513 entered on Nov. 15, 2006.
U.S. Patent Interference No. 105,513, Paper 106, Memorandum Opinion and Order, Decision on Motions.
U.S. Patent Interference No. 105,513, Paper 107, Decision—Bd. R. 125, Decision on Browning Misc. Motion 4 for Sanctions.
U.S. Patent Interference No. 105,513, Paper 108, Judgment, Preliminary Motions—Bd. R. 127.
Veenman et al., "Peripheral-type benzodiazepine receptors: their implication in brain disease," Drug Dev. Res., 2000, 50:355-370.
Vowinckel et al., "PK11195 binding to the peripheral benzokiazepine receptor as a marker of microglia activation in multiple sclerosis and experimental autoimmune encephalomyelitis," J. Nueroscience. Res., 1997, 50:345-353.
Weening et al., "The classification of Glomerulonephritis in Systemic Lupus Erythematosus Revisited," J Am Soc Nephrol., 15:241-250 (Jan. 1, 2004).
Weisman et al., "Reduction in circulating dsDNA antibody titer after administration of LJP 394" J. Rheumatol. 24(2):314-318 (1997) (Abstract only).
Wells, J.A. Additivity of Mutational Effects in Proteins. Biochemistry 29:8509-8517 (1990).
Williams et al., "Anti-tumor necrosis factor ameliorates joint disease in murine collagen-induced arthritis" Proc. Natl. Acad. Sci. USA 89:9784-9788 (1992).
Wisniacki et al., "2201—A Phase I, Randomized, Double-Blind, Placebo-Controlled, Single-Dose, Dose Escalation Study to Evaluate the Safety, Tolerability and Pharmacokinetics of BIIB023 (Anti-TWEAK) in Subjects with Rheumatoid Arthritis," 2011 ACR/ARHP Annual Scientific Meetings, Nov. 8, 2011, abstract.
Wisniacki et al., "A Phase I Randomized, Double-Blind, Placebo-Controlled, Single-Dose, Dose Escalation Study to Evaluate the Safety, Tolerability and Pharmacokinetics of BIIB023 (Anti-TWEAK) in Subjects with Rheumatoid Arthritis," Arthritis & Rheumatism, p. 2201 (Jan. 1, 2011).
Wolinsky, "Glatiramer acetate for the treatment of multiple sclerosis," Expert Opin. Pharmacother., 2004, 5(4):875-891.
Wu et al., "The Impact of Muscle Disuse on Muscle Atrophy in Severely Burned Rats," J Surgical Res., 164(2):e243-e251 (Dec. 1, 2010).
Yap et al., "Long-term data on corticosteroids and mycophenolate mofetil treatment in lupus nephritis," Rheumatol., 52(3):480-486 (Nov. 12, 2012).
Biancone et al., "Inhibition of the CD40-CD40ligand Pathway Prevents Murine Membranous Glomerulonephritis," Kidney International 48:458-468 (Aug. 1995).
Crowe et al., "A Lymphotoxin-beta-Specific Receptor," Science 264:707-710 (Apr. 1994).
De Togni et al., "Abnormal Development of Peripheral Lymphoid Organs in Mice deficient in Lymphotoxin," Science 264:703-707 (Apr. 1994).
Goeddel et al., "Tumor Necrosis Factors: Gene Structure and Biological Activities," Cold Spring Harbor Symposia on Quantitative Biology L1:597-609 (Jan. 1986).
Goodwin et al., "Molecular and Biological Characterization of a Ligand for CD27 Defines a New Family of Cytokines with Homology to Tumor Necrosis Factor," Cell 73:447-456 (May 1993).
Goodwin et al., "Molecular Cloning of a Ligand for the Inducible T Cell Gene 4-1BB: A Member of an Emerging Family of Cytokines with Homology to Tumor Necrosis Factor," Eur. J. Immunol. 23:2631-2641 (Oct. 1993).
Grau et al., "TNF and Mycobacteria," in Tumor Necrosis Factors. The Molecules and Their Emerging Role in Medicine, B. Beutler (Ed.), Raven Press, NY, pp. 329-340 (1992).
Hu et al., "Characterization of TNFRSF19, a novel member of the tumor necrosis factor receptor superfamily," Genomics. 62(1):103-7 (Nov. 1999).
International Preliminary Examination Report in International Application No. PCT/US00/01044, Mar. 13, 2001, 8 pages.
International Search Report in International Application No. PCT/US06/19706, dated Oct. 9, 2007, 4 pages.
Jones et al., Structure of Tumor Necrosis Factor, Nature 338-225-228 (Mar. 1989).
Kitson et al., "A Death-Domain-Containing Receptor that Mediates Apoptosis," Nature 384:372-375.
Kriegler et al., "A Novel Form of TNF/Cachectin is a Cell Surface Cytotoxic Transmembrane Protein: Ramifications for the Complex Physiology of TNF," Cell 53:45-53 (Apr. 1988).
Laucat et al., "Mutations in Fas Associated with Human Lymphoproliferative Syndrome and Autoimmunity" Science 268:1347-1349 (Jun. 1995).

(56) References Cited

OTHER PUBLICATIONS

Lazar et al., "Transforming growth factor alpha: mutation of aspartic acid 47 and leucine 48 results indifferent biological activities" Mol. Cell. Biol. 8:1247-1252 (Mar. 1988).

Loetscher et al., "Molecular Cloning and Expression of the Human 55 kd Tumor Necrosis Factor Receptor," Cell 61:351-359 (Apr. 1990).

Luettig et al., "Evidence for the Existence of Two Forms of membrane Tumor Necrosis Factor: An Integral protein and a Molecule Attached to Its Receptor," Journal of Immunology 143:4034-4038 (Dec. 1987).

Malik, "The Activity of TNF in Experimental Cancer Models," in Tumor Necrosis Factors. The Molecules and Their Emerging Role in Medicine, B. Beutler (Ed.), Raven Press, NY, pp. 407-423 (1992).

Nakane, "TNF in Listeriosis," in Tumor Necrosis Factors. The Molecules and their Emerging Role in Medicine, B. Beutler (Ed.), Raven Press, NY, pp. 285-292 (1992).

Piguet "TNF and Alloreactions. Involvement of TNF in the Effector Phase of Graft-Versus-Host and Host-Versus Graft Reactions" in Tumor Necrosis Factors. The Molecules and Their Emerging Role in Medicine, B. Beutler, Raven Press, NY, pp. 341-354.

Roodman, "TNF and Hematopoiesis" In Tumor Necrosis Factors. The Molecules and Their Emerging Role in Medicine, B. Beutler (Ed.), Raven Press, NY, pp. 117-129 (1992).

Ruby et al., "CD40 Ligand Has Potent Antiviral Activity" Nature Medicine 1:437-441 (May 1995).

Schall et al., "Molecular Cloning and Expression of a Receptor for Human Tumor Necrosis Factor" Cell 61:361-370 (Apr. 1990).

Scott & George, "Searching for Peptide Ligands with and Epitope Library" Science 249:386-390 (Jul. 1990).

Smith et al., "A Receptor for Tumor Necrosis Factor Defines an Unusual Family of Cellular and Viral Proteins," Science 248:1019-1021 (May 1990).

Smith et al., "The TNF Receptor Superfamily of Cellular and Viral Proteins: Activation, Costimulation, and Death," Cell 76:959-962 (1994).

Stancovski et al., "Mechanistic aspects of the opposing effects of monoclonal antibodies to the ERBB2 receptor on tumor growth," PNAS 88:8691-8695 (Oct. 1991).

Takahashi et al., "Generalized Lymphoproliferative Disease in Mice Caused by a Point Mutation in the Fas Ligand," Cell 76:969-976 (Mar. 1994).

Tartaglia et al., "Two TNF Receptors," Immunology Today 13:151-153 (Jan. 1992).

Tracey, "The Acute and Chronic Pathophysiologic Effects of TNF: Mediation of Septic Shock and Wasting (Cachexiz)," in Tumor Necrosis Factors. The Molecules and their Emerging Role in Medicine, B. Beulter (Ed.)., Raven Press, NY, pp. 255-273 (1992).

Waage, "Presence and Involvement of TNF in Septic Shock," in Tumor Necrosis Factors. The Molecules and their Emerging Role in Medicine, B. Beutler (Ed.), Raven Press, NY, pp. 276-283 (1992).

Wong et al., "MnSOD Induction by TNF and Its Protective Role," in Tumor Necrosis Factors. The Molecules and Their Emerging Role in Medicine, B. Beutler (Ed.), Raven Press, NY, pp. 473-484 (1992).

Zheng et al., "Induction of Apoptosis in Mature T Cells by Tumor Necrosis Factor," nature 377:348-351 (Sep. 1995).

Zips et al., "New Anticancer Agents: In Vitro and In Vivo Evaluation," In Vivo 19:1-7 (Jan. 2005).

Bowerman et al., "Tweak regulates astrogliosis, microgliosis and skeletal muscle atrophy in a mouse model of amyotrophic lateral sclerosis," Human Molecular Genetics 24(12): 3440-3456 (2015).

Foy et al., "Immune Regulation by CD40 and Its Ligand GP39," Annu. Rev. Immunol. 14: 591-617 (1996).

Holecek et al., "Muscle wasting in animal models of severe illness," Int J Exp Path., 93:157-171 (2012).

Sienkiewicz et al., "Duchenne muscular dystrophy: current cell therapies," Therapeutic Advances in Neurological disorder 8(4); 166-177 (2015).

Vassalli "The Pathophysiology of Tumor Necrosis Factors," Annu. Ret. Immunol. 10:411-52 (1992).

Yadava et al., "TWEAK/Fn14, a pathway and novel therapeutic target in myotonic dystrophy," Human Molecular Genetics, 24(7): 2035-2048 (Apr. 2015).

\* cited by examiner

SEQUENCE LISTING

<160> NUMBER OF SEQ ID NOS: 2

<210> SEQ ID NO 1
<211> LENGTH: 249
<212> TYPE: PRT
<213> ORGANISM: Homo sapiens

<400> SEQUENCE: 1

```
Met Ala Ala Arg Arg Ser Gln Arg Arg Gly Arg Arg Gly Glu Pro
1               5                   10                  15

Gly Thr Ala Leu Leu Val Pro Leu Ala Leu Gly Leu Gly Ala Leu
                20                  25                  30

Ala Cys Leu Gly Leu Leu Leu Ala Val Val Ser Leu Gly Ser Arg Ala
            35                  40                  45

Ser Leu Ser Ala Gln Glu Pro Ala Gln Glu Glu Leu Val Ala Glu Glu
        50                  55                  60

Asp Gln Asp Pro Ser Glu Leu Asn Pro Gln Thr Glu Glu Ser Gln Asp
65                  70                  75                  80

Pro Ala Pro Phe Leu Asn Arg Leu Val Arg Pro Arg Arg Ser Ala Pro
                85                  90                  95

Lys Gly Arg Lys Thr Arg Ala Arg Arg Ala Ile Ala Ala His Tyr Glu
            100                 105                 110

Val His Pro Arg Pro Gly Gln Asp Gly Ala Gln Ala Gly Val Asp Gly
        115                 120                 125

Thr Val Ser Gly Trp Glu Glu Ala Arg Ile Asn Ser Ser Ser Pro Leu
    130                 135                 140

Arg Tyr Asn Arg Gln Ile Gly Glu Phe Thr Val Ile Arg Ala Gly Leu
145                 150                 155                 160

Tyr Tyr Leu Tyr Cys Gln Val His Phe Asp Glu Gly Lys Ala Val Tyr
                165                 170                 175

Leu Lys Leu Asp Leu Leu Val Asp Gly Val Leu Ala Leu Arg Cys Leu
            180                 185                 190

Glu Glu Phe Ser Ala Thr Ala Ala Ser Ser Leu Gly Pro Gln Leu Arg
        195                 200                 205

Leu Cys Gln Val Ser Gly Leu Leu Ala Leu Arg Pro Gly Ser Ser Leu
    210                 215                 220

Arg Ile Arg Thr Leu Pro Trp Ala His Leu Lys Ala Ala Pro Phe Leu
```

-continued

```
                225                 230                 235                 240
Thr Tyr Phe Gly Leu Phe Gln Val His
                245

<210> SEQ ID NO 2
<211> LENGTH: 129
<212> TYPE: PRT
<213> ORGANISM: Homo sapiens

<400> SEQUENCE: 2

Met Ala Arg Gly Ser Leu Arg Arg Leu Leu Arg Leu Val Leu Gly
1               5                   10                  15

Leu Trp Leu Ala Leu Leu Arg Ser Val Ala Gly Glu Gln Ala Pro Gly
                20                  25                  30

Thr Ala Pro Cys Ser Arg Gly Ser Ser Trp Ser Ala Asp Leu Asp Lys
                35                  40                  45

Cys Met Asp Cys Ala Ser Cys Arg Ala Arg Pro His Ser Asp Phe Cys
            50                  55                  60

Leu Gly Cys Ala Ala Ala Pro Pro Ala Pro Phe Arg Leu Leu Trp Pro
65                  70                  75                  80

Ile Leu Gly Gly Ala Leu Ser Leu Thr Phe Val Leu Gly Leu Leu Ser
                85                  90                  95

Gly Phe Leu Val Trp Arg Arg Cys Arg Arg Glu Lys Phe Thr Thr
                100                 105                 110

Pro Ile Glu Glu Thr Gly Gly Glu Gly Cys Pro Ala Val Ala Leu Ile
            115                 120                 125

Gln
```

TREATING NEUROLOGICAL DISORDERS

CROSS-REFERENCE TO RELATED APPLICATIONS

This is a division of U.S. application Ser.No. 13/222,097, filed Aug. 31, 2011 (abandoned), which is a Continuation of U.S. application Ser. No. 11/816,502, filed Oct. 3, 2008 (abandoned), which is a National Phase entry of PCT/US2006/005597 filed Feb. 17, 2006, which claims the benefit of U.S. Provisional Application No. 60/653,813filed Feb. 17, 2005, all of which are incorporated herein in their entirety by reference.

SEQUENCE LISTING

The instant application contains a sequence listing which has been submitted in ASCII format via EFS-Web and is hereby incorporated by reference in its entirety.

BACKGROUND

Neurological disorders affect an estimated 50 million Americans each year, exacting an incalculable personal toll and an annual economic cost of hundreds of billions of dollars in medical expenses and lost productivity.

SUMMARY

TWEAK (TNT-like weak inducer of apoptosis) is a trimeric protein that is a TNF (Tumor Necrosis Factor) superfamily member. TWEAK mediates cellular responses by activating a cell surface receptor (referred to as a TWEAK receptor or TWEAK-R herein), such as the Fn14 protein. As further described below, blocking TWEAK/TWEAK-R interaction or activity is an effective and useful therapy for neuronal injury or pathology, e.g., in the CNS or peripheral nervous system. The therapy can be used to treat neuronal disorders such as mechanical neuronal traumas and neurodegenerative disorders. Examples of mechanical neuronal traumas include spinal cord injury (SCI) and traumatic brain injury (TBI). Examples of neurodegenerative disorders include amyotrophic lateral sclerosis (ALS), progressive bulbar palsy (PBP), primary lateral sclerosis (PLS), progressive muscular atrophy (PMA), Parkinson's Disease, Huntington's Disease (HD), and Alzheimer's Disease.

A variety of TWEAK and/or TWEAK receptor blocking agents can be administered to a subject to block a TWEAK/TWEAK-R interaction or activity. A "TWEAK/TWEAK-R blocking agent" or "agent that blocks a TWEAK/TWEAK-R interaction or activity" refers to an agent (e.g., any compound, e.g., an antibody or a soluble form of the TWEAK receptor) that at least partially inhibits an interaction or activity of a TWEAK or TWEAK receptor. For example, the agent at least partially inhibits an activity, e.g., binding of TWEAK to a TWEAK receptor, or the agent at least partially inhibits a nucleic acid encoding TWEAK or TWEAK receptor, e.g., to reduce TWEAK or TWEAK receptor protein expression.

In one embodiment, the agent reduces the ability of TWEAK to bind to Fn14 (a TWEAK receptor). The agent can be an antibody that binds to TWEAK or to Fn14, The antibody can be a full length IgG. In one embodiment, the antibody is human, humanized, or effectively human.

In one embodiment, the agent is a soluble loin of a TWEAK receptor, e.g., a human TWEAK receptor such as Fn14. The soluble form of the TWEAK receptor can be fused to an antibody Fc region (e.g., a human Fc region). For example, the soluble form of the TWEAK receptor includes a sequence at least 95% identical to amino acids 28-$X_1$ of SEQ ID NO:2, where amino acid $X_1$ is selected from the group of residues 68 to 80 of SEQ ID NO:2.

In one embodiment, a primary characteristic of the neuronal disorder is not demyelination or the presence of autoantibodies against myelin.

In one embodiment, the neuronal disorder is primarily characterized by in destruction or death of nerve cells, e.g., of motor neurons (e.g., ALS), of striatal neurons of basal ganglia and/or cortical neurons (e.g., Huntington's disease), of substantia nigra neurons (e.g., Parkinson's disease).

In one aspect, the disclosure features a method of treating spinal cord injury (SCI). The method includes administering a TWEAK/TWEAK-R blocking agent to a subject who has experienced or is at risk of experiencing a spinal cord injury, e.g., within the previous 48, 24, 12, or 6 hours. The agent can be administered in an amount and/or for a time to ameliorate at least one symptom of SCI, to reduce neuronal damage associated with SCI, and/or to reduce inflammation associated with SCI. The agent can be administered in combination with another treatment for a spinal cord injury, e.g., administering corticosteroids such as methylprednisolone or stabilization of the vertebrae of the spine. Further, the method can include evaluating the subject using a spinal cord injury assessment criterion, such as the American Spinal Injury Association assessment criteria and/or by performing a neurological exam. The method can include a step of identifying a subject who has sustained or is at risk of sustaining a spinal cord injury, e.g., detecting a spinal cord injury in a subject. A TWEAK/TWEAK-R blocking agent can be packaged in a container that has a label with instructions for use of the agent in treating a spinal cord injury. The disclosure also features an agent that blocks a TWEAK/TWEAK-R interaction or activity for use in treating a spinal cord injury and for the manufacture of a medicament for treating a spinal cord injury.

In one aspect, the disclosure features a method of treating traumatic brain injury (TBI). The method includes administering a TWEAK/TWEAK-R blocking agent to a subject who has sustained or experienced, or is at risk of experiencing or sustaining, a traumatic brain injury, e.g., within the previous 48, 24, 12, or 6 hours. The agent can be administered in an amount and/or for a time to ameliorate at least one symptom of TBI, to reduce neuronal damage associated with TBI, and/or to reduce inflammation associated with TBI. The agent can be administered in combination with another treatment for a traumatic brain injury, e.g., surgery to control bleeding in and around the brain, monitoring and controlling intracranial pressure, insuring adequate blood flow to the brain, or treating the body for other injuries and infection. Further, the method can include evaluating the subject using a traumatic brain injury assessment criterion, such as the Glasgow Coma Scale. The method can include a step of identifying a subject who has sustained or is at risk of sustaining a traumatic brain injury, e.g., by detecting a recent traumatic brain injury in a subject. A TWEAK/TWEAK-R blocking agent can be packaged in a container that has a label with instructions for use of the agent in treating a traumatic brain injury. The disclosure also features an agent that blocks a TWEAK/TWEAK-R interaction or activity for use in treating a traumatic brain injury or for the manufacture of a medicament for treating a traumatic brain injury.

In addition to therapeutic use in treating SCI and TBI, a TWEAK/TWEAK-R blocking agent can be used to treat other trauma to the central or peripheral nervous system, particularly mechanical trauma to the central nervous system. The treatment may also include a prophylactic component. For example, the blocking agent may be administered (locally or systemically) prior to, during, or after surgery, e.g., surgery that requires intervention in or near the central nervous system. In the case of unexpected traumas, it is frequently desirable to provide the blocking agent as soon as possible after the trauma event, e.g., within the previous 48, 24, 12, or 6 hours since the event. The blocking agent can also be used when grafting or implanting neuronal tissue (e.g., in a xeno-transplant, etc).

In one aspect, the disclosure features a method of treating amyotrophic lateral sclerosis (ALS). The method includes administering a TWEAK/TWEAK-R blocking agent to a subject who has or has been diagnosed as having symptoms of ALS or a predisposition to developing ALS. The agent can be administered in an amount and/or for a time to ameliorate at least one symptom of ALS, to reduce neuronal damage associated with ALS, and/or to reduce inflammation associated with ALS. The agent can be administered in combination with another treatment for ALS, e.g., riluzole. Further, the method can include evaluating the subject using an ALS assessment criterion, such as the Appel ALS Rating Scale. The method can include a step of identifying a subject who has ALS, e.g., detecting ALS in a subject. A TWEAK/TWEAK-R blocking agent can be packaged in a container that has a label with instructions for use of the agent in treating ALS. The disclosure also features an agent that blocks a TWEAK/TWEAK-R interaction or activity for use in treating ALS and for the manufacture of a medicament for treating ALS.

In one aspect, the disclosure features a method of treating Parkinson's Disease. The method includes administering a TWEAK/TWEAK-R blocking agent to a subject who has or has been diagnosed as having symptoms of Parkinson's Disease or a predisposition to developing Parkinson's Disease. The agent can be administered in an amount and/or for a time to ameliorate at least one symptom of Parkinson's Disease, to reduce neuronal damage associated with Parkinson's Disease, and/or to reduce inflammation associated with Parkinson's Disease. The agent can be administered in combination with another treatment for Parkinson's Disease, e.g., levodopa and the dopamine agonists ropinirole, pramipexole, and pergolide, MAO-B inhibitors (e.g., R(+)—N-propargyl-1-aminoindan). Further, the method can include evaluating the subject using a Parkinson's Disease assessment criterion, such as the Hoehn and Yahr Staging of Parkinson's Disease; the Schwab and England Activities of Daily Living assessment; or the Unified Parkinson's Disease Rating Scale. The method can include a step of identifying a subject who has Parkinson's Disease, e.g., detecting Parkinson's Disease in a subject, A TWEAK/TWEAK-R blocking agent can be packaged in a container that has a label with instructions for use of the agent in treating Parkinson's Disease. The disclosure also features an agent that blocks a TWEAK/TWEAK-R interaction or activity for use in treating Parkinson's Disease and for the manufacture of a medicament for treating Parkinson's Disease.

In one aspect, the disclosure features a method of treating Huntington's Disease. The method includes administering a TWEAK/TWEAK-R blocking agent to a subject who has or has been diagnosed as having symptoms of Huntington's Disease or a predisposition to developing Huntington's Disease. The agent can be administered in an amount and/or for a time to ameliorate at least one symptom of Huntington's Disease, to reduce neuronal damage associated with Huntington's Disease, and/or to reduce inflammation associated with Huntington's Disease. The agent can be administered in combination with another treatment for Huntington's Disease, e.g., bromocriptine, serotonin antagonists (e.g., tetrabenazin), tiapride (e.g., TIAPRIDAL®), or a NMDA receptor blocker. Further, the method can include evaluating the subject using a Huntington's Disease function assessment criterion, such as the Unified Huntington's Disease Rating Scale (UNDRS). The method can include a step of identifying a subject who has Huntington's Disease, e.g., detecting Huntington's Disease in a subject. A TWEAK/TWEAK-R blocking agent can be packaged in a container that has a label with instructions for use of the agent in treating Huntington's Disease. The disclosure also features an agent that blocks a TWEAK/TWEAK-R interaction or activity for use in treating Huntington's Disease and for the manufacture of a medicament for treating Huntington's Disease.

In one aspect, the disclosure features a method of treating Alzheimer's Disease. The method includes administering a TWEAK/TWEAK-R blocking agent to a subject who has or has been diagnosed as having symptoms of Alzheimer's Disease or a predisposition to developing Alzheimer's Disease. The agent can be administered in an amount and/or for a time to ameliorate at least one symptom of Alzheimer's Disease, to reduce neuronal damage associated with Alzheimer's Disease, and/or to reduce inflammation associated with Alzheimer's Disease. The agent can be administered in combination with another treatment for Alzheimer's Disease, e.g., tacrine (COGNEX®), donepezil (ARICEPT®), rivastigmine (EXELON®), galantamine (REMINYL®), memantine (NAMENDA™), nonsteroidal anti-inflammatory drugs (NSAIDS), statins, folic acid, gingko biloba, or vitamin E, B6, or B12. Further, the method can include evaluating the subject using an Alzheimer's Disease function assessment criterion, such as the Progressive Deterioration Scale (PDS) or the Mini-Mental State Examination (MMSE). The method can include a step of identifying a subject who has Alzheimer's Disease, e.g., detecting Alzheimer's Disease in a subject. A TWEAK/TWEAK-R blocking agent can be packaged in a container that has a label with instructions for use of the agent in treating Alzheimer's Disease. The disclosure also features an agent that blocks a TWEAK/TWEAK-R interaction or activity for use in treating Alzheimer's Disease and for the manufacture of a medicament for treating Alzheimer's Disease.

In addition to ALS, Huntington's Disease, Alzheimer's Disease, and Parkinson's Disease, a TWEAK/TWEAK-R blocking agent can be used to treat or prevent other neurological disorders including neurodegenerative disorders. These disorders include ones that cause damage to motor neurons, inter-neurons, and/or sensory neurons, or neurons of particular classes, e.g., dopamine producing neurons. Examples of such disorders include disorders that involve gradual degeneration of neuronal function, e.g., in the central or peripheral nervous system. Such degeneration can result from a variety of pathologies, including the accumulation of toxic structures such as neurofibrillary tangles, protein aggregates, prions, and plaques. Many neurodegenerative disorders, such as ones of these classes, are mediated by pathologies independent of an autoimmune reaction against myelin or, more generally an autoimmune reaction against any self-antigen. Some neurodegenerative disorders can be mediated in part by trinucleotide expansion in genes, resulting in proteins that cause polyglutamine aggregation. Examples of such disorders include: Huntington's disease, Spinalbulbar Muscular Atrophy (SBMA or Kennedy's Disease) Dentatontbropallidoluysian Atrophy (DRPLA), Spinocerebellar Ataxia 1 (SCA1), Spinocerebellar Ataxia 2 (SCA2), Machado-Joseph Disease (MJD; SCA3), Spinocerebellar Ataxia 6 (SCA6), Spinocerebellar Ataxia 7 (SCA7), and Spinocerebellar Ataxia 12 (SCA 12).

Examples of neurodegenerative disorders mediated by prions include Creutzfeldt-Jakob disease (CJD) and so-called "mad-cow disease." In another aspect, the disclosure features a method of evaluating a subject. The method includes detecting a TWEAK or TWEAK receptor (e.g., Fn14) protein or a nucleic acid encoding TWEAK or a TWEAK receptor in a subject. In one embodiment, the method includes correlating the result of the detection with the subject's risk for a neurological disorder, other injury, or pathology. The term "correlating" refers to describing the relationship between the presence or level of TWEAK or TWEAK-R protein or nucleic acid, and the presence or level of risk for a neurological disorder, other injury, or pathology. For example, increased expression can indicate that the subject has suffered a neuronal or other injury to the brain or spinal cord, or a neurological disorder, or is at risk for one. Such correlation may be displayed in a record, e.g., a printed or computer readable material, e.g., an informational, diagnostic, or instructional material, e.g., to the subject, health care provider, or insurance company, identifying the presence or level of TWEAK or a TWEAK-R protein or nucleic acid as a risk or diagnostic factor for a neurological, disorder, other injury, or pathology. In another embodiment, increased expression can indicate that the subject has had a neuronal or other injury or pathology in the brain or spinal cord or a neurological disorder. In one embodiment, a labeled agent that binds to TWEAK or a TWEAK receptor is administered to the subject and the subject is monitored (e.g., scanned) to detect one or more locations in the brain or spinal cord where TWEAK or a TWEAK receptor expressed. The method can identify locations where TWEAK or a TWEAK receptor expression is increased. In other embodiments, TWEAK or TWEAK receptor expression is detected in a biological sample from the subject.

In another aspect the disclosure features a method of evaluating a subject or performing a risk assessment for a neuronal disorder such as a mechanical neuronal trauma, a neurodegenerative disorder, or other disorder described herein. The method includes evaluating TWEAK or TWEAK-R protein or a nucleic acid encoding TWEAK or a TWEAK receptor in the subject or in a sample obtained from the subject. For example, the step of evaluating includes evaluating expression or activity of a TWEAK or TWEAK-R protein or a nucleic acid encoding TWEAK or a TWEAK receptor (e.g., by qualitative or quantitative analysis of mRNA, cDNA, or protein), or evaluating one or more nucleotides in a nucleic acid (genomic, mRNA, or cDNA) encoding TWEAK or a TWEAK receptor. In one embodiment, the subject has sustained, is suspected of having sustained, or is known or suspected to have a predisposition for a neuronal disorder, such as a mechanical neuronal trauma, a neurodegenerative disorder, or other disorder described herein. In one embodiment, the method includes administering a labeled TWEAK or TWEAK receptor binding agent (e.g., an antibody) to a subject, and evaluating localization of the labeled binding agent in the subject, e.g., by imaging the subject (e.g., imaging at least a portion of the brain of the subject). For example, a NMR-detectable antibody to a TWEAK receptor can be used to identify Fn14 overexpressing cells at site of damage from a neuronal or other injury or pathology in the brain or spinal cord or a neurological disorder.

Results of the evaluating can be used to provide a risk or an assessment of status for sustaining a neuronal disorder such as a mechanical neuronal trauma, a neurodegenerative disorder, or other disorder described herein, e.g., by comparison to a reference, e.g., a reference value for a normal subject, a control subject, or a value determined, e.g., for a cohort of subjects.

The method can be used to evaluate a treatment for a neuronal disorder such as a mechanical neuronal trauma, a neurodegenerative disorder, or other disorder described herein. For example, the subject is receiving a treatment for a neuronal disorder, e.g., a disorder described herein (e.g., a treatment using a TWEAK/TWEAK-R blocking agent, or other treatment for the particular disorder). The subject can be evaluated before, during, or after receiving the treatment, e.g., multiple times during the course of treatment. A decrease in TWEAK and/or TWEAK receptor expression can indicate an improvement in the condition of the subject.

The method can be used to identify a subject for treatment for a neuronal disorder such as a mechanical neuronal trauma, a neurodegenerative disorder, or other disorder described herein. The subject can be identified as a subject suited for such treatment as a function of results of the evaluating, e.g., the results show similarity to, e.g., statistically significant similarity to, a reference value indicative of a subject requiring such a treatment. For example, elevated TWEAK or TWEAK receptor expression can be indicative of a subject who can be treated with a TWEAK/TWEAK-R blocking agent or other treatment appropriate for the neuronal disorder.

The method can also be used to select a patient population for treatment. Expression of TWEAK or a TWEAK receptor is evaluated for one or more subjects. A set of one or more subjects who have elevated expression of TWEAK or a TWEAK receptor relative to a reference are selected. The subjects of the set are administered an agent that blocks a TWEAK/TWEAK-R interaction or activity or other treatment for a neuronal disorder such as a mechanical neuronal trauma, a neurodegenerative disorder, or other disorder described herein.

In another aspect, this disclosure features a method that includes a) determining the identity of at least one nucleotide in the TWEAK and/or a TWEAK receptor locus of a subject; and b) creating a record which includes information about the identity of the nucleotide and information relating to a parameter of the subject that corresponds to a neuronal disorder such as a mechanical neuronal trauma, a neurodegenerative disorder, or other disorder described herein, wherein the parameter is other than the genotype of TWEAK or TWEAK-R genes. The method can be used e.g., for gathering genetic information. In one embodiment, the determining includes evaluating a sample including human genetic material from the subject. A related method includes: (a) evaluating a parameter of a TWEAK and/or TWEAK receptor molecule (a TWEAK/TWEAK-R parameter) from a mammalian subject; and (b) evaluating a parameter related to a neuronal disorder such as a mechanical neuronal trauma, a neurodegenerative disorder, or other disorder described herein of the subject wherein the parameter is other than the parameter of (a).

The methods can also include (c) recording information about the TWEAK/TWEAK-R parameter and information about the parameter related to a neuronal disorder, wherein the information about the parameter and information about the phenotypic trait are associated with each other in a record, e.g., a database. For example, the parameter is a phenotypic trait of the subject, e.g., a parameter related to the disorder, e.g., a description of symptoms of the disorder, e.g., a qualitative or quantitative evaluation of such symptoms.

In one embodiment, the TWEAK and/or TWEAK receptor molecule is a polypeptide and the TWEAK/TWEAK-R parameter includes information about a TWEAK/TWEAK-R polypeptide. In another embodiment, the TWEAK and/or TWEAK receptor molecule is a nucleic acid that encodes TWEAK or TWEAK receptor and the TWEAK/TWEAK parameter includes information about the identity of a nucleotide in the TWEAK/TWEAK-R gene. Other parameters can relate to TWEAK and/or TWEAK receptor expression, activity, modification, or localization (e.g., subcellular or organismal).

In an embodiment, the subject is an embryo, blastocyst, or fetus. In another embodiment, the subject is a post-natal human, e.g., a child or an adult (e.g., at least 20, 30, 40, 50, 60, or 70 years of age).

In one embodiment, step (b) is performed before or concurrent with step (a). In one embodiment, the human genetic material includes DNA and/or RNA.

The method can further include comparing the TWEAK/TWEAK-R parameter to reference information, e.g., information about a corresponding nucleotide from a reference sequence. The method can be used, e.g., to provide a diagnosis of a neuronal disorder for a subject who does not yet exhibit symptoms or who does exhibit symptoms, but whose diagnosis is uncertain. In one embodiment, the reference sequence is from a reference subject that has a neuronal disorder such as a mechanical neuronal trauma, a neurodegenerative disorder, or other disorder described herein, e.g., a neurological disorder at an age associated with early onset for the disorder, e.g., in some cases an age of less than age 60, 55, 50, or 45.

In one embodiment, the method further includes comparing the nucleotide to a corresponding nucleotide from a genetic relative or family member (e.g., a parent, grandparent, sibling, progeny, prospective spouse, etc.).

In one embodiment, the method further includes evaluating risk or determining diagnosis of a neuronal disorder such as a mechanical neuronal trauma, a neurodegenerative disorder, or other disorder described herein in the subject as a function of the genotype.

In one embodiment, the method further includes recording information about the TWEAK/TWEAK-R parameter and a parameter related to a neuronal disorder such as a mechanical neuronal trauma, a neurodegenerative disorder, or other disorder described herein, e.g., in a record or database. For example, the information is recorded in linked fields of a database (e.g., TWEAK/TWEAK-R parameter is linked to at least one of: corresponding TWEAK/TWEAK-R parameter and/or data regarding comparison with the reference sequence). The nucleotide can be located in an exon, intron, or regulatory region of the TWEAK/TWEAK-R gene. For example, the nucleotide is a SNP. In one embodiment, a plurality of nucleotides (e.g., at least 10, 20, 50, 100, 500, or 1000 nucleotides (e.g., consecutive or non-consecutive)) in the TWEAK/TWEAK-R locus are evaluated. In another embodiment, a single nucleotide is evaluated.

In one embodiment, the method includes one or more of: evaluating a nucleotide position in the TWEAK/TWEAK-R locus on both chromosomes of the subject; recording the information (e.g., as phased or unphased information); aligning the genotyped nucleotides of the sample and the reference sequence; and identifying nucleotides that differ between the subject nucleotides and the reference sequence.

The method can be repeated for a plurality of subjects (e.g., at least 10, 25, 50, 100, 250, or 500 subjects).

In one embodiment, the method can include comparing the information of step a) and step b) to information in a database, and evaluating the association of the genotyped nucleotide(s) with a neuronal disorder such as a mechanical neuronal trauma, a neurodegenerative disorder, or other disorder described herein.

In another aspect, the invention features a computer readable record encoded with (a) a subject identifier, e.g., a patient identifier, (b) one or more results from an evaluation of the subject, e.g., a diagnostic evaluation described herein, e.g., the level of expression, level or activity of TWEAK or a TWEAK receptor, in the subject, and optionally (c) a value for or related to a neuronal disorder such as a mechanical neuronal trauma, a neurodegenerative disorder, or other disorder described herein, e.g., a value correlated with injury or disorder status or risk with regard to such injury or disorder. In one embodiment, the invention features a computer medium having a plurality of digitally encoded data records. Each data record includes a value representing the expression, level or activity of TWEAK or a TWEAK receptor levels or activity, in a sample or subject, and a descriptor of the sample or the subject. The descriptor of the sample can be an identifier of the sample, a subject from which the sample was derived (e.g., a patient), a diagnosis, or a treatment (e.g., a treatment described herein). In a preferred embodiment, the data record further includes values representing the level or location of expression, level or activity of genes other than TWEAK or TWEAK receptor (e.g., other genes associated with a neuronal disorder such as a mechanical neuronal trauma, a neurodegenerative disorder, or other disorder described herein, or other genes on an array). The data record can be structured as a table, e.g., a table that is part of a database such as a relational database (e.g., a SQL database of the Oracle or Sybase database environments). It is also possible to communicate information about a subject, e.g., by transmitting information, e.g., transmitting a computer readable record described herein, e.g., over a computer network.

All cited patents, patent applications, and references are hereby incorporated by reference in their entireties. In the case of conflict, the present application controls.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
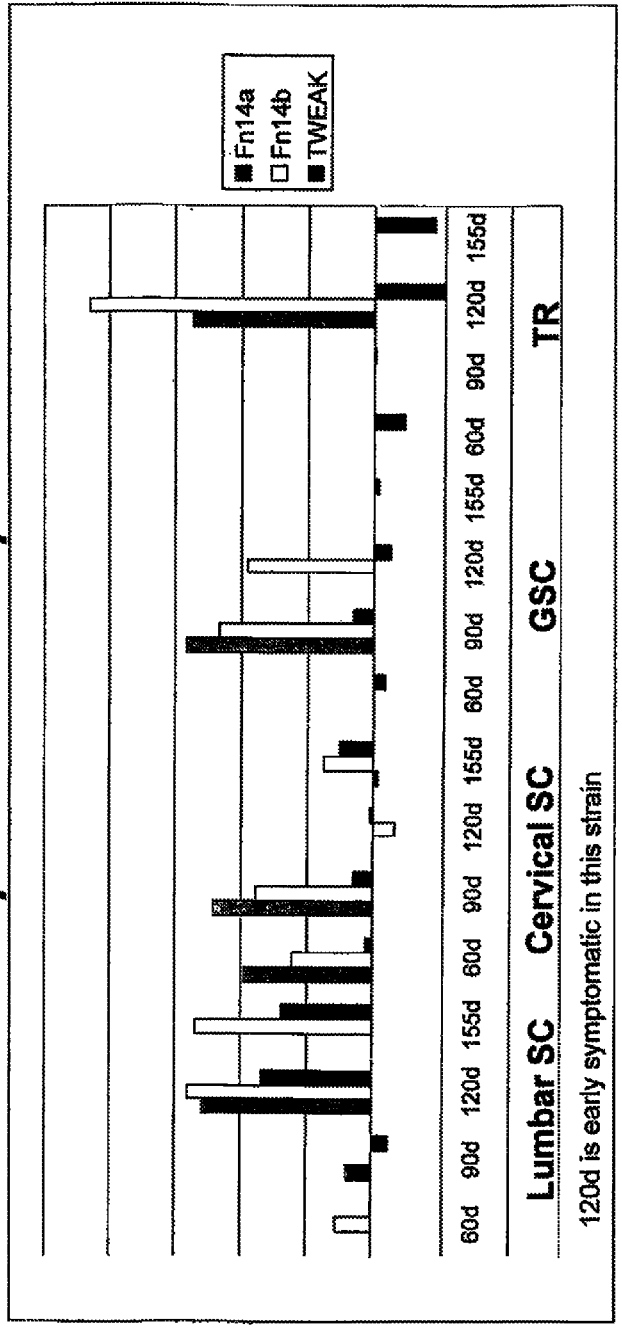
FIG. 1 is a bar graph showing TWEAK and Fn14 levels in FALS.

Administration of a TWEAK/TWEAK-R blocking agent, e.g., a TWEAK antibody, can reduce neuronal injury or pathology in the central or peripheral nervous system. A TWEAK/TWEAK-R blocking agent may also minimize damage associated with apoptosis, inflammation, or other secondary processes associated with a disorder described herein. As further described herein, a TWEAK/TWEAK-R blocking agent can be used to treat or prevent neurodegenerative diseases, e.g., disorders characterized by the degeneration (frequently gradual) and death of neurons, such as motor neurons, inter-neurons, or sensory neurons, as well as other neurological diseases.

Surprisingly, a TWEAK/TWEAK-R blocking agent can mitigate neuronal damage associated with a neurodegenerative disorder in which autoimmunity is not a principal mediator. The ability of the blocking agent to prevent neuronal cell death or to reduce inflammation (e.g., inflammation mediated by glial cells and astrocytes) may contribute to such therapeutic results.

In addition to neurodegenerative disorders in which autoimmunity is not a principal mediator, a TWEAK/TWEAK-R blocking agent can also be used to treat autoimmune disorders which cause neuronal damage. For example, the blocking agent can be used to treat multiple sclerosis, a condition in which the immune system attacks myelin sheaths of neurons. However, the blocking agent is also effective at treating other neuronal disorders in which autoimmunity may be implicated, e.g., ALS, in which the immune system may attack motor neurons themselves, rather than the surrounding myelin tissue. Accordingly, a TWEAK/TWEAK-R blocking agent can be used to treat autoimmune disorders with a neuronal pathology that are not based on immunological damage to myelin.

The term "treating" refers to administering a therapy in an amount, manner, and/or mode effective to improve or prevent a condition, symptom, or parameter associated with a disorder (e.g., SCI, TBI, ALS, Parkinson's Disease, Huntington's Disease, Alzheimer's Disease, or other disorder described herein) or to prevent onset, progression, or exacerbation of the disorder (including secondary damage caused by the disorder, e.g., neuronal injury to or inflammation in the brain, spinal cord, or peripheral nervous system), to either a statistically significant degree or to a degree detectable to one skilled in the art. Accordingly, treating can achieve therapeutic and/or prophylactic benefits. An effective amount, manner, or mode can vary depending on the subject and may be tailored to the subject.

TWEAK/TWEAK-Receptor Blocking Agents

A variety of agents can be used as a TWEAK/TWEAK-R blocking agent to treat neuronal or other injury or pathology in the brain or spinal cord or neurological disorders. The agent may be any type of compound (e.g., small organic or inorganic molecule, nucleic acid, protein, or peptide mimetic) that can be administered to a subject. In one embodiment, the blocking agent is a biologic, e.g., a protein having a molecular weight of between 5-300 kDa. For example, a TWEAK/TWEAK-R blocking agent may inhibit binding of TWEAK to a TWEAK receptor or may prevent TWEAK-mediated NF-κB activation. A typical TWEAK/TWEAK-R blocking agent can bind to TWEAK or a TWEAK receptor, e.g., Fn14. A TWEAK/TWEAK-R blocking agent that binds to TWEAK may alter the conformation of TWEAK or a TWEAK receptor, block the binding site on TWEAK or a TWEAK receptor, or otherwise decrease the affinity of TWEAK for a TWEAK receptor or prevent the interaction between TWEAK and a TWEAK receptor. A TWEAK/TWEAK-R blocking agent (e.g., an antibody) may bind to TWEAK or to a TWEAK receptor with a $K_d$ of less than $10^{-6}$, $10^{-7}$, $10^{-8}$, $10^{-9}$, or $10^{-10}$ M. In one embodiment, the blocking agent binds to TWEAK with an affinity at least 5, 10, 20, 50, 100, 200, 500, or 1000 better than its affinity for TNF or another TNF superfamily member (other than TWEAK). In one embodiment, the blocking agent binds to the TWEAK receptor with an affinity at least 5, 10, 20, 50, 100, 200, 500, or 1000-fold better than its affinity for the TNF receptor or a receptor for another TNF superfamily member. A preferred TWEAK/TWEAK-R blocking agent specifically binds TWEAK or a TWEAK receptor, such as a TWEAK or TWEAK-R specific antibody.

Exemplary TWEAK protein molecules include human TWEAK (e.g., AAC51923, shown as SEQ JD NO:1)), mouse TWEAK (e.g., NP_035744.1), rat TWEAK (e.g., XP_340827.1), and *Pan troglodytes* TWEAK (e.g., XP_511964.1). Also included are proteins that include an amino acid sequence at least 90, 92, 95, 97, 98, 99% identical and completely identical to the mature processed region of the aforementioned TWEAK proteins (e.g., an amino acid sequence at least 90, 92, 95, 97, 98, 99% identical or completely identical to amino acids $X_1$-249 of SEQ ID NO: 1, where amino acid $X_1$ is selected from the group of residues 75-115 of SEQ ID NO:1, e.g., $X_1$ is residue Arg 93 of SEQ ID NO:1) and proteins encoded by a nucleic acid that hybridizes under high stringency conditions to a human, mouse, rat, or *Pan troglodytes* gene encoding a naturally occurring TWEAK protein. Preferably, a TWEAK protein, in its processed mature form, is capable of providing at least one TWEAK activity, e.g., ability to activate Fn14.

Exemplary TWEAK receptor molecules include Fn14. Exemplary Fn14 protein molecules include human Fn14 (e.g., NP_057723.1, shown as SEQ ID NO:2), mouse Fn14 (e.g., NP_038777.1), and rat Fn14 (e.g., NP_851600.1), as well as soluble proteins that include an amino acid sequence at least 90, 92, 95, 97, 98, 99% identical or 100% identical to the extracellular domain of Fn14 (and TWEAK-binding fragments thereof) and proteins encoded by a nucleic acid that hybridizes under high stringency conditions to a human, mouse, rat, or *Pan troglodytes* gene encoding a naturally-occurring Fn14 protein. Preferably, an Fn14 protein useful in the methods described herein is a soluble Fn14 (lacking a transmembrane domain) that includes a region that binds to a TWEAK protein, e.g., an amino acid sequence at least 90, 92, 95, 97, 98, or 99% identical, or completely identical, to amino acids 28-$X_1$ of SEQ ID NO:2, where amino acid $X_1$ is selected from the group of residues 68 to 80 of SEQ ID NO:2.

Calculations of "homology" or "sequence identity" between two sequences (the terms are used interchangeably herein) are performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). The optimal alignment is determined as the best score using the GAP program in the GCG software package with a Blossom 62 scoring matrix with a gap penalty of 12, a gap extend penalty of 4, and a frameshift gap penalty of 5. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences.

As used herein, the term "hybridizes under high stringency conditions" describes conditions for hybridization and washing. Guidance for performing hybridization reactions can be found in *Current Protocols in Molecular Biology*, John Wiley & Sons, N.Y. (1989), 6.3.1-6.3.6, Aqueous and nonaqueous methods are described in that reference and either can be used High stringency hybridization conditions include hybridization in 6×SSC at about 45° C., followed by one or more washes in 0.2×SSC, 0.1% SDS at 65° C., or substantially similar conditions.

Exemplary TWEAK/TWEAK-R blocking agents include antibodies that bind to TWEAK or a TWEAK receptor and soluble forms of the TWEAK receptor that compete with cell surface TWEAK receptor for binding to TWEAK. An example of a soluble form of the TWEAK receptor is an Fc fusion protein that includes at least a portion of the extracellular domain of TWEAK receptor (e.g., a soluble TWEAK binding fragment of TWEAK receptor), referred to as TWEAK-R-Fc. Other soluble forms of a TWEAK receptor, e.g., forms that do not include an Fc domain, can also be used. Antibody blocking agents are further discussed below. Other types of blocking agents, e.g., small molecules, nucleic acid or nucleic acid-based aptamers, and peptides, can be isolated by screening, e.g., as described in Jhaveri et al. (2000) *Nat. Biotechnol*, 18:1293 and U.S. Pat. No. 5,223,409. Exemplary assays for determining if an agent binds to TWEAK or TWEAK receptor and for determining if an agent modulates a TWEAK/TWEAK-R interaction are described, e.g., in U.S. Pub. App. No. 2004-0033225.

An exemplary soluble form of the TWEAK-R protein includes a region of the TWEAK-R protein that binds to TWEAK, e.g., about amino acids 32-75, 31-75, 31-78, or 28-79 of SEQ ID NO:2. This region can be physically associated, e.g., fused to another amino acid sequence, e.g., an Fc domain, at its N- or C-terminus. The region from TWEAK receptor can be spaced by a linker from the heterologous amino acid sequence. U.S. Pat. No. 6,824,773 describes an exemplary TWEAK receptor fusion protein.

Antibodies

Exemplary TWEAK/TWEAK-R blocking agents include antibodies that bind to TWEAK and/or a TWEAK receptor. In one embodiment, the antibody inhibits the interaction between TWEAK and a TWEAK receptor, e.g., by physically blocking the interaction, decreasing the affinity of TWEAK and/or a TWEAK receptor for its counterpart, disrupting or destabilizing TWEAK complexes, sequestering TWEAK or a TWEAK receptor, or targeting TWEAK or a TWEAK receptor for degradation. In one embodiment, the antibody can bind to TWEAK or a TWEAK receptor at one or more amino acid residues that participate in the TWEAK/TWEAK-R binding interface. Such amino acid residues can be identified, e.g., by alanine scanning. In another embodiment, the antibody can bind to residues that do not participate in the TWEAK/TWEAK-R binding. For example, the antibody can alter a conformation of TWEAK or a TWEAK receptor and thereby reduce binding affinity, or the antibody may sterically hinder TWEAK/TWEAK-R binding. In one embodiment, the antibody can prevent activation of a TWEAK/TWEAK-R mediated event or activity (e.g., NF-κB activation).

As used herein, the term "antibody" refers to a protein that includes at least one immunoglobulin variable region, e.g., an amino acid sequence that provides an immunoglobulin variable domain or an immunoglobulin variable domain sequence. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody" encompasses antigen-binding fragments of antibodies (e.g., single chain antibodies, Fab fragments, F(ab')₂ fragments, Fd fragments, Fv fragments, and dAb fragments) as well as complete antibodies, e.g., intact and/or full length immunoglobulins of types IgA, IgG (e.g., IgG1, IgG2, IgG3, IgG4), IgE, IgD, IgM (as well as subtypes thereof). The light chains of the immunoglobulin may be of types kappa or lambda. In one embodiment, the antibody is glycosylated. An antibody can be functional for antibody-dependent cytotoxicity and/or complement-mediated cytotoxicity, or may be non-functional for one or both of these activities.

The VH and VL regions can be further subdivided into regions of hypervariability, termed "complementarity determining regions" ("CDR"), interspersed with regions that are more conserved, termed "framework regions" (FR). The extent of the FR's and CDR's has been precisely defined (see, Kabat, E. A. et al. (1991) *Sequences of Proteins of Immunological Interest, Fifth Edition*, U.S. Department of Health and Human Services, NIH Publication No. 91-3242; and Chothia. C. et al (1987) *J. Mol. Biol.* 196:901-917). Kabat definitions are used herein. Each VH and VL is typically composed of three CDR's and four FR's, arranged from amino-terminus to carboxyl-terminus in the following order: FR1, CDR1, FR2, CDR2, FR3, CDR3, FR4.

An "immunoglobulin domain" refers to a domain from the variable or constant domain of immunoglobulin molecules. Immunoglobulin domains typically contain two β-sheets formed of about seven β-strands, and a conserved disulphide bond (see, e.g., A. F. Williams and A. N. Barclay (1988) *Ann. Rev. Immunol.* 6:381-405). An "immunoglobulin variable domain sequence" refers to an amino acid sequence that can form a structure sufficient to position CDR sequences in a conformation suitable for antigen binding. For example, the sequence may include all or part of the amino acid sequence of a naturally-occurring variable domain. For example, the sequence may omit one, two, or more N- or C-terminal amino acids, internal amino acids, may include one or more insertions or additional terminal amino acids, or may include other alterations. In one embodiment, a polypeptide that includes an immunoglobulin variable domain sequence can associate with another immunoglobulin variable domain sequence to form a target binding structure (or "antigen binding site"), e.g., a structure that interacts with TWEAK or a TWEAK receptor.

The VH or VL chain of the antibody can further include all or part of a heavy or light chain constant region, to thereby form a heavy immunoglobulin chain (HC) or light immunoglobulin chain (LC), respectively. In one embodiment, the antibody is a tetramer of two heavy immunoglobulin chains and two light immunoglobulin chains. The heavy and light immunoglobulin chains can be connected by disulfide bonds. The heavy chain constant region typically includes three constant domains, CH1, CH2, and CH3. The light chain constant region typically includes a CL domain. The variable region of the heavy and light chains contains a binding domain that interacts with an antigen. The constant regions of the antibodies typically mediate the binding of the antibody to host tissues or factors, including various cells of the immune system (e.g., effector cells) and the first component (Clq) of the classical complement system.

One or more regions of an antibody can be human, effectively human, or humanized. For example, one or more of the variable regions can be human or effectively human. For example, one or more of the CDRs, e.g., HC CDR1, EC CDR2, HC CDR3, LC CDR1, LC CDR2, and LC CDR3, can be human. Each of the light chain CDRs can be human. HC CDR3 can be human. One or more of the framework regions can be human, e.g., FR1, FR2, FR3, and FR4 of the HC or LC. In one embodiment, all the framework regions are human, e.g., derived from a human somatic cell, e.g., a hematopoietic cell that produces immunoglobulins, or a non-hematopoietic cell. In one embodiment, the human sequences are germline sequences, e.g., encoded by a germline nucleic acid. One or more of the constant regions can be human, effectively human, or humanized. In another embodiment, at least 70, 75, 80, 85, 90, 92, 95, or 98% of the framework regions (e.g., FR1, FR2, and FR3, collectively, or FR1, FR2, FR3, and FR4, collectively) or the entire antibody can be human, effectively human, or humanized. For example, FR1, FR2, and FR3 collectively can be at least 70, 75, 80, 85, 90, 92, 95, 98, or 99% identical, or completely identical, to a human sequence encoded by a human germline segment.

An "effectively human" immunoglobulin variable region is an immunoglobulin variable region that includes a sufficient number of human framework amino acid positions such that the immunoglobulin variable region does not elicit an immunogenic response in a normal human. An "effectively human" antibody is an antibody that includes a sufficient number of human amino acid positions such that the antibody does not elicit an immunogenic response in a normal human.

A "humanized" immunoglobulin variable region is an immunoglobulin variable region that is modified such that the modified form elicits less of an immune response in a human than does the non-modified form, e.g., is modified to include a sufficient number of human framework amino acid positions such that the immunoglobulin variable region does not elicit an immunogenic response in a normal human. Descriptions of "humanized" immunoglobulins include, for example, U.S. Pat. Nos. 6,407,213 and 5,693,762. In some cases, humanized immunoglobulins can include a non-human amino acid at one or more framework amino acid positions.

Antibody Generation

Antibodies that bind to TWEAK or a TWEAK receptor can be generated by a variety of means, including immunization, e.g., using an animal, or in vitro methods such as phage display. All or part of TWEAK or a TWEAK receptor can be used as an immunogen or as a target for selection. For example, TWEAK or a fragment thereof, or a TWEAK receptor or a fragment thereof, can be used as an immunogen. In one embodiment, the immunized animal contains immunoglobulin-producing cells with natural, human, or partially human immunoglobulin loci. In one embodiment, the non-human animal includes at least a part of a human immunoglobulin gene. For example, it is possible to engineer mouse strains deficient in mouse antibody production with large fragments of the human Ig loci. Using the hybridoma technology, antigen-specific monoclonal antibodies derived from the genes with the desired specificity may be produced and selected. See, e.g., XENOMOUSE™, Green at al. (1994) *Nat. Gen,* 713-21; U.S. Pub. App. No. 2003-0070185; U.S. Pat. No. 5,789,650; and PCT Pub. No. WO 96/34096.

Non-human antibodies to TWEAK or a TWEAK receptor can also be produced, e.g., in a rodent. The non-human antibody can be humanized, e.g., as described in EP 239 400; U.S. Pat. Nos. 6,602,503; 5,693,761; and 6,407,213, deimmunized, or otherwise modified to make it effectively human.

EP 239 400 (Winter et al.) describes altering antibodies by substitution (within a given variable region) of their complementarity determining regions (CDRs) for one species with those from another. Typically, CDRs of a non-human (e.g., murine) antibody are substituted into the corresponding regions in a human antibody by using recombinant nucleic acid technology to produce sequences encoding the desired substituted antibody. Human constant region gene segments of the desired isotype (usually gamma I for CH and kappa for CL) can be added and the humanized heavy and light chain genes can be co-expressed in mammalian cells to produce soluble humanized antibody. Other methods for humanizing antibodies can also be used. For example, other methods can account for the three-dimensional structure of the antibody, framework positions that are in three-dimensional proximity to binding determinants, and immunogenic peptide sequences. See, e.g., PCT Pub. No. WO 90/07861; U.S. Pat. Nos. 5,693,762; 5,693,761; 5,585,089; and 5,530, 101; Tempest et al. (1991) *Biotechnology* 9:266-271 and U.S. Pat. No. 6,407,213.

Fully human monoclonal antibodies that bind to TWEAK or a TWEAK receptor can be produced, e.g., using in vitro-primed human splenocytes, as described by Boerner et al. (1991) *J. Immunol.* 147:86-95. They may be prepared by repertoire cloning as described by Persson et al. (1991) *Proc. Natl. Acad. Sci. USA* 88:2432-2436 or by Huang and Stollar (1991) *J. Immunol. Methods* 141:227-236; also U.S. Pat. No. 5,798,230. Large nonimmunized human phage display libraries may also be used to isolate high affinity antibodies that can be developed as human therapeutics using standard phage technology (see, Hoogenboom et al. (1998) *Immunotechnology* 4:1-20; Hoogenboom et al. (2000) *Immunol Today* 2:371-378; and U.S. Pub. App. No. 2003-0232333).

Antibody and Protein Production

Antibodies and other proteins described herein can be produced in prokaryotic and eukaryotic cells. In one embodiment, the antibodies (e.g., scFv's) are expressed in a yeast cell such as *Pichia* (see, e.g., Powers et al. (2001) *J. Immunol. Methods* 251:123-35), *Hanseula*, or *Sacchamtnyces*.

Antibodies, particularly full length antibodies, e.g., IgG's, can be produced in mammalian cells. Exemplary mammalian host cells for recombinant expression include Chinese Hamster Ovary (CHO cells) (including dhfr⁻ CHO cells, described in Urlaub and Chasin (1980) *Proc. Natl. Acad. Sci. USA* 77:4216-4220, used with a DHFR selectable marker, e.g., as described in Kaufman and Sharp (1982) *Mol. Biol.* 159:601-621), lymphocytic cell lines, e.g., NS0 myeloma cells and SP2 cells, COS cells, K562, and a cell from a transgenic animal, e.g., a transgenic mammal. For example, the cell is a mammary epithelial cell.

In addition to the nucleic acid sequence encoding the immunoglobulin domain, the recombinant expression vectors may carry additional nucleic acid sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399,216; 4,634,665; and 5,179,017). Exemplary selectable marker genes include the dihydrofolate reductase (DHFR) gene (for use in dhfr⁻ host cells with methotrexate selectior/amplification) and the neo gene (for G418 selection).

In an exemplary system for recombinant expression of an antibody (e.g., a full length antibody or an antigen-binding portion thereat), a recombinant expression vector encoding both the antibody heavy chain and the antibody light chain is introduced into dhfr⁻ CHO cells by calcium phosphate-mediated transfection. Within the recombinant expression vector, the antibody heavy and light chain genes are each operatively linked to enhancer/promoter regulatory elements (e.g., derived from SV40, CMV, adenovirus, and the like, such as a CMV enhancer/AdMLP promoter regulatory element or an SV40 enhancer/AcMLP promoter regulatory element) to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, to transfect the host cells, to select for transformants, to culture the host cells, and to recover the antibody from the culture medium. For example, some antibodies can be isolated by affinity chromatography with a Protein A or Protein G.

Antibodies (and Fc fusions) may also include modifications, e.g., modifications that alter Fc function, e.g., to decrease or remove interaction with an Fc receptor or with C1q, or both. For example, the human IgG1 constant region can be mutated at one or more residues, e.g., one or more of residues 234 and 237, e.g., according to the numbering in U.S. Pat. No. 5,648,260. Other exemplary modifications include those described in U.S. Pat. No. 5,648,260.

For some proteins that include an Fc domain, the antibody/protein production system may be designed to synthesize antibodies or other proteins in which the Fc region is glycosylated. For example, the Fc domain of IgG molecules is glycosylated at asparagine 297 in the CH2 domain. The Fc domain can also include other eukaryotic post-translational modifications. In other cases, the protein is produced in a form that is not glycosylated.

Antibodies and other proteins can also be produced by a transgenic animal. For example, U.S. Pat. No. 5,849,992 describes a method for expressing an antibody in the mammary gland of a transgenic mammal. A transgene is constructed that includes a milk-specific promoter and nucleic acid sequences encoding the antibody of interest, e.g., an antibody described herein, and a signal sequence for secretion. The milk produced by females of such transgenic mammals includes, secreted-therein, the protein of interest, e.g., an antibody or Fc fusion protein. The protein can be purified from the milk, or for some applications, used directly.

Methods described in the context of antibodies can be adapted to other proteins, e.g., Fc fusions and soluble receptor fragments.

Nucleic Acid Blocking Agents

In certain implementations, nucleic acid blocking agents are used to decrease expression of an endogenous gene encoding TWEAK or a TWEAK receptor, e.g., Fn14. In one embodiment, the nucleic acid antagonist is an siRNA that targets mRNA encoding TWEAK or a TWEAK receptor. Other types of antagonistic nucleic acids can also be used, e.g., a dsRNA, a ribozyme, a triple-helix former, or an antisense nucleic acid.

siRNAs are small double stranded RNAs (dsRNAs) that optionally include overhangs. For example, the duplex region of an siRNA is about 18 to 25 nucleotides in length, e.g., about 19, 20, 21, 22, 23, or 24 nucleotides in length. Typically, the siRNA sequences are exactly complementary to the target mRNA. dsRNAs and siRNAs in particular can be used to silence gene expression in mammalian cells (e.g., human cells). See, e.g., Clemens et al. (2000) *Proc. Natl. Acad. Sci. USA* 97:6499-6503; Billy et al. (2001) *Proc. Natl. Sci. USA* 98:14428-44433; Elbashir et al. (2001) *Nature* 411:494-498; Yang et al. (2002)*Proc. Natl. Acad. Sci. USA* 99:99429947, U.S. Pub App. Nos. 2003-0166282; 2003-0143204: 2004-0038278; and 2003-0224432.

Anti-sense agents can include, for example, from about 8 to about 80 nucleobases (i.e. from about 8 to about 80 nucleotides), e.g., about 8 to about 50 nucleobases, or about 12 to about 30 nucleobases. Anti-sense compounds include ribozymes, external guide sequence (EGS) oligonucleotides (oligozymes), and other short catalytic RNAs or catalytic oligonucleotides which hybridize to the target nucleic add and modulate its expression. Anti-sense compounds can include a stretch of at least eight consecutive nucleobases that are complementary to a sequence in the target gene. An oligonucleotide need not be 100% complementary to its target nucleic acid sequence to be specifically hybridizable. An oligonucleotide is specifically hybridizable when binding of the oligonucleotide to the target interferes with the normal function of the target molecule to cause a loss of utility, and there is a sufficient degree of complementarity to avoid non-specific binding of the oligonucleotide to non-target sequences under conditions in which specific binding is desired, i.e., under physiological conditions in the case of in vivo assays or therapeutic treatment or, in the case of in vitro assays, under conditions in which the assays are conducted.

Hybridization of antisense oligonucleotides with mRNA (e.g., an mRNA encoding TWEAK or a TWEAK receptor) can interfere with one or more of the normal functions of mRNA. The functions of mRNA to be interfered with include all key functions such as, for example, translocation of the RNA to the site of protein translation, translation of protein from the RNA, splicing of the RNA to yield one or more mRNA species, and catalytic activity which may be engaged in by the RNA. Binding of specific protein(s) to the RNA may also be interfered with by antisense oligonucleotide hybridization to the RNA.

Exemplary antisense compounds include DNA or RNA sequences that specifically hybridize to the target nucleic acid, e.g., the mRNA encoding TWEAK or a TWEAK receptor. The complementary region can extend for between about 8 to about 80 nucleobases. The compounds can include one or more modified nucleobases. Modified nucleobases may include, e.g., 5-substituted pyrimidines such as 5-iodouracil, 5-iodocytosine, and C5-propynyl pyrimidines such as C5-propynylcytosine and C5-propynyluracil. Other suitable modified nucleobases include $N^4$-($C_1$-$C_{12}$) alkylaminocytosines and $N^4,N^4$—($C_1$-$C_{12}$) dialkylaminocytosines. Modified nucleobases may also include 7-substituted-8-aza-7-deazapurines and 7-substituted-7-deazapurines such as, for example, 7-iodo-7-deazapurines, 7-cyano-7-deazapurines, 7-aminocarbonyl-7-deazapurines. Examples of these include 6-amino-7-iodo-7-deazapurines, 6-amino-7-cyano-7-deazapurines, 6-amino-7-aminocarbonyl-7-deazapurines, 2-amino-6-hydroxy-7-iodo-7-deazapurines, 2-amino-6-hydroxy-7-cyano-7-deazapurines, and 2-amino-6-hydroxy-7-aminocarbonyl-7-deazapurines. Furthermore, $N^6$—($C_1$-$C_{12}$) alkylaminopurines and $N^6,N^6$—($C_1$-$C_{12}$) dialkylaminopurines, including $N^6$-methylaminoadenine and $N^6,N^6$-dimethylaminoadenine, are also suitable modified nucleobases. Similarly, other 6-substituted purines including, for example, 6-thioguanine may constitute appropriate modified nucleobases. Other suitable nucleobases include 2-thiouracil, 8-bromoadenine, 8-bromoguanine, 2-fluoroadenine, and 2-fluorozuanine. Derivatives of any of the aforementioned modified nucleobases are also appropriate. Substituents of any of the preceding compounds may include $C_1$-$C_{30}$ alkyl, $C_2$-$C_{30}$ alkenyl, $C_2$-$C_{30}$ alkynyl, aryl, aralkyl, heteroaryl, halo, amino, amido, nitro, thio, sulfonyl, carboxyl, alkoxy, alkylcarbonyl, alkoxycarbonyl, and the like.

Descriptions of other types of nucleic acid agents are also available. See, e.g., U.S. Pat. Nos. 4,987,071; 5,116,742; and 5,093,246; Woolf et al. (1992) *Proc. Natl. Acad. Sci. USA* 89:7305-7309; *Antisense RNA and DNA*, D. A, Melton, Ed, Cold Spring Harbor Laboratory; Cold Spring Harbor, N.Y. (1988); Haseloff and Gerlach (1988) *Nature* 334:585-591; Helene, C. (1991) *Anticancer Drug Des,* 6:569-84; Helene (1992) *Ann. N.Y. Acad. Sci.* 660:27-36; and Maher (1992) *Bioassays* 14:807-815.

The nucleic acids described herein, e.g., an anti-sense nucleic acid described herein, can be incorporated into a gene construct to be used as a part of a gene therapy protocol to deliver nucleic acids that can be used to express and produce agents, e.g., anti-sense nucleic acids, within cells. Expression constructs of such components may be administered in any biologically-effective cattier, e.g., any formulation or composition capable of effectively delivering the component gene to cells in vivo. Approaches include insertion of the subject gene in viral vectors including recombinant retroviruses, adenovirus, adeno-associated virus, lentivirus, and herpes simplex virus-1, or recombinant bacterial or eukaryotic plasmids. Viral vectors transfect cells directly; plasmid DNA can be delivered with the help of for example, cationic liposomes lipofectin) or derivatized (e.g., antibody conjugated), polylysine conjugates, gramicidin S, artificial viral envelopes or other such intracellular carriers, as well as direct injection of the gene construct or $CaPO_4$ precipitation canned out in vivo.

A preferred approach for in vivo introduction of nucleic acid into a cell is by use of a viral vector containing nucleic acid, e.g., a cDNA. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells which have taken tip viral vector nucleic acid.

Retrovirus vectors and adeno-associated virus vectors can be used as a recombinant gene delivery system for the transfer of exogenous genes in vivo, particularly into humans. These vectors provide efficient delivery of genes into cells, and the transferred nucleic acids are stably integrated into the chromosomal DNA of the host. Protocols for producing recombinant retroviruses and for infecting cells in vitro or in vivo with such viruses can be found in *Current Protocols in Molecular Biology*, Ausubel, F. M. et al. (eds.) Greene Publishing Associates, (1989), Sections 9.10-9.14 and other standard laboratory manuals. Examples of suitable retroviruses include pLJ, pZIP, pWE, and pEM which are known to those skilled in the art. Examples of suitable packaging virus lines for preparing both ecotropic and amphotropic retroviral systems include *Crip, *Cre, *2, and *Am. Retroviruses have been used to introduce a variety of genes into many different cell types, including epithelial cells, in vitro and/or in vivo (see, for example, Eglitis et al, (1985) *Science* 230:1395-1398; Danos and Mulligan (1988) *Proc. Natl. Acad. Sci. USA* 85:6460-6464; Wilson et al. (1988) *Proc. Natl. Acad. Sci. USA* 85:3014-3018; Armentano et al. (1990) *Proc. Natl. Acad. Sci. USA* 87:6141-6145; Huber et al. (1991) *Proc. Natl. Acad. Sci. USA* 88; 8039-8043; Ferry et al. (1991) *Proc. Natl. Acad. Sci. USA* 88; 8377-8381; Chowdhury et. al. (1991) *Science* 254:1802-1805; van Beusechem et al. (1992) *Proc. Natl. Acad. Sci. USA* 89:7640-7644; Kay et al. (1992) *Human Gene Therapy* 3:641-647; Dai et al. (1992) *Proc. Natl. Acad. Sci. USA* 89:10892-10895; Hwu et al. (1993) *J. Immunol.* 150:4104-4115; U.S. Pat. Nos. 4,868,116 and 4,980,286; PCT Pub. Nos. WO 89/07136, WO 89/02468, WO 89/05345, and WO 92/07573).

Another viral gene delivery system utilizes adenovirus-derived vectors. See, for example, Berkner et al. (1988) *BioTechniques* 6:616; Rosenfeld et al. (1991) *Science* 252; 431-434; and Rosenfeld et al. (1992) *Cell* 68:143-155. Suitable adenoviral vectors derived from the adenovirus strain Ad type 5 d1324 or other strains of adenovirus (e.g., Ad2, Ad3, Ad7 etc.) are known to those skilled in the art.

Yet another viral vector system useful for delivery of the subject gene is the adeno-associated virus (AAV). Set, for example, Platte et al. (1992) *Am. J. Respir. Cell. Mol. Biol.* 7:349-356; Samulski et al. (1989) *J. Virol.* 63:3822-3828; and McLaughlin et al. (1989) *J. Virol.* 62:1963-1973.

Artificial Transcription Factors

Artificial transcription factors can also be used to regulate expression of TWEAK and/or a TWEAK receptor. The artificial transcription factor can be designed or selected, from a library, e.g., for ability to bind to a sequence in an endogenous gene encoding TWEAK or a TWEAK receptor, e.g., in a regulatory region, e.g., the promoter. For example, the artificial transcription factor can be prepared by selection in vitro (e.g., using phage display, U.S. Pat. No. 6,534,261) or in vivo, or by design based on a recognition code (see, e.g., PCT Pub. No. WO 00/42219 and U.S. Pat. No. 6,511, 808). See, e.g., Rebar et al. (1996) *Methods Enzyme* 267: 129; Greisman and Pabo (1997) *Science* 275:657; Isalan et al. (2001) *Nat. Biotechnol.* 19:656; and Wu et al. (1995) *Proc. Natl. Acad. Sci. USA* 92:344 for, among other things, methods for creating libraries of varied zinc finger domains.

Optionally, an artificial transcription factor can be fused to a transcriptional regulatory domain, e.g., an activation domain to activate transcription or a repression domain to repress transcription. In particular, repression domains can be used to decrease expression of endogenous genes encoding TWEAK or TWEAK receptor. The artificial transcription factor can itself be encoded by a heterologous nucleic acid that is delivered to a cell or the protein itself can be delivered to a cell (see, e.g., U.S. Pat. No. 6,534,261). The heterologous nucleic acid that includes a sequence encoding the artificial transcription factor can be operably linked to an inducible promoter, e.g., to enable fine control of the level of the artificial transcription factor in the cell, e.g., a neuronal or glial cell, e.g., at or near a site of neuronal or other injury in the brain or spinal cord or at the site of neurodegeneration caused by a neurological disorder.

Spinal Cord Injury (SCI)

A TWEAK/TWEAK-R blocking agent can be administered to treat spinal cord injury (SCI). Spinal cord injury (SCI) occurs when an event, typically a traumatic event, results in damage to cells within the spinal cord or severs the nerve tracts that relay signals up and down the spinal cord. Common types of SCI include contusion (bruising of the spinal cord) and compression (caused by pressure on the spinal cord). Other types of injuries include lacerations (severing or tearing of some nerve fibers, such as damage caused by a gun shot wound), and central cord syndrome (specific damage to the corticospinal tracts of the cervical region of the spinal cord).

Severe SCI often causes paralysis (loss of control over voluntary movement and muscles of the body) and loss of sensation and reflex fruition below the point of injury, including autonomic activity such as breathing and other activities such as bowel and bladder control. Other symptoms such as pain or sensitivity to stimuli, muscle spasms, and sexual dysfunction may develop over time. SCI patients are also prone to develop secondary medical problems, such as bladder infections, lung infections, and bed sores.

While recent advances in emergency care and rehabilitation allow many SCI patients to survive, methods for reducing the extent of injury and for restoring function are still limited. Immediate treatment for acute SCI can include administration (local and/or systemic) of a TWEAK/TWEAK-R blocking agent. Immediate treatment can further include one or more of: techniques to relieve cord compression, drug therapy with corticosteroids such as methylprednisolone to minimize cell damage, and stabilization of the vertebrae of the spine to prevent further injury. One or more of these treatments can be used in combination with a TWEAK/TWEAK-R blocking agent. These immediate treatments can be provided promptly, e.g., within 2, 4, 8, 12, or 24 hours of injury.

Administration of a TWEAK/TWEAK-K blocking agent can also be used as a rehabilitation strategy, e.g., to minimize long-term disability or otherwise improve a condition of the subject, e.g., ameliorating one or more SCI symptoms. A neurological exam can be performed to determine the location (e.g., which spinal region (e.g., cervical, thoracic, lumbar, sacral) and which spinal levels (e.g., C1-C7, T1-T12, T12-L5, S1-S5)) have been injured. The extent and progression of, and improvement in, the injury can be measured by various criteria, e.g., the American Spinal Injury Association uses a scale of 0-5 to assess motor strength in SCI: 0— no contraction or movement; 1—minimal movement; 2—active movement, but not against gravity; 3—active movement against gravity; 4—active movement against resistance; 5—active movement against full resistance.

The efficacy and dosing of a TWEAK/TWEAK-R blocking agent can be evaluated in an animal model of SCI. Examples include: a laminectomy, e.g., at the 9th-to-10th thoracic (T9-T10) spinal vertebrae, followed by a lateral hemisection at the T9-T10 level (Teng et. al. (2002) *Proc. Natl. Acad, Sci. USA* 99:3024-3029); a crushing model (see, e.g., Wamil et al. (1998) *Proc. Natl. Acad. Sci. USA* 95:13188-13193); and a contusive model (Kuhn and Wrathall (1998) *J. Neurotrauma* 15:125-40).

Traumatic Brain Injury (TBI)

A TWEAK/TWEAK-R blocking agent can be administered to treat traumatic brain injury (TBI). TBI is typically the result of physical damage to the head. For example, TBI occurs when a sudden physical assault on the head causes damage to the brain. The damage can be focal, confined to one area of the brain, or diffuse, involving more than one area of the brain. TBI can result from a closed head injury or a penetrating head injury. A closed head injury occurs when the head suddenly and violently hits an object, but the object does not break through the skull. A penetrating head injury occurs when an object pierces the skull and enters the brain tissue. Several types of traumatic injuries can affect the head and brain. A skull fracture occurs when the bone of the skull cracks or breaks. A depressed skull fracture occurs when pieces of the broken skull press into the tissue of the brain. This can cause bruising of the brain tissue, called a contusion. A contusion can also occur in response to shaking of the brain within the confines of the skull, an injury called "countrecoup." Shaken Baby Syndrome is a severe form of head injury that occurs when a baby is shaken forcibly enough to cause extreme countrecoup injury. Damage to a major blood vessel within the head can cause a hematoma or heavy bleeding into or around the brain.

Symptoms of a TBI may include headache, nausea, confusion or other cognitive problems, a change in personality, depression, irritability, and other emotional and behavioral problems. Some people may have seizures or enter a coma as a result of a TBI.

Immediate treatment for TBI can include administration (local and/or systemic) of a TWEAK/TWEAK-R blocking agent. Other immediate treatment can include surgery to control bleeding in and around the brain, monitoring and controlling intracranial pressure, insuring adequate blood flow to the brain, and treating the body for other injuries and infection. One or more of these treatments can be used in combination with a TWEAK/TWEAK-R blocking agent. Immediate treatments can be provided promptly; e.g., within 2, 4, 8, 12 or 24 hours of injury.

Later treatment can also include administration (local and/or systemic) of a TWEAK/TWEAK-R blocking agent, e.g., to improve the condition of the subject. The Glasgow Coma Scale can be used to rate the extent of injury and chances of recovery. The scale (3-15) involves testing for three patient responses: eye opening, best verbal response, and best motor response. A high score indicates a good prognosis and a low score indicates a poor prognosis. A TWEAK/TWEAK-R blocking agent can be used to ameliorate a subject's performance on this scale, or other assessment criteria.

The efficacy and dosing of a TWEAK/TWEAK-R blocking agent can be evaluated in an animal model of TBI, e.g., a mouse model (see, e.g., Zohar et (2003) *Neuroscience* 118:949-955).

Amyotrophic Lateral Sclerosis (ALS)

A TWEAK/TWEAK-R blocking agent can be administered to treat amyotrophic lateral sclerosis (ALS). ALS, sometimes called Lou Gehrig's disease, is a rapidly progressive neurological disease that attacks the nerve cells (neurons) that control voluntary muscles. The disease is one of many motor neuron diseases characterized by the gradual degeneration and death of motor neurons.

In ALS, both the upper motor neurons (those in the bran and the lower motor neurons (those in the spinal cord) degenerate or die. The cessation of signals to the muscles causes than to gradually weaken, atrophy, and twitch (e.g., experience fasoiculations). Eventually, the ability of the brain to start and control voluntary movement is lost.

ALS causes weakness with a wide range of disabilities. Eventually, all muscles under voluntary control are affected, and patients lose their strength and the ability to move their arms, legs, and body. When muscles in the diaphragm and chest wall fail, patients lose the ability to breathe without ventilatory support. Most people with ALS die from respiratory failure, usually within 3 to 5 years from the onset of symptoms. However, about 10 percent of ALS patients survive for 10 or more years.

A TWEAK/TWEAK-R blocking agent can be used to delay onset, reduce severity, and reduce the rate of progression of ALS. The agent can be used to treat long-term survivors as well patients who exhibit more rapid disease progression. The severity and progression of and improvement in, ALS can be monitored by assessment criteria, e.g., the Appel ALS Ratine. Scale (AALS). It includes assessment of ten parameters (Speech; Salivation; Swallowing; Handwriting; Cutting Food and Handling Utensils; Dressing and Hygiene; Tinning in Bed and Adjusting Bed Clothes; Walking; Climbing Stairs; Breathing); within each parameter, a score ranging from 0 (poor function or inability to perform the function) to 4 (normal function) is assigned. This rating scale provides a single quantitative index of clinical status that documents the variable manifestation and progression of ALS. An increase in the score indicates an improvement in the patient's condition.

As many as 20,000 Americans have ALS, and an estimated 5,000 people in the United States are diagnosed with the disease each years ALS is one of the most common neuromuscular diseases worldwide, and people of all races and ethnic backgrounds are affected. ALS most commonly strikes people between 40 and 60 years of age, but younger and older people also can develop the disease. Men are affected more often than women.

In 90 to 95 percent of all ALS cases, the disease occurs apparently at random with no clearly associated risk factors. About 5 to 10 percent of all ALS cases are inherited. The familial form of ALS (FALS) usually results from a pattern of inheritance that requires only one parent to carry the gene responsible for the disease. About 20 percent of all FALS cases result from a specific genetic defect that leads to mutation of the enzyme known as superoxide dismutase 1 (SOD1). PALS can also be caused by other genetic mutations. In some implementations, subjects who are the progeny of a FALS patient or of a FALS carrier, or who are identified as having PALS (e.g., by a genetic test), are given a prophylactic dose of a TWEAK/TWEAK-R blocking agent, e.g., prior to showing physical symptoms of ALS.

The onset of ALS may be subtle and gradual. The earliest symptoms may include twitching, cramping, or stiffness of muscles; muscle weakness affecting an arm or a leg; slurred and nasal speech; or difficulty chewing or swallowing. These general complaints then develop into more obvious weakness or atrophy that may cause a physician to suspect ALS.

Regardless of the part of the body first affected by the disease, muscle weakness and atrophy spread to other parts of the body as the disease progresses. Patients have increasing problems with moving, swallowing (dysphagia), and speaking or forming words (dysarthria). Symptoms of upper motor neuron involvement include tight and stiff muscles (spasticity) and exaggerated reflexes (hyperreflexia) including an overactive gag reflex. An abnormal reflex commonly called Babinski's sign (the large toe extends upward as the sole of the foot is stimulated in a certain way) also indicates upper motor neuron damage. Symptoms of lower motor neuron degeneration include muscle weakness and atrophy, muscle cramps, and fleeting twitches of muscles that can be seen under the skin. A TWEAK/TWEAK-R blocking agent can be used to ameliorate one or more these symptoms, or to reduce the rate of disease progression.

To be diagnosed with ALS, patients generally must have signs and symptoms of both upper and lower motor neuron damage not attributed to other casues.

Riluzole (RILUTEK®) has been approved for treating ALS, Riluzole is believed to reduce damage to motor neurons by decreasing the release of glutamate. Clinical trials with ALS patients showed that riluzole prolongs survival by several months, mainly in those with difficulty swallowing. Riluzole can be used in combination with a TWEAK/TWEAK-R blocking agent.

The efficacy and dosing of a TWEAK/TWEAK-R blocking agent can be evaluated in an animal model of ALS, e.g., in a mouse or rat overexpressing a mutant form of the human Cu, Zn superoxide dismutase gene (SOD1). In seine models, the mutant form carries a G93A mutation in SOD1 (see, e.g., Tu et al. (1996) *Proc. Natl. Acad. Set. USA* 93:3155-3160; Grieb (2004) *Folia Neuropathol.* 42:239-48; Storkebaum et al. (2005) *Nat. Neurosci.* 3:85-92; Sharp et al. (2005) *Neuroscience* 130:897-910). Transgenic rodents expressing human mutated (inn) SOD-1 develop relatively selective and fatal degeneration of motoneurons. Other transgenic mouse models carry a G85R mutation found in FALS; these mice develop motor neuron disease at 8-10 months of age (Amendola et al. (2004) *Eur J. Neurosci.* 20:2822-2826).

Parkinson's Disease

A TWEAK/TWEAK-R blocking agent can be administered to treat Parkinson's Disease. Parkinson's Disease is a slowly progressive neurodegenerative disorder caused by damaged or dead dopamine neurons in the substantia nigra, a region of the brain that controls balance and coordinates muscle movement.

A TWEAK/TWEAK-R blocking agent can be used to delay onset, reduce severity, and reduce the rate of progression of Parkinson's Disease. The agent can be used to treat long-term survivors as well as patients who exhibit more rapid disease progression.

Four symptoms of Parkinson's Disease often appear gradually but increase in severity with time. They are: trembling in hands, arms, legs, jaw, and face; rigidity or stiffness of the limbs and trunk; slowness of motor movements; postural instability or impaired balance and coordination. A TWEAK/TWEAK-R blocking agent can be used to ameliorate one or more these symptoms, or to reduce the rate of disease progression. The severity and progression of and improvement in, Parkinson's Disease can be assessed by a number of criteria including Hoehn and Yahr Staging of Parkinson's Disease (which classifies the disease into one of five levels with 5 being the most advanced disease); the Schwab and England Activities of Daily Living assessment (which classifies the disease as a percentage 0% (vegetative state) to 100% (completely independent and unimpaired); and the most commonly used Unified Parkinson's Disease Rating Scale (UPDRS). The UPDRS is a rating tool to follow the longitudinal course of Parkinson's Disease. It is made up of the 1) Mentation, Behavior, and Mood, 2) Activities of Daily Living and 3) Motor sections, with multiple parameters in each. Some sections require multiple grades assigned to each extremity. A total of 199 points are possible: 199 represents the worst (total) disability), 0—no disability.

A combination of genetic and environmental factors may cause or contribute to Parkinson's Disease. A rare hem of Parkinson's Disease is the result of an inherited genetic mutation, but the common form of Parkinson's Disease is sporadic. In some implementations, subjects who are the progeny of a Parkinson's Disease patient or of a carrier of the genetic mutation Parkinson's Disease, or who are identified as having Parkinson's Disease. (e.g., by a genetic test), are given a prophylactic dose of a TWEAK/TWEAK-R blocking agent, e.g., prior to showing physical symptoms of Parkinson's Disease.

Treatments for Parkinson's Disease include drugs such as levodopa and the dopamine agonists ropinirole, pramipexole, and pergolide can reduce muscle rigidity, improve speed and coordination of movement, and relieve tremor. Cell transplantation (e.g., embryonic stem cells and, adult stem cells) may also be a useful therapy for Parkinson's Disease. Any one or more of these treatments can be used in combination with a TWEAK/TWEAK-R blocking agent.

Symptoms of Parkinson's Disease usually appear after 80 percent or more of the dopamine-producing neurons in the substantia nigra have died, which significantly narrows the window of opportunity for preventive or protective treatments. The course of the disease varies widely. Some people have mild symptoms for many years, while others have severe symptoms and a quicker progression. A TWEAK/TWEAK-R blocking agent can be administered to subjects who show a depletion of dopamine producing neurons in the substantia nigra, e.g., a less than 80, 60, 40, or 30% depletion.

The efficacy and dosing of a TWEAK/TWEAK-R blocking agent can be evaluated in an animal model of Parkinson's Disease, e.g., treatment with 1-methyl-phenyl-1,2,3,6-tetrallydropyridine (MPTP). MPTP is a neurotoxin that damages nigrostriatal dopaminergic neurons in several mammalian species, including mice, and produces a Parkinsonian syndrome in humans and primates (U.S. Pat. No. 6,630,514). Another animal model of Parkinson's Disease is transgenic mice overexpressing human α-synucleire Neuronal expression of human α-synuelein results in progressive accumulation of α-syrtuelein and ubiquitin-immunoreactive inclusions in neurons in the neocortex, hippocampus, and substantia nigra. These alterations are associated with loss of dopaminergic terminals in the basal ganglia and with motor impairments. (Masliah et al. (2000) *Science* 287: 1265-1269).

Huntington's Disease

A TWEAK/TWEAK-R blocking agent can be administered to treat Huntington's Disease (HD), which results from genetically-programmed degeneration of neurons in certain areas of the brain. HD is a genetic disease that is characterized by a generational expansion in the number of trinucleotide repeats in the gene encoding Huntingtin.

A TWEAK/TWEAK-R blocking agent can be used to delay onset, reduce severity, and reduce the rate of progression of Huntington's Disease. The agent can be used to treat long-term survivors as well as patients who exhibit more rapid disease progression. The agent can be administered to subjects that have a trinucleotide repeat length greater than 30, 35, 40, 45, or 50.

Some early symptoms of HD are mood swings; depression; irritability; or trouble driving, learning new things, remembering a fact, or making a decision. As the disease progresses, concentration on intellectual tasks becomes increasingly difficult and the patient may have difficulty feeding himself or herself and swallowing. A TWEAK/TWEAK-R blocking agent can be used to ameliorate one or more these symptoms, or to reduce the rate of disease progression. The blocking agent can also be administered at any stage, e.g., prior to the display of any symptoms, at a stage characterized by early symptoms, or at a later stage.

A genetic test, coupled with a complete medical history and neurological and laboratory tests, can be used to diagnose HD. Presymptomic testing is available for individuals who are at risk for carrying the mutated gene. In 1 to 3 percent of individuals with HD, no family history of HD can be found. In some implementations, subjects who are the progeny of Huntington disease patient or of a carrier of a Huntington's Disease mutation, or who are identified as having Huntington's Disease (e.g., by a genetic test), are given a prophylactic dose of a TWEAK/TWEAK-R blocking agent, e.g., prior to showing physical symptoms of Huntington's Disease.

A variety of methods are available to evaluate and/or monitor Huntington's Disease. A variety of clinical symptoms and indicia for the disease are known, Huntington's Disease causes a movement disorder, psychiatric difficulties, and cognitive changes. The degree, age of onset, and manifestation of these symptoms can vary. The movement disorder can include quick, random, dance-like movements called chorea.

One method for evaluating Huntington's Disease uses the Unified Huntington's Disease Rating Scale (UNDRS). It is also possible to use individual tests alone or in combination to evaluate if at least one symptom of Huntington's Disease is ameliorated. The UNDRS is described in *Movement Disorders* (vol. 11:136-142, 1996) and Marder et al. ((2000) *Neurology* 54:452-458). The UNDRS quantifies the severity of Huntington's Disease. It is divided into multiple subsections: motor, cognitive, behavioral, and functional. In one embodiment, a single subsection is used to evaluate a subject. These scores can be calculated by summing the various questions of each section. Some sections (such as chorea and dystonia) can include grading each extremity, face, bucco-oral-ligual, and trunk separately.

Exemplary motor evaluations include: ocular pursuit, saccade initiation, saccade velocity, dysarthria, tongue protrusion, finger tap ability, pronate/supinate, a fist-hand-palm sequence, rigidity of arms, bradykinesia, maximal dystonia (trunk, upper and lower extremities), maximal chorea (e.g., trunk, face, upper and lower extremities), gait, tandem walking, and retropulsion. An exemplary treatment can cause a change in the Total Motor Score 4 (TMS-4), a subscale of the UHDRS, e.g., over a one-year period.

Additional therapies include administering; bromocriptine, serotonin antagonists (e.g., tetrabenazin), tiapride (e.g., TIAPRIDAL®), or a NMDA receptor blocker. Any one or more of these treatments can be used in combination with a TWEAK/TWEAK-R blocking agent.

A number of animal model systems for Huntington's Disease are available. See, e.g., Brouillet (2000) *Functional Neurology* 15(0239-251; Ona et al. (1999) *Nature* 399:263-267; Bates et al, (1997) *Hum. Mol. Genet,* 6(10):1633-1637; Hausson et al. (2001) *J. Neurochem,* 78:694-703; and Rubinsztein (2002) *Trends Genet,* 18202-209 (a review on various animal and non-human models of HD).

Transgenic mice can be produced that express (in at least one cell) a human Huntingtin protein, a portion thereof, or fusion protein comprising human Huntingtin protein, or a portion thereof, with, for example, at least 36 giutamines (e.g., encoded by CAG repeats (alternatively, any number of the CAG repeats may be CAA) in the CAG repeat segment of exon 1 encoding the polyglutamine tract).

An example of such a transgenic mouse strain is the R6/2 line (Mangiarini et al. (1996) *Cell* 87:493-506). The R6/2 mice are transgenic Huntington's Disease mice, which overexpress exon 1 of the human Huntingtin gene (under the control of the endogenous promoter). The exon 1 of the R6/2 human Huntingtin gene has expanded CAG/polyglutamine repeat lengths (150 CAG repeats on average). These mice develop a progressive, ultimately fatal, neurological disease with many features of human Huntington's Disease. Abnormal aggregates, constituted in part by the N-terminal part of Huntingtin (encoded by HD exon 1), are observed in R6/2 mice, both in the cytoplasm and nuclei of cells (Davies et al. (1997) *Cell* 90:537-548). For example, the human Huntingtin protein in the transgenic animal is encoded by a gene that includes at least 55 CAG repeats and more preferably about 150 CAG repeats.

The transgenic animals can develop a Huntington's Disease-like phenotype. These transgenic mice are characterized by reduced weight gain, reduced lifespan, and motor impairment characterized by abnormal gait, resting tremor, hindlimb clasping, and hyperactivity from 8 to 10 weeks after birth (for example the R6/2 strain; see Mangiarini at al. (1996) *Cell* 87:493-506), The phenotype worsens progressively toward hypokinesia. The brains of these transgenic mice also demonstrate neurochemical and histological abnormalities, such as changes in neurotransmitter receptors (glutamate, dopaminergic), decreased concentration of N-acetylaspartate marker of neuronal integrity), and reduced striatum and brain size. Accordingly, evaluating can include assessing parameters related to neurotransmitter levels, neurotransmitter receptor levels, brain, size, and striatum size. In addition, abnormal aggregates containing the transgenic part of or full-length human Huntingtin protein are present in the brain tissue of these animals (e.g., the R6/2 transgenic mouse strain). See, e.g., Mangiarini et al. (1996) *Cell* 87493-506; Davies et al. (1997) *Cell* 90:537-548; Brouillet (2000) *Functional Neurol.* 15(4):239-251; and Cha et al. (1998) *Proc. Natl. Acad. Sci. USA* 95:6480-6485.

Alzheimer's Disease

A TWEAK/TWEAK-R blocking agent can be administered to treat Alzheimer's Disease (AD), which is a progressive, neurodegenerative disease characterized in the brain by abnormal clumps (amyloid plaques) and tangled bundles of fibers (neurofibrillary tangles) composed of misplaced proteins. A TWEAK/TWEAK-R blocking agent can be used to delay onset, reduce severity, and reduce the rate of progression of Alzheimer's Disease. The agent can be used to treat long-term survivors as well as patients who exhibit more rapid disease progression. The severity and progression of, and improvement in, Alzheimer's Disease can be assessed by a number of criteria, including Activities of Daily Living scales, one of which is the Progressive Deterioration Scale (PDS), in which 29 questions are used to determine a patient's ability to perform functions such as interacting socially, travelling without getting lost, coping when the caregiver is away, and identifying or using common household objects such as telephones; the Mini-Mental State Examination (MMSE), which is a short collection of cognitive tests that examines several areas of coition and is easy to administer and score and is widely used to measure the onset, progression and severity of Alzheimer's Disease.

Age is the most important risk factor for AD; the number of people with the disease doubles every 5 years beyond age 65. Three genes have been discovered that cause early onset (familial) AD. Other genetic mutations that cause excessive accumulation of amyloid protein are associated with age-related (sporadic) AD. In some implementations, subjects who are the progeny of an AD patient or of a carrier of a mutation in a gene tied to AD, or who are identified as having Alzheimer's Disease (e.g., by a genetic test), are given a prophylactic dose of a TWEAK/TWEAK-R blocking agent, e.g., prior to showing physical symptoms of AD.

Symptoms of AD include memory loss, language deterioration, impaired ability to mentally manipulate visual information, poor judgment, confusion, restlessness, and mood swings. Eventually AD destroys cognition, personality, and the ability to function. The early symptoms of AD, which include forgetfulness and loss of concentration, are often missed because they resemble natural signs of aging. AD is a progressive disease, but its course can vary from 5 to 20 years. A TWEAK/TWEAK-R blocking agent can be used to ameliorate one or more these symptoms, or to reduce the rate of disease progression. Treatments for AD include tacrine (COGNEX®), donepezil (ARICEPT®), rivastigmine (EXELON®), and galantamine (REMINYL®), memantine (NAMENDA™), other drugs that may affect AD progression include nonsteroidal anti-inflammatory drugs (NSAIDS), statins, folic acid, gingko biloba, and vitamins E, B6, and B12. Any one or more of these treatments can be used in combination with a TWEAK/TWEAK-R blocking agent.

The efficacy and dosing of a TWEAK/TWEAK-R blocking agent can be evaluated in an animal model of AD, e.g., a transgenic mouse model of AD. For example, transgenic mice expressing a human or mouse APP or presenilin can be used. Some of these transgenic mice develop a progressive neurologic disorder generally is within a year from birth (see, e.g., U.S. Pat. Nos. 5,877,399; 6,037,521; 5,894,078; 5,850,003; and 5,898,094). Certain transgenic animal models have been described, for example, in U.S. Pat. Nos. 5,612,486; 5,387,742; 5,720,936; 5,877,015; and 5,811,633; and in Ganes et al. (1995) *Nature* 373:523. Preferred are animals that exhibit characteristics associated with the pathophysiology of AD. Administration of inhibitors to the transgenic mice described herein provides an alternative method for demonstrating the inhibitory activity of the compounds. Administration of the compounds in a pharmaceutically effective carrier and via an administrative route that reaches the target tissue in an appropriate therapeutic amount is also preferred.

Pharmaceutical Compositions

A TWEAK/TWEAK-R blocking agent (e.g., an antibody or a soluble TWEAK-R protein, e.g., TWEAK-R-Fc) can be formulated as a pharmaceutical composition, e.g., for administration to a subject to treat a neuronal disorder such as a mechanical neuronal trauma (e.g., SCI or TBI), a neurodegenerative disorder (e.g., ALS, Parkinson's Disease, Huntington's Disease, or Alzheimer's Disease), or other disorder described herein. Typically, a pharmaceutical composition includes a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. The composition can include a pharmaceutically acceptable salt, e.g., an acid addition salt or a base addition salt (see, e.g., Berge, S. M. et al. (1977) *J. Pharm. Sci.* 66:1-19).

The TWEAK/TWEAK-R blocking agent can be formulated according to standard methods. Pharmaceutical formulation is a well-established art, and is further described, e.g., in Gennaro (ed.), *Remington: The Science and Practice of Pharmacy*, 20$^{th}$ ed., Lippincott, Williams & Wilkins (2000) (ISBN: 0683306472); Ansel et al., *Pharmaceutical Dosage Forms and Drug Delivery Systems*, 7$^{th}$ Ed., Lippincott Williams & Wilkins Publishers (1999) (ISBN: 0683305727); and Kibbe (ed.), *Handbook of Pharmaceutical Excipients American Pharmaceutical Association*, 3$^{rd}$ ed. (2000) (ISBN: 091733096X).

In one embodiment, the TWEAK/TWEAK-R blocking agent (e.g., an antibody or TWEAK-R-Fc) can be formulated with excipient materials, such as sodium chloride, sodium dibasic phosphate heptahydrate, sodium monobasic phosphate, and a stabilizer. It can be provided, for example, in a buffered solution at a suitable concentration and can be stored at 2-8° C.

The pharmaceutical compositions may be in a variety of forms. These include, for example, liquid, semi-solid and solid dosage forms, such as liquid solutions (e.g., injectable and infusible solutions), dispersions or suspensions, tablets, pills, powders, liposomes, and suppositories. The preferred form can depend on the intended mode of administration and therapeutic application. Typically compositions for the agents described herein are in the form of injectable or infusible solutions.

Such compositions can be administered by a parenteral mode (e.g., intravenous, subcutaneous, intraperitoneal, or intramuscular injection). The phrases "parenteral administration" and "administered parenterally" as used herein mean modes of administration other than enteral and topical administration, usually by injection, and include, without limitation, intravenous, intramuscular, intraarterial, intrathecal, intracapsular, intraorbital, intracardiac, intradermal, intraperitoneal, transtracheal, subcutaneous, subeuticular, intraarticular, subcapsular, subarachnoid, intraspinal, epidural, and intrasternal injection and infusion.

The composition can be formulated as a solution, microemulsion, dispersion, liposome, or other ordered structure suitable for stable storage at high concentration. Sterile injectable solutions can be prepared by incorporating an agent described herein in the required amount in an appropriate solvent with one or a combination of ingredients enumerated above, as required, followed by filtered sterilization. Generally, dispersions are prepared by incorporating an agent described herein into a sterile vehicle that contains a basic dispersion medium and the required other ingredients from those enumerated above. In the case of sterile powders for the preparation of sterile injectable solutions, the preferred methods of preparation are vacuum drying and freeze drying that yields a powder of an agent described herein plus any additional desired ingredient from a previously sterile-filtered solution thereof. The proper fluidity of a solution can be maintained, for example, by the use of a coating such as lecithin, by the maintenance of the required particle size in the case of dispersion, and by the use of surfactants. Prolonged absorption of injectable compositions can be brought about by including in the composition an agent that delays absorption, for example, monostearate salts and gelatin.

In certain embodiments, the TWEAK/TWEAK-R blocking agent may be prepared with a carrier that will protect the compound against rapid release, such as a controlled release formulation, including implants, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known. See, e.g., *Sustained and Controlled Release Drug Delivery Systems*, J. R. Robinson, ed., Marcel Dekker, Inc., New York, 1978.

A TWEAK/TWEAK-R blocking agent (e.g., an antibody or a soluble TWEAK receptor protein) can be modified, e.g., with a moiety that improves its stabilization and/or retention in circulation, e.g., in blood, serum, or other tissues, e.g., by at least 1.5, 2, 5, 10, or 50-fold. The modified blocking agent can be evaluated to assess whether it can reach sites of neuronal damage, e.g., after a trauma or during the course of a neurological disorder (e.g., by using a labeled form of the blocking agent).

For example, the TWEAK/TWEAK-R blocking agent (e.g., an antibody or a soluble TWEAK receptor protein) can be associated with (e.g., conjugated to) a polymer, e.g., a substantially non-antigenic polymer, such as a polyalkylene oxide or a polyethylene oxide. Suitable polymers will vary substantially by weight. Polymers having molecular number average weights ranging from about 200 to about 35,000 Daltons (or about 1,000 to about 15,000, and 2,000 to about 12,500) can be used.

For example, a TWEAK or a TWEAK receptor binding antibody can be conjugated to a water-soluble polymer, e.g., a hydrophilic polyvinyl polymer, e.g., polyvinylalcohol or polyvinylpyrrolidone. A non-limiting list of such polymers includes polyalkylene oxide homopolymers such as polyethylene glycol (PEG) or polypropylene glycols, polyoxyethylenated polyols, copolymers thereof and block copolymers thereof, provided that the water solubility of the block copolymers is maintained. Additional useful polymers include polyoxyalkylenes such as polyoxyethylene, polyoxypropylene, and block copolymers of polyoxyethylene and polyoxypropylene (Pluronics); polymethacrylates; carbomers; and branched or unbranched polysaccharides.

When the TWEAK/TWEAK-R blocking agent (e.g., an antibody or a soluble TWEAK-R protein) is used in combination with a second agent, the two agents can be formulated separately or together. For example, the respective pharmaceutical compositions can be mixed, e.g., just prior to administration, and administered together or can be administered separately, e.g., at the same or different times.

Administration

The TWEAK/TWEAK-R blocking agent (e.g., an antibody or a soluble TWEAK-R protein) can be administered to a subject, e.g., a human subject, by a variety of methods. For many applications, the route of administration is one of: intravenous injection or infusion (IV), subcutaneous injection (SC), intraperitoneally (IP), or intramuscular injection. In some cases, administration may be directly into the CNS, e.g., intrathecal or intracerebroventricular (ICV). The blocking agent can be administered as a fixed dose, or in a mg/kg dose.

The dose can also be chosen to reduce or avoid production of antibodies against the TWEAK/TWEAK-R blocking agent.

The route and/or mode of administration of the blocking agent can also be tailored for the individual case, e.g., by monitoring the subject, e.g., using tomographic imaging, neurological exam, and standard parameters associated with the particular disorder, e.g., criteria for assessing SCI, TBI, ALS, Parkinson's Disease, Huntington's Disease, or Alzheimer's Disease.

Dosage regimens are adjusted to provide the desired response, e.g., a therapeutic response or a combinatorial therapeutic effect. Generally, any combination of doses (either separate or co-formulated) of the TWEAK/TWEAK-R blocking agent (e.g., an antibody) (and optionally a second agent) can be used in order to provide a subject with the agent in bioavailable quantities. For example, doses in the range of 1 mg/kg-100 mg/kg, 0.5-20 mg/kg, or 1-10 mg/kg can be administered. Other doses can also be used.

Dosage unit form or "fixed dose" as used herein refers to physically discrete units suited as unitary dosages for the subjects to be treated; each unit contains a predetermined quantity of active compound calculated to produce the desired therapeutic effect in association with the required pharmaceutical carrier and optionally in association with the other agent, if used.

The TWEAK/TWEAK-R blocking agent may be administered at least once between about 10 minutes to about 48 hours, more preferably between about 10 minutes and 24 hours, more preferably within 3 hours, after the onset of symptoms or manifestation of a neuronal or other injury or pathology. For example, the agent may be administered to a patient suffering or at risk for a disorder described herein, e.g., SCI, TBI, ALS, Parkinson's Disease, Huntington's Disease, or Alzheimer's Disease. Single or multiple dosages may be given. Alternatively, or in addition, the blocking agent may be administered via continuous infusion. The treatment can continue for days, weeks, months or even years so as to minimize brain or spinal cord damage from the injury or disorder, to minimize damage from post-injury inflammatory events, and/or to prevent or minimize damage that might result from disease progression.

The TWEAK/TWEAK-R blocking agent can be administered, e.g., once or twice daily or about one to four times per week, e.g., for between about 1 to 10 weeks, preferably between 2 to 8 weeks, more preferably between about 3 to 7 weeks, and even more preferably for about 4, 5, or 6 weeks. The TWEAK/TWEAK-R blocking agent can be administered for months (e.g., 6, 12, 18, 24 or 36 months) or years (e.g., 1, 2, 3, 5, 10, or 15 years), e.g., to treat or prevent a degenerative disorder described herein. The skilled artisan will appreciate that certain factors may influence the dosage and timing required to effectively treat a subject, including but not limited to the severity of the disease or disorder, formulation, previous treatments, the general health and/or age of the subject, and other diseases present. Moreover, treatment of at subject with a therapeutically effective amount of a compound can include a single treatment or, preferably, can include a series of treatments. Animal models can also be used to determine a useful dose, e.g., an initial dose or a regimen.

If a subject is at risk for developing a neurodegenerative or other disorder described herein or an injury to the brain or spinal cord (e.g., SCI, TBI), the blocking agent can be administered before the onset of an injury or disorder as a preventative measure. The duration of such preventative treatment can be a single dosage of the blocking agent or the treatment may continue (e.g., multiple dosages). For example, a subject at risk for the disorder or who has a predisposition for the disorder may be treated with the blocking agent for days, weeks, months, or even years so as to prevent the injury or disorder from occurring.

Surgery in or near the brain or spinal cord can put a subject at risk for SCI or TBI. The blocking agent can be administered prior to, during, and after such surgery in or near the brain or spinal cord, e.g., to minimize neuronal damage caused by the surgery as well as pre- or postoperative events.

A pharmaceutical composition may include a "therapeutically effective amount" of an agent described herein. Such effective amounts can be determined based on the effect of the administered agent, or the combinatorial effect of agents if more than one agent is used. A therapeutically effective amount of an agent may also vary according to factors such as the disease state, age, sex, and weight of the individual, and the ability of the compound to elicit a desired response in the individual, e.g., amelioration of at least one disorder parameter or amelioration of at least one symptom of the disorder. A therapeutically effective amount is also one in which any toxic or detrimental effects of the composition are outweighed by the therapeutically beneficial effects.

Devices and Kits

Pharmaceutical compositions that include the TWEAK/TWEAK-R blocking agent (e.g., an antibody or soluble TWEAK-R) can be administered with a medical device. The device can designed with features such as portability, room temperature storage, and ease of use so that it can be used in emergency situations, e.g., by an untrained subject or by emergency personnel in the field, removed to medical facilities and other medical equipment. The device can include, e.g., one or more housings for storing pharmaceutical preparations that include TWEAK/TWEAK-R blocking agent, and can be configured to deliver one or more unit doses of the blocking agent.

For example, the pharmaceutical composition can be administered with a needleless hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. Many other devices, implants, delivery systems, and modules are also known.

A TWEAK/TWEAK-R blocking agent (e.g., an antibody or soluble TWEAK-R protein) can be provided in a kit. In one embodiment, the kit includes (a) a container that contains a composition that includes a TWEAK or a TWEAK receptor blocking agent, and optionally (b) informational material. The informational material can be descriptive, instructional, marketing or other material that relates to the methods described herein and/or the use of the agents for therapeutic benefit. In an embodiment, the kit also includes a second agent for treating a neuronal disorder such as a mechanical neuronal trauma (e.g., SCI or TBI), a neurodegenerative disorder (e.g., ALS, Parkinson's Disease, Huntington's Disease, or Alzheimer's Disease), or other disorder described herein. For example, the kit includes a first container that contains a composition that includes the TWEAK/TWEAK-R blocking agent, and a second container that includes the second agent.

The informational material of the kits is not limited in its form. In one embodiment, the informational material can include information about production of the compound, molecular weight of the compound, concentration, date of expiration, batch or production site information, and so forth. In one embodiment, the informational material relates to methods of administering the TWEAK/TWEAK-R blocking agent (e.g., an antibody or a soluble TWEAK-R protein), e.g., in a suitable dose, dosage form, or mode of administration (e.g., a dose, dosage form, or mode of administration described herein), to treat a subject who has had or who is at risk for a neuronal disorder such as a mechanical neuronal trauma (e.g., SCI or TBI), a neurodegenerative disorder (e.g., ALS, Parkinson's Disease, Huntington's Disease, or Alzheimer's Disease), or other disorder described herein. The information can be provided in a variety of formats, including printed text, computer readable material, video recording, audio recording, or information that provides a link or address to substantive material located on the world wide web.

In addition to the blocking agent, the composition in the kit can include other ingredients, such as a solvent or buffer, a stabilizer, or a preservative. The blocking agent can be provided in any forme e.g., liquid, dried, or lyophilized form, preferably substantially pure and/or sterile. When the agent is provided in a liquid solution, the liquid solution preferably is an aqueous solution. When the agent is provided as a dried form, reconstitution generally is by the addition of a suitable solvent. The solvent, e.g., sterile water or buffer, can optionally be provided in the kit.

The kit can include one or more containers for the composition or compositions containing the agent. In some embodiments, the kit contains separate containers, dividers, or compartments for the composition and informational material. For example, the composition can be contained in a bottle, vial, or syringe, and the informational material can be contained in a plastic sleeve or packet. In other embodiments, the separate elements of the kit are contained within a single, undivided container. For example, the composition is contained in a bottle, vial, or syringe that has attached thereto the informational material in the form of a label. In some embodiments, the kit includes a plurality (e.g., a pack) of individual containers, each containing one or more unit dosage forms (e.g., a dosage form described herein) of the agent. The containers can include a combination unit dosage, e.g., a unit that includes both the TWEAK or a TWEAK receptor blocking agent and the second agent, e.g., in a desired ratio. For example, the kit includes a plurality of syringes, ampules, foil packets, blister packs, or medical devices, e.g., each containing a single combination unit dose. The containers of the kits can be air tight, waterproof (e.g., impermeable to changes in moisture or evaporation), and/or light-tight.

The kit optionally includes a device suitable for administration of the agent (e.g., in a pharmaceutical composition), e.g., a syringe or other suitable delivery device. The device can be provided pre-loaded with one or a combination of agents or can be empty, but suitable for loading.

Nucleic Acid and Protein Analysis

Numerous methods for detecting TWEAK or a TWEAK-R protein and nucleic acid are available to the skilled artisan, including antibody-based methods for protein detection (e.g., Western blot or ELISA), and hybridization-based methods for nucleic acid detection (e.g., PCR or Northern blot).

Arrays are particularly useful molecular tools for characterizing a sample, e.g., a sample from a subject. For example, an array having capture probes for multiple genes, including probes for TWEAK and a TWEAK receptor, or for multiple proteins, can be used in a method described herein. Altered expression of TWEAK or TWEAK receptor nucleic acids and/or protein can be used to evaluate a sample, e.g., a sample from a subject, e.g., to evaluate, a disorder described herein.

Arrays can have many addresses, e.g., locatable sites, on a substrate. The featured arrays can be configured in a variety of formats, non-limiting examples of which are described below. The substrate can be opaque, translucent, or transparent. The addresses can be distributed, on the substrate in one dimension, e.g., a linear array; in two dimensions, e.g., a planar array; or in three dimensions, e.g., a three-dimensional array. The solid substrate may be of any convenient shape or form, e.g., square, rectangular, ovoid, or circular.

Arrays can be fabricated by a variety of methods, e.g., photolithographic methods (see, e.g., U.S. Pat. Nos. 5,143,854; 5,510,270; and 5,527,681), mechanical methods (e.g., directed-flow methods as described in U.S. Pat. No. 5,384,261), pin-based methods (e.g., as described in U.S. Pat. No. 5,288,514), and bead-based techniques (e.g., as described in PCT App, US/93/04145).

The capture probe can be a single-stranded nucleic acid, a double-stranded nucleic acid (e.g., which is denatured prior to or during hybridization), or a nucleic acid having a single-stranded region and a double-stranded region. Preferably, the capture probe is single-stranded. The capture probe can be selected by a variety of criteria, and preferably is designed by a computer program with optimization parameters. The capture probe can be selected to hybridize to a sequence rich (e.g., non-homopolymeric) region of the gene. The $T_m$ of the capture probe can be optimized by prudent selection of the complementarity region and length. Ideally, the $T_m$ of all capture probes on the array is similar, e.g., within 20, 10, 5, 3, or 2° C. of one another.

The isolated nucleic acid is preferably mRNA that can be isolated by routine methods, e.g., including DNase treatment to remove genomic DNA and hybridization to an oligo-dT coupled solid substrate (e.g., as described in *Current Protocols in Molecular Biology*, John Wiley & Sons, N.Y). The substrate is washed and the mRNA is eluted.

The isolated mRNA can be reversed transcribed and optionally amplified, e.g., by rtPCR, e.g., as described in U.S. Pat. No. 4,683,202. The nucleic acid can be an amplification product, e.g., from PCR (U.S. Pat. Nos. 4,683,196 and 4,683,202); rolling circle amplification ("RCA," U.S. Pat. No. 5,714,320), isothermal RNA amplification or NASBA (U.S. Pat. Nos. 5,130,238; 5,409,818; and 5,554,517), and strand displacement amplification (U.S. Pat. No. 5,455,166). The nucleic acid can be labeled during amplification, by the incorporation of a labeled nucleotide. Examples of preferred labels include fluorescent labels, e.g., red-fluorescent dye Cy5 (Amersham) or green-fluorescent dye Cy3 (Amersham), and chemiluminescent labels, e.g., as described in U.S. Pat. No. 4,277,437. Alternatively, the nucleic acid can be labeled with biotin, and detected after hybridization with labeled streptavidin, e.g., streptavidin-phycoerythrin (Molecular Probes).

The labeled nucleic acid can be contacted to the array. In addition, a control nucleic acid or a reference nucleic acid can be contacted to the same array. The control nucleic acid or reference nucleic acid can be labeled with a label other than the sample nucleic acid, one with a different emission maximum. Labeled nucleic acids can be contacted to an array under hybridization conditions. The array can be washed and then imaged to detect fluorescence at each address of the array.

The expression level of a TWEAK or TWEAK-R protein can be determined using an antibody specific for the polypeptide (e.g., using a Western blot or an ELISA assay). Moreover, the expression levels of multiple proteins, including TWEAK and a TWEAK receptor, can be rapidly determined in parallel using a polypeptide array having antibody capture probes for each of the polypeptides. Antibodies specific for a polypeptide can be generated by a method described herein (see "Antibody Generation"). The expression level of a TWEAK or TWEAK receptor can be measured in a subject (e.g., in vivo imaging) or in a biological sample from a subject (e.g., blood, serum, plasma, or cerebral spinal fluid).

A low-density (96-well format) protein array has been developed in which proteins are spotted onto a nitrocellulose membrane (Ge (2000) *Nucleic. Acids Res.* 28, e3, I-VII). A high-density protein array (100,000 samples within 222×222 mm) used for antibody screening was formed by spotting proteins onto polyvinylidene difluoride (PVDF) (Lueking et al. (1999) *Anal. Biochem*, 270:103-111), See also, e.g., Mendoza et al. (1999) *Biotechniques* 27:778-788; MacBeath and Schreiber (2000) *Science* 289:1760-1763; and De Wildt et al. (2000) *Nat. Biotech,* 18:989-994. These art-known methods and others can be used to generate an array of antibodies for detecting the abundance of polypeptides in a sample. The sample can be labeled, e.g., biotinylated, for subsequent detection with streptavidin coupled to a fluorescent label. The array can then be scanned to measure binding at each address.

The nucleic acid and polypeptide arrays of the invention can be used in a wide variety of applications. For example, the arrays can be used to analyze a patient sample. The sample is compared to data obtained previously, e.g., known clinical specimens or other patient samples. Further, the arrays can be used to characterize a cell culture sample, e.g., to determine a cellular state after varying a parameter, e.g., exposing the cell culture to an antigen, a transgene, or a test compound.

The expression data can be stored in a database, e.g., a relational database such as a SQL database (e.g., Oracle or Sybase database environments). The database can have multiple tables. For example, raw expression data can be stored in one table, wherein each column corresponds to a gene being assayed, e.g., an address or an array, and each row corresponds to a sample. A separate table can store identifiers and sample information, e.g., the batch number of the array used, date, and other quality control information.

Expression profiles obtained from gene expression analysis on an array can be used to compare samples and/or cells in a variety of states as described in Golub et al. ((1999) *Science* 286:531). In one embodiment, expression (e.g., mRNA expression or protein expression) information for a gene encoding TWEAK and/or a gene encoding a TWEAK receptor are evaluated, e.g., by comparison to a value, e.g., a reference value. Reference values can be obtained from a control, e.g., a reference subject. Reference values can also be obtained from statistical analysis, e.g., to provide a reference value for a cohort of subjects, e.g., age and gender matched subjects, e.g., normal subjects or subjects who have sustained a neuronal or other injury or pathology in the brain or spinal cord or who have a disorder described herein. Statistical similarity to a particular reference (e.g., to a reference for a risk-associated cohort) or a normal cohort can be used to provide an assessment (e.g., an indication of risk of neuronal injury or a neurological disorder) to a subject, e.g., a subject who has not sustained a prior neuronal or other injury to the brain or spinal cord, a subject who has not been diagnosed with a disorder described herein, a subject who has a risk for a neuronal disorder such as a neurodegenerative disorder (e.g., ALS, Parkinson's Disease, Huntington's Disease, or Alzheimer's Disease), or other disorder described herein (e.g., a genetic predisposition) or a risk for a disorder described herein, or a subject who has sustained a neuronal or other injury to the brain or spinal cord.

Subjects suitable for treatment can also be evaluated for expression and/or activity of TWEAK and/or a TWEAK receptor. Subjects can be identified as suitable for treatment if the expression and/or activity for TWEAK and/or a TWEAK receptor is elevated relative to a reference, e.g., reference value, e.g., a reference value associated with normal.

Subjects who are being administered an agent described herein or other treatment for a neuronal disorder such as a mechanical neuronal trauma (e.g., SCI or TBI), a neurodegenerative disorder (e.g., ALS, Parkinson's Disease, Huntington's Disease, or Alzheimer's Disease), or other disorder described herein, can be evaluated as described for expression and/or activity of TWEAK and/or a TWEAK receptor. The subject can be evaluated at multiple times, e.g., at multiple times during a course of therapy, e.g., during a therapeutic regimen. Treatment of the subject can be modified depending on how the subject is responding to the therapy. For example, a reduction in TWEAK and/or TWEAK receptor expression or activity can be indicative of responsiveness.

Particular effects mediated by an agent may show a difference (e.g., relative to an untreated subject, control subject, or other reference) that is statistically significant (e.g., P value<0.05 or 0.02). Statistical significance can be determined by any art known method. Exemplary statistical tests include: the Students T-test, Mann Whitney U non-parametric test, and Wilcoxon non-parametric statistical test. Some statistically significant relationships have a P value of less than 0.05 or 0.02.

In Vivo Imaging

TWEAK and/or TWEAK-R blocking agents (e.g., antibodies) provide a method for detecting the presence of TWEAK and/or a TWEAK receptor (e.g., Fn14) in vivo (e.g., in viva imaging in a subject), respectively. The method can be used to evaluate (e.g., diagnose, localize, or stage) a condition or a neuronal disorder such as a mechanical neuronal trauma (e.g., SCI or TRI), a neurodegenerative disorder (e.g., ALS, Parkinson's Disease, Huntington's Disease, or Alzheimer's Disease), or other disorder described herein. The method includes: (i) administering to a subject (and optionally a control subject) a TWEAK or TWEAK receptor binding agent (e.g., a blocking agent that binds to TWEAK or a TWEAK receptor, e.g., an antibody or antigen binding fragment thereof, although such agents need not be blocking agents), under conditions that allow interaction of the binding agent and TWEAK or a TWEAK receptor to occur; and (ii) detecting localization of the binding agent in the subject. The method can be used to detect the location of TWEAK or TWEAK receptor expressing cells. A statistically-significant increase in the amount of the complex in the subject relative to the reference, e.g., the control subject or subject's baseline, can be a factor that may lead to a diagnosis of neuronal or other injury or pathology in the brain or spinal cord or of a neurological disorder or risk for such an injury or disorder.

Preferably, the TWEAK and for TWEAK receptor binding agent used in the in vivo (and also in vitro) diagnostic methods is directly or indirectly labeled with a detectable substance to facilitate detection of the bound or unbound binding agent. Suitable detectable substances include various enzymes, prosthetic groups, fluorescent materials, luminescent materials and radioactive materials. In one embodiment, the TWEAK or TWEAK-R binding protein is coupled to a radioactive ion, e.g., indium ($^{111}$In), iodine ($^{131}$I or $^{125}$I), yttrium ($^{90}$Y), actinium ($^{225}$Ac), bismuth ($^{212}$Bi or $^{213}$Bi), sulfur ($^{35}$S), carbon ($^{14}$C), tritium ($^{3}$H), rhodium ($^{188}$Rh), or phosphorous ($^{32}$P). In another embodiment, the TWEAK/TWEAK-R binding protein is labeled with an NMR contrast agent.

In one aspect, the invention features a method of imaging vasculature in a patient who is at risk for neuronal or other injury or pathology in the brain or spinal cord or for developing a neurological disorder (e.g., a neurodegenerative disorder), has experienced such an injury, and/or has a neuronal or other disorder of the brain or spinal cord. The method includes: providing an agent that binds to TWEAK or a TWEAK receptor, e.g., an agent described herein, wherein the protein is physically associated to an imaging agent; administering the agent to a patient, e.g., with a risk for neuronal or other injury to the brain or spinal cord; or for a neurological disorder and imaging the patient, e.g., to detect TWEAK or TWEAK receptor expressing cells.

Methods of Evaluating Genetic Material

There are numerous methods for evaluating genetic material to provide genetic information. These methods can be used to evaluate a genetic locus that includes a gene encoding TWEAK or a gene encoding a TWEAK receptor, as well as other loci. The methods can be used to evaluate one or more nucleotides, e.g., a coding or non-coding region of the gene, e.g., in a regulatory region (e.g., a promoter, a region encoding an untranslated region or intron, and so forth).

Nucleic acid samples can be analyzed using biophysical techniques (e.g., hybridization, electrophoresis, and so forth), sequencing, enzyme-based techniques, and combinations thereof. For example, hybridization of sample nucleic acids to nucleic acid microarrays can be used to evaluate sequences in an mRNA population and to evaluate genetic polymorphisms. Other hybridization-based techniques include sequence specific primer binding (e.g., PCR or LCR); Southern analysis of DNA, e.g., genomic DNA; Northern analysis of RNA, e.g., mRNA; fluorescent probe-based techniques (sec, e.g., Beaudet et al. (2001) *Genome Res.* 11(4):600-608); and allele specific amplification. Enzymatic techniques include, restriction enzyme digestion; sequencing; and single base extension (SBE). These and other techniques are well known to those skilled in the art.

Electrophoretic techniques include capillary electrophoresis and Single-Strand Conformation Polymorphism (SSCP) detection (see, e.g., Myers et al. (1985) *Nature* 313:495-498 and Ganguly (2002) *Hum Mutat.* 19(4)334-342). Other biophysical methods include denaturing high pressure liquid chromatography (DHPLC).

In one embodiment, allele specific amplification technology that depends on selective PCR amplification may be used to obtain genetic information. Oligonucleotides used as primers for specific amplification may carry the mutation of interest in the center of the molecule (so that amplification depends on differential hybridization) (Gibbs et al (1989) *Nucl. Acids Res.* 17:2437-2448) or at the extreme 3' end of one primer where, under appropriate conditions, mismatch can prevent, or reduce, polymerase extension (Prosser (1993) *Trends Biotechnol.* 11:238-246). In addition, it is possible to introduce a restriction site in the region of the mutation to create cleavage-based detection (Gasparini et al., (1992) *Mol. Cell Probes* 6:1). In another embodiment, amplification can be performed using Taq ligase for amplification (Barmy (1991) *Proc. Natl. Acad. Sci. USA* 88:189). In such cases, ligation will occur only if there is a perfect match at the 3' end of the 5' sequence, making it possible to detect the presence of a known mutation at a specific site by looking for the presence or absence of amplification.

Enzymatic methods for detecting sequences include amplification-based methods such as the polymerase chain reaction (PCR; Saiki et al. (1985) *Science* 230:1350-1354) and ligase chain reaction (LCR; Wu et al. (1989) *Genomics* 4:560-569; Barringer et al. (1990) *Gene* 1989:117-122; F. Barany (1991) *Proc. Natl. Acad. Sci. USA* 1988:189-193); transcription-based methods utilizing RNA synthesis by RNA polymerases to amplify nucleic acid (U.S. Pat. Nos. 6,066,457; 6,132,997; and 5,716,785; Sarkar et al. (1989) *Science* 244:331-334; Stoller et al. (1988) *Science* 239:491); NASBA (U.S. Pat. Nos. 5,130,238; 5,409,818; and 5,554,517); rolling circle amplification (RCA; U.S. Pat. Nos. 5,854,033 and 6,143,495), and strand displacement amplification (SDA; U.S. Pat. Nos. 5,455,166 and 5,624,825). Amplification methods can be used in combination with other techniques.

Other enzymatic techniques include sequencing using polymerases, e.g., DNA polymerases and variations thereof, such as single base extension technology. See, e.g., U.S. Pat. Nos. 6,294,336; 6,013,431; and 5,952,174.

Fluorescence-based detection can also be used to detect nucleic acid polymorphisms. For example, different terminator ddNTPs can be labeled with different fluorescent dyes. A primer can be annealed near or immediately adjacent to a polymorphism, and the nucleotide at the polymorphic site can be detected by the type (e.g., "color") of the fluorescent dye that is incorporated.

Hybridization to microarrays can also be used to detect polymorphisms, including SNPs. For example, a set of different oligonucleotides, with the polymorphic nucleotide at varying positions within the oligonucleotides, can be positioned on a nucleic acid array. The extent of hybridization as a function of position and hybridization to oligonucleotides specific for the other allele can be used to determine whether a particular polymorphism is present. See, e.g., U.S. Pat. No. 6,066,454.

In one implementation, hybridization probes can include one or more additional mismatches to destabilize duplex formation and sensitize the assay. The mismatch may be directly adjacent to the query position, or within 10, 7, 5, 4, 3, or 2 nucleotides of the query position. Hybridization probes can also be selected to have a particular $T_m$ e.g., between 45-60° C., 55-65° C., or 60-75° C., In a multiplex assay, $T_m$'s can be selected to be within 5, 3, or 2° C. of each other.

It is also possible to directly sequence the nucleic acid for a particular genetic locus, e.g., by amplification and sequencing, or amplification, cloning and sequencing. High throughput automated (e.g., capillary or microchip based) sequencing apparati can be used. In still other embodiments, the sequence of a protein of interest is analyzed to infer its genetic sequence. Methods of analyzing a protein sequence include protein sequencing, mass spectroscopy, sequence/epitope specific immunoglobulins, and protease digestion.

Any combination of the above methods can also be used. The above methods can be used to evaluate any genetic locus, e.g., in a method for analyzing genetic information from particular groups of individuals or in a method for analyzing a polymorphism associated with a neuronal or other injury or pathology in the brain or spinal cord or other neurological disorder, e.g., in a gene encoding TWEAK or a TWEAK receptor.

EXAMPLES

Example 1

TWEAK and Fn14 Levels in FALS

FIG. 1 shows that Fn14 is upregulated in an animal model of ALS, indicating that blocking the TWEAK/TWEAK-R pathway can be used as a therapeutic strategy to treat ALS.

Example 2

MPTP Model for Parkison's Disease

Figure 2:
FIG. 2 is a bar graph showing that Fn14 wild type (WT) and knock out (KO) mice have similar numbers of TH+ neurons and a plot showing that Fn14 knock out mice have reduced TH+ neuron loss following MPTP treatment relative to wild type.

The MPTP mouse model is widely-used animal model for Parkinson's Disease. It is an excitotoxic model of dopaminergic neurodegeneration. MPTP is injected IP and MPTP intoxication causes death of dopaminergic neurons in substantia nigra (SN). Gliosis is measured on day 1, 2 and tyrosine hydroxylase (TH)+ cell survival in substantia nigra on day 7. As shown in FIG. 2, Fn14 knock-out mice are protected against MPTP toxicity.

Figure 3:
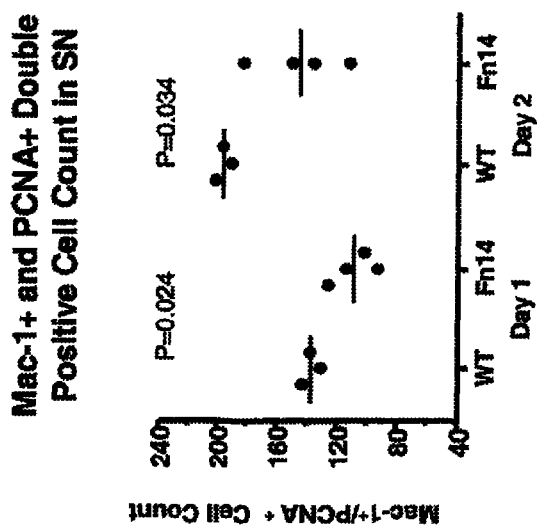
FIG. 3 is a plot showing that Fn14 deficiency reduces microglial activation following MPTP treatment. WT=wild type; Fn14=Fn14 deficient.

The effect of Fn14 deficiency on microglial activation in the MPTP model was also analyzed. Mac-1 and PCNA double positive cells in the substantia nigra were counted on day 1 and day 2 after MPTP injection. As shown in FIG. 3, Fn14 deficiency reduces microglial activation after MPTP injection.

The data indicate that blocking the TWEAK/TWEAK receptor pathway can be used as a therapeutic strategy to treat Parkinson's disease.

Example 3

An Exemplary Sequence of a Human Tweak Protein is as Follows (SEQ ID NO: 1)
```
MAARRSQRRR GRRGEPGTAL LVPLALGLGL ALACLGLLLA

VVSLGSRASL SAQEPAQEEL VAEEDQDPSE LNPQTEESQD

PAPFLNRLVR PRRSAPKGRK TRARRAIAAH YEVHPRPGQD

GAQAGVLGTV SGWEEARINS SSPLRYNRQI GEFIVTRAGL

YYLYCQVHFD EGKAVYLKLD LLVDGVLALR CLEEFSATAA

SSLGPQLRLC QVSGLLALRP GSSLRIRTLP WAHLKAAPFL

TYFGLFQVH
```

An exemplary sequence of a human Fn14 protein is as follows:

(SEQ ID NO: 2)
```
MARGSLRRLL RLLVIALWLA LLRSVAGEQA PGTAPCSRGS

SWSADLDKCM DCASCPARPH SDFCLGCAAA PPAPFRLLWP

ILGGALSLTF VLGLLSGFLV WRRCRRREKF TTPIEETGGE

GCPAVALIQ
```

A number of embodiments of the invention have been described. Nevertheless, it will be understood that various modifications may be made without departing from the spirit and scope of the invention. Accordingly, other embodiments are within the scope of the following claims.

---

What is claimed is:

1. A method of treating a human subject who has Parkinson's Disease, comprising administering to the human subject a therapeutically effective amount of an anti-TWEAK (TNF-like weak inducer of apoptosis) antibody or antigen-binding fragment thereof that blocks TWEAK / TWEAK-R (TNF-like weak inducer of apoptosis-receptor) interaction.

2. The method of claim 1, wherein the anti-TWEAK antibody or antigen-binding fragment thereof is humanized.

3. The method of claim 1, wherein the anti-TWEAK antibody or antigen-binding fragment thereof is monoclonal.

4. The method of claim 1, wherein a full-length anti-TWEAK antibody is administered.

5. The method of claim 4, wherein the full-length anti-TWEAK antibody is a full-length IgG antibody.

6. The method of claim 1, wherein the anti-TWEAK antibody or antigen-binding fragment thereof is human.

7. The method of claim 1, wherein the treatment comprises administering the anti-TWEAK antibody or antigen-binding fragment thereof in combination with a second agent for treating Parkinson's disease.

8. The method of claim 7, wherein the second agent is a dopamine agonist or an MAO-B inhibitor.

9. The method of claim 7, wherein the second agent is selected from the group consisting of levodopa, ropinrole, pramipexole, pergolide, and R(+)-N-propargyl-1-aminoindan.

10. The method of claim 1, wherein the TWEAK-R is Fn14.

11. The method of claim 10, wherein the anti-TWEAK antibody or antigen-binding fragment thereof is administered via a route selected from the group consisting of: intravenous, intramuscular, intraarterial, intrathecal, intracapsular, intraorbital, intradermal, intraperitoneal, transtracheal, subcutaneous, subcuticular, intraarticular, subcapsular, subarachnoid, intraspinal, epidural, intrasternal injection or infusion, and directly into the central nervous system.

12. The method of claim 11, wherein the anti-TWEAK antibody or antigen-binding fragment thereof is administered via a subcutaneous route.

13. The method of claim 11, wherein the anti-TWEAK antibody or antigen-binding fragment thereof is administered via an intravenous route.

14. The method of claim 10, wherein the anti-TWEAK antibody or antigen-binding fragment thereof is in a delivery formulation selected from the group consisting of a tablet, pill, powder, dispersion, suspension, liposome, suppository, liquid, emulsion, implant, and sustained-release formulation.

15. The method of claim 14, wherein the anti-TWEAK antibody or antigen-binding fragment thereof is in a liquid delivery formulation.

16. The method of claim 10, wherein the anti-TWEAK antibody or antigen-binding fragment thereof is humanized.

17. The method of claim 10, wherein the anti-TWEAK antibody or antigen-binding fragment thereof is human.

18. The method of claim 10, wherein a full-length anti-TWEAK IgG antibody is administered.

19. The method of claim 10, wherein the treatment comprises administering the anti-TWEAK antibody or antigen-binding fragment thereof in combination with a second agent for treating Parkinson's disease.

20. The method of claim 19, wherein the second agent is a dopamine agonist or an MAO-B inhibitor.

21. The method of claim 19, wherein the second agent is selected from the group consisting of levodopa, ropinrole, pramipexole, pergolide, and R(+)-N-propargyl-1-aminoindan.

22. The method of claim 10, wherein an antigen-binding fragment of an anti-TWEAK antibody is administered.

23. The method of claim 22, wherein the antigen-binding fragment of the anti-TWEAK antibody is fused to an antibody Fc region.

24. The method of claim 22, wherein the antigen-binding fragment of the anti-TWEAK antibody comprises a single chain antibody, a Fab fragment, a F(ab')$_2$ fragment, a Fd fragment, a Fv fragment, or a dAb fragment.

* * * * *

UNITED STATES PATENT AND TRADEMARK OFFICE
CERTIFICATE OF CORRECTION

| | | |
|---|---|---|
| PATENT NO. | : 9,775,899 B2 | Page 1 of 1 |
| APPLICATION NO. | : 13/718788 | |
| DATED | : October 3, 2017 | |
| INVENTOR(S) | : Linda C. Burkly et al. | |

It is certified that error appears in the above-identified patent and that said Letters Patent is hereby corrected as shown below:

In the Specification

Column 1
Line 6, delete "Ser.No." and insert -- Ser. No. --.

Column 1
Line 11, delete "60/653,813filed" and insert -- 60/653,813 filed --.

In the Claims

Column 39, Claim 9
Line 60, delete "ropinrole," and insert -- ropinirole, --.

Column 41, Claim 21
Line 2, delete "ropinrole," and insert -- ropinirole, --.

Signed and Sealed this
Fourteenth Day of November, 2017

Joseph Matal
*Performing the Functions and Duties of the*
*Under Secretary of Commerce for Intellectual Property and*
*Director of the United States Patent and Trademark Office*